United States Patent
Howard et al.

(10) Patent No.: US 10,308,948 B2
(45) Date of Patent: Jun. 4, 2019

(54) METHOD OF INCREASING EXPRESSION OF NUCLEIC ACID MOLECULES IN PLANTS USING MULTIPLE TRANSCRIPTION UNITS

(71) Applicant: Applied Biotechnology Institute, Inc., San Luis Obsipo, CA (US)

(72) Inventors: John Howard, Cayucos, CA (US); Erin Egelkrout, San Luis Obispo, CA (US); Celine Hayden, San Luis Obispo, CA (US)

(73) Assignee: Applied Biotechnology Institute, Inc., San Luis Obispo, CA (US)

( * ) Notice: Subject to any disclaimer, the term of this patent is extended or adjusted under 35 U.S.C. 154(b) by 1020 days.

(21) Appl. No.: 13/654,673

(22) Filed: Oct. 18, 2012

(65) Prior Publication Data
US 2013/0042370 A1 Feb. 14, 2013

Related U.S. Application Data
(63) Continuation-in-part of application No. 13/558,834, filed on Jul. 26, 2012, now Pat. No. 9,944,937.
(Continued)

(51) Int. Cl.
*C12N 15/82* (2006.01)
*C12N 15/113* (2010.01)

(52) U.S. Cl.
CPC ........ *C12N 15/8216* (2013.01); *C12N 15/113* (2013.01); *C12N 15/8234* (2013.01); *C12N 15/8257* (2013.01); *C12N 15/8258* (2013.01)

(58) Field of Classification Search
CPC ................................................ C12N 15/8234
See application file for complete search history.

(56) References Cited

U.S. PATENT DOCUMENTS
4,287,304 A 9/1981 Muller
4,302,543 A 11/1981 Benyaev et al.
(Continued)

FOREIGN PATENT DOCUMENTS
WO WO 97/25468 A1 7/1997
WO WO 98/39461 A1 11/1998
(Continued)

OTHER PUBLICATIONS
Rombauts et al. 2003. Computational approaches to identify promoters and cis-regulatory elements in plant genomes. Plant Physiology. 2003. 132:1162-1176.*
(Continued)

*Primary Examiner* — Ashley K Buran
*Assistant Examiner* — Karen M Redden
(74) *Attorney, Agent, or Firm* — McKee, Voorhees & Sease, PLC

(57) ABSTRACT

A method of increasing expression of a product encoded by a nucleic acid molecule is provided where in one embodiment multiple plant transcription units comprising a promoter and the nucleic acid molecule are provided. In another embodiment multiple plant transcription units are provided where each promoter is different from the other. In an embodiment the multiple plant transcription units may comprise two, three, four or more plant transcription units. In another embodiment the promoter may be selected from an embryo promoter. Another embodiment provides the promoter may be a globulin promoter. A further embodiment provides the product encoded may be selected from hepatitis b, aprotinin, or a cellulase. Still further embodiments provide the product may be selected from the cellulases E1 and CBH1.

5 Claims, 16 Drawing Sheets
Specification includes a Sequence Listing.

Related U.S. Application Data

(60) Provisional application No. 61/549,343, filed on Oct. 20, 2011, provisional application No. 61/512,347, filed on Jul. 27, 2011.

(56) References Cited

U.S. PATENT DOCUMENTS

| | | | |
|---|---|---|---|
| 4,330,625 A | 5/1982 | Miller et al. | |
| 4,347,321 A | 8/1982 | Lionelle et al. | |
| 4,407,955 A | 10/1983 | Muller | |
| 4,415,659 A | 11/1983 | Ronkainen et al. | |
| 4,416,989 A | 11/1983 | Kretz | |
| 4,425,433 A | 1/1984 | Neves | |
| 4,448,881 A | 5/1984 | Muller | |
| 4,617,270 A | 10/1986 | Anderson et al. | |
| 4,810,647 A | 3/1989 | Monceaux et al. | |
| 4,952,503 A | 8/1990 | Gransedt | |
| 5,100,791 A | 3/1992 | Spindler et al. | |
| 5,231,017 A | 7/1993 | Lantero et al. | |
| 5,543,576 A | 8/1996 | Van Ooijen et al. | |
| 5,545,543 A | 8/1996 | Zinnamosca et al. | |
| 5,677,154 A | 10/1997 | Van Draanen et al. | |
| 5,932,456 A | 8/1999 | Van Draanen et al. | |
| 5,981,237 A | 11/1999 | Meagher et al. | |
| 5,981,835 A | 11/1999 | Austin-Phillips et al. | |
| 6,013,860 A | 1/2000 | Himmel et al. | |
| 6,818,803 B1 | 11/2004 | Austin-Phillips et al. | |
| 7,102,057 B2 | 9/2006 | Lanahan et al. | |
| 7,112,723 B2 | 9/2006 | Streatfield et al. | |
| 7,169,967 B2 | 1/2007 | Streatfield et al. | |
| 7,183,109 B2 | 2/2007 | Streatfield et al. | |
| 7,361,806 B2 | 4/2008 | Lebel et al. | |
| 8,558,058 B2 | 10/2013 | Hood et al. | |
| 8,642,749 B2 | 2/2014 | Streatfield et al. | |
| 8,709,742 B2 | 4/2014 | Howard et al. | |
| 8,709,761 B2 | 4/2014 | Howard et al. | |
| 2002/0078472 A1 | 6/2002 | Christou et al. | |
| 2003/0074700 A1 | 4/2003 | Huang et al. | |
| 2003/0109011 A1 | 6/2003 | Hood et al. | |
| 2008/0022425 A1 | 1/2008 | Lebel et al. | |
| 2008/0078005 A1 | 3/2008 | Lebel et al. | |
| 2009/0205086 A1* | 8/2009 | Hood | C12N 15/8242 800/298 |
| 2013/0031664 A1 | 1/2013 | Howard et al. | |

FOREIGN PATENT DOCUMENTS

| | | |
|---|---|---|
| WO | WO 99/16890 A2 | 4/1999 |
| WO | WO9966026 A2 | 12/1999 |
| WO | WO0004146 A2 | 1/2000 |

OTHER PUBLICATIONS

Meyer and Saedler. 1996. Annu. Rev. Plant Physiol. Plant Mol. Biol. 47: 23-48.*

Streatfield. 2007. Approaches to achieve high-level heterologous protein production in plants. Plant Biotechnology Journal 5: 2-15.*

Streatfield et al. 2010. Identification of maize embryo-preferred promoters suitable for high-level heterologous protein production. GM Crops 1:3: 162-172. (Year: 2010).*

Kriz et al. (1986) "Synthesis of globulins in maize embryos" Plant Physiol. 82, 1069-1075.

Kriz et al. (1991) "Characterization of the maize Globulin-2 gene and analysis of two null alleles" Biochem. Gen. vol. 29., Nos. 5/6 pp. 241-254.

Yu et al. (2007) "Expression of thermostable microbial cellulases in the chloroplasts of nicotine-free tobacco" Journal of Biotechnology 131.3: 362-369.

Kawazu et al. (1996) "Expression of a Ruminococcus albus cellulase gene in tobacco suspension cells" Journal of Fermentation and Bioengineering vol. 82, No. 3, 205-209.

Kawazu et al. (1999) "Expression of a bacterial endoglucanase gene in tobacco increases digestibility of its cell wall fibers" Journal of Bioscience and Bioengineering vol. 88 No. 4, 421-425.

Sun et al. (2007) "Expression and characterization of Acidothermus cellulolyticus E1 endoglucanase in transgenic duckweed *Lemna minor* 8627" Bioresource Technology 98.15: 2866-2872.

Matze et al. Deletion analysis of a zein gene promoter in transgenic tobacco plants (1990) PMB; vol. 14, pp. 323-332.

Rishi et al. Molecular Farming in plants: a current perspective (2001) J. Plant Biochem. & Biotech; vol. 10, pp. 1-12.

Whitelam G.C. The production of recombinant proteins in plants (1995) J. Sci. Food Agric.; vol. 68; pp. 1-9.

Napier et al. Trafficking and stability of heteologous proteins in transgenic plants (1998) In: Methods in Biotechnology; vol. 3; Chapter 15, pp. 189-202.

Verwoer Verwoer et al. Stable accumulation of Aspergillus niger phytase in transgenic tobacco leaves. Plant Physiol. 109:1199-1205 (1995).

Lacki Lacki et al. Stability of a polphenol oxidase from the white-rot fungus *Trametes versicolor* in the presence of canola meal. Acta Biotechnol. 19 (1999) 2, 91-100.

Tucker et al. Ultra-thermostable cellulases from Acidothermus celluloyticus: comparison of temperature optima with previously reported cellulases. Bio/Technology vol. 7, Aug. 1989.

Blum et al. Feruloyl Exterase of the Clostridium thermocellum cellulosome can be attributed to previously unknown domains of XynY and XynZ. Journal of Bacteriology, Mar. 2000, p. 1346-1351, vol. 182, No. 5.

Hood et al. Molecular farming of industrial proteins from transgenic maize. Chemicals via Higher Plant Bioengineering, edited by Shahidi et al. Kluwer/Plenum Publishers, New York, 1999, pp. 127-147.

Baker et al., A new thermostable endoglucanase, Acidothermus cellulyticus E1, applied Biochemistry and Biotechnology., vol. 45-46, 1994.

Sreenath et al., Enzymatic saccharification of alfalfa fiber after liquid hot water pretreatment. Process Biochemistry 35 (19999) 33-34.

Maijala Heterobasidion annosum and wood decay: Enzymology of cellulose, hemicellulose and lignin degradation, Dissertation, University of Helsinki, Mar. 31, 2000.

Aspegren et al, Molecular Breeding 1:91-99 (1995).

Hooker et al. pp. 55-90 in: Glycosyl hydrolases for biomass conversion, ACS Symposium Series, vol. 769, Himmel et al., eds, american Chemical Society: Washington DC (2001).

Herbers et al., Thermostable xylanase from Clostridium thermocellum expressed at high levels in the apoplasty of transgenic tobacco has no detrimental effects and is easily purified. Bio/Technology vol. 13, Jan. 1005.

Hood et al., Industrial proteins produced from transgenic plants, in Plants as Factories for Protein Production, Hood, Howard editors, Kluwer Publishing (2002) pp. 119-135.

Sheehan J., The road to bioethanol: a strategic perspective of the US Department of Energy's national ethanol program. Glycosyl Hydrolases for Biomass Conversion, pp. 2-25 (2001).

Law et al. Biochemical limitations to high-level expression of humanized monoclonal antibodies in transgenic maize seed endosperm. (2006) Biochimica et Biophysica Acta; vol. 1760; pp. 1434-1444.

GenBank Ref No. AR947679.1 Sequence 4 from U.S. Pat. No. 7,112,723, Oct. 8, 2006.

GenBank Ref No. HM635908.1 *Zea mays* pr36 gene, promoter region and 5'UTR, Nov. 15, 2010.

Streatfield et al. "Identification of maize embryo-preferred promoters suitable for high-level heterologous protein production" GM Crops 1:3, 162-172, May/Jun. 2010.

Wallace et al. "Nucleotide Sequence of a cDNA Clone Corresponding to the Maize Globulin-2 Gene" PLant :Physiol. (1991) 95, 973-975.

GenBank Ref No. X53715.1 *Z. mays* mRNA for globulin-2, Dec. 15, 2002.

Egelkrout et al. "Cellulase expression using maize embryo promoters suitable for high-level heterologous protein production" American Society of Plant Biologists, ABS #P01055, Jul. 31, 2010.

(56) References Cited

OTHER PUBLICATIONS

Hood et al. "Subcellular targeting is a key condition for high-level accumulation of cellulase protein in transgenic maize seed" Platn Biotechnology Journal (2007) 5, pp. 709-719.
Egelkrout et al. Enhanced expression levels of cellulase enzymes using multiple transcription units Bioenerg. Res. (2013) 6:699-710.
Hennegan et al (2005) Improvement of human lysozyme expression in transgenic rice grain by combining wheat (Triticum aestivum) puroindoline b and rice (Oryza sativa) Gt1 promoters and signal peptides. Transgenic Research 14:583-592.
Belanger and Kriz (1991) "Molecular basis for Allelic Polymorphism of the maize Globulin-1 gene" Genetics 129:863-972.
GenBank accession No. L22344Aug. 4, 1993.
Kriz (1989) "Characterization of embryo globulins encoded by the maize Glb genes" Biochem Genet. 27(3-4):238-51.
Liu et al. (1992) MNL vol. 22: 108-109.
Hood et al. (2003) Criteria for high-level expression of a fungal laccase gene in transgenic maize. Plant Biotechnol. J. 1, 129-140.
Woodard et al. (2003) Maize-derived bovine trypsin: characterization of the first large-scale, commercial protein product from transgenic plants. Biotechnol. Appl. Biochem. 38,123-130.
GenBank Accession No. EA076965, Sequence 3 from U.S. Pat. No. 7,183,109, Apr. 11, 2007.
Belanger and Kriz AL (1989) Molecular Characterization of the Major Maize Embryo Globulin Encoded by the Glb1 Gene. Plant Physiol 91:636-643.
Mohagheghi et al. (1986) Isolation and Characterization of Acidothermus-Cellulolyticus Gen-Nov, Sp-Nov, a New Genus of Thermophilic, Acidophilic, Cellulolytic Bacteria. International Journal of Systematic Bacteriology 36:435-443.
Nieves et al. Nieves (1995) Quantitation of Acidothermus-Cellulolyticus E1 Endoglucanase and Thermomonospora-Fusca E(3) Exoglucanase Using Enzyme-Linked-Immunosorbent-Assay (Elisa). Applied Biochemistry and Biotechnology 51-2:211-223.
Shoemaker et al. (1983) Molecular-Cloning of Exo-Cellobiohydrolase-I Derived from Trichoderma-Reesei Strain-L27. Bio-Technology 1:691-696.
Baker et al. (1998) Hydrolysis of cellulose using ternary mixtures of purified celluloses. Appl Biochem Biotechnol 70-72:395-403.
Hood et al. Manipulating corn germplasm to increase recombinant protein accumulation. Plant Biotechnol J. Jan. 2012;10(1):20-30. doi: 10.1111/j.1467-7652.2011.00627.x. Epub Jun. 1, 2011.
GenBank accession No. L22656 Phanerochaete chrysosporium major cellobiohydrolase (cbh1-4) gene, complete cds, Apr. 12, 2001.
Walsh et al. Biomass feedback availability in the United States: 1999 state level analysis. http://bioenery.ml.gov/resourcedatatindex.htm.
Dai et al. (2000) Expression of Acidothermus cellulolyticus endoglucanase E1 in transgenic tobacco: biochemical characteristics and physiological effects. Transgenic Res 9:43-54.
Ziegler (2000) Accumulation of a thermostable endo-1, 4- -D-glucanase in the apoplast of Arabidopsis thaliana leaves. Molecular Breeding 6:37-46.
Biswas et al. (2006) Expression of biologically active Acidothermus cellulolyticus endoglucanase in transgenic maize plants. Plant Science 171:617-623.
Mei et al. (2009) Green tissue specific production of a microbial endo cellulase in maize (Zea mays L.) endoplasmic reticulum and mitochondria converts cellulose into fermentable sugars. Journal of Chemical Technology & Biotechnology 84:689-695.
Ransom et al. (2007) Heterologous Acidothermus cellulolyticus 1,4-beta-endoglucanase E1 produced within the corn biomass converts corn stover into glucose. Applied Biochemistry and Biotechnology 137:207-219.
Oraby et al. (2007) Enhanced conversion of plant biomass into glucose using transgenic rice-produced endoglucanase for cellulosic ethanol. Transgenic Research 16:739-749.
Gray et al. (2011) An efficient downstream box fusion allows high-level accumulation of active bacterial beta-glucosidase in tobacco chloroplasts. Plant Molecular Biology:1-11.
Brunecky et al. (2011) In planta expression of A. cellulolyticus Cel5A endocellulase reduces cell wall recalcitrance in tobacco and maize. Biotechnology for biofuels 4:1.
Douglas et al. (2009) Gene Stacking. Molecular Techniques in Crop Improvement:613-629.
Halpin (2005) Gene stacking in transgenic plants—the challenge for 21st century plant biotechnology. Plant Biotechnology Journal 3:141-155.
Aluru et al. (2008) Generation of transgenic maize with enhanced provitamin A content. J Exp Bot 59:3551-3562.
Naqvi et al. (2010) Simultaneous expression of Arabidopsis rho-hydroxyphenylpyruvate dioxygenase and MPBQ methyltransferase in transgenic corn kernels triples the tocopherol content. Transgenic Res 20:177-181.
Naqvi et al. (2009) Transgenic multivitamin corn through biofortification of endosperm with three vitamins representing three distinct metabolic pathways. Proc Natl Acad Sci U S A 106:7762-7767.
Howard et al. (2007) Methods for growing nonfood products in transgenic plants. Crop Science 47:1255-1262.
Howard et al. (2011) Enzyme Production Systems for Biomass Conversion, in Plant Biomass Conversion (Hood E, Nelson P and Powell R eds) pp. 227-255, Chichester: Wiley-Blackwell.
GenBank accession S62754.1=surface antigen [hepatitis B virus, isolate B12, Genomic, 1203 nt], Apr. 21, 2003.
Streatfield et al. (2007) Approaches to achieve high-level heterologous protein production in plants. Plant Biotechnology Journal 5:2-15.
Petersen K and Bock R (2011) High-level expression of a suite of thermostable cell wall-degrading enzymes from the chloroplast genome. Plant Molecular Biology:1-11.
Dai et al. Improved plant-based production of E1 endoglucanase using potato: expression optimization and tissue targeting. Molecular Breeding 6:277-285 (2000).
Ziegelhoffer et al. Expression of bacterial cellulose genes in transgenic alfalfa (Medicago sativa L.) potato (Solanum tuberosum L.) and tobacco (Nicotiana tabacum L) Molecular Breeding 4:309-319 (1999).
Jensen et al. Transgenic barley expressing a protein-engineered thermostable (1.3-1,4) beta-glucanase during germination. Proc. Natl. Acad. Sci. U>S>A> 93:3487-3491 (1996).
Dai et al. Over-expresion of cellulass in transgenic tobacco whole plants (1998) Poster: ASPP Annual Meeting vol. 1998 p. 85.
Horvath et al. The production of recombinant proteins in transgenic barley grains. (2000) PNAS vol. 97; pp. 1914-1919.
Hayden et al, "Production of highly concentrated, heat-stable hepatitis B surface antigen in maize" Plant Biotechnology Journal Oct. 2012;10(8):979-84.
Zhong et al. (1999) Commercial production of aprotinin in transgenic maize seeds. Molecular Breeding 5:345-356.
Dai et al. (1999) Expression of Trichoderma reesei Exo-Cellobiohydrolase I in Transgenic Tobacco Leaves and Calli, Applied Biochemistry and Biotechnology; vol. 77-79, pp. 689-699.

* cited by examiner

Figure 1

```
   1 aagcttgccg agtgccatcc ttggacactc gataaagtat attttatttt ttttattttg
  61 ccaaccaaac tttttgtggt atgttcctac actatgtaga tctacatgta ccattttggc
 121 acaattacat atttacaaaa atgttttcta taaatattag atttagttcg tttatttgaa
 181 tttcttcgga aaattcacat ttaaactgca agtcactcga aacatggaaa accgtgcatg
 241 caaaataaat gatatgcatg ttatctagca caagttacga ccgatttcag aagcagacca
 301 gaatcttcaa gcaccatgct cactaaacat gaccgtgaac ttgttatcta gttgtttaaa
 361 aattgtataa aacacaaata aagtcagaaa ttaatgaaac ttgtccacat gtcatgatat
 421 catatataga ggttgtgata aaaatttgat aatgtttcgg taaagttgtg acgtactatg
 481 tgtagaaacc taagtgacct acacataaaa tcatagagtt tcaatgtagt tcactcgaca
 541 aagactttgt caagtgtccg ataaaaagta ctcgacaaag aagccgttgt cgatgtactg
 601 ttcgtcgaga tctctttgtc gagtgtcaca ctaggcaaag tctttacgga gtgttttttca
 661 ggctttgaca ctcggcaaag cgctcgattc cagtagtgac agtaatttgc atcaaaaata
 721 gctgagagat ttaggccccg tttcaatctc acgggataaa gtttagcttc ctgctaaact
 781 ttagctatat gaattgaagt gctaaagttt agtttcaatt accaccatta gctctcctgt
 841 ttagattaca aatggctaaa agtagctaaa aaatagctgc taaagtttat ctcgcgagat
 901 tgaaacaggg ccttaaaatg agtcaactaa tagaccaact aattattagc tattagtcgt
 961 tagcttcttt aatctaagct aaaaccaact aatagcttat tgttgaatt acaattagct
1021 caacggaatt ctctgttttt ctaaaaaaaa actgcccctc tcttacagca aattgtccgc
1081 tgcccgtcgt ccagatacaa tgaacgtacc tagtaggaac tcttttacac gctcggtcgc
1141 tcgccgcgga tcggagtccc cggaacacga caccactgtg gaacacgaca aagtctgctc
1201 agaggcggcc acccctggc gtgcaccgag ccggagcccg gataagcacg gtaaggagag
1261 tacggcggga cgtggcgacc cgtgtgtctg ctgccacgca gccttcctcc acgtagccgc
1321 gcggccgcgc cacgtaccag ggcccggcgc tggtataaat gcgcgccacc tccgctttag
1381 ttctgc*atac agccaaccca a*
```

GGATCCAACACACACCCGAGGATATCACAGTCGACACTACACC cggtatgaatttggaaacaaattcagtacttttaaaaaaatttgttgtagggagcaaataatacataaaataatttatgcattattttattt
tttatttgtaataatatgcttgaaacgataattcagtatgcatgttgtgccagtgtactacacgggcggggggaggggattgagtgg
gccagcgcggtgcgtagggtagatgggctgaaattgataactcaagtccgactaggttctctttttatttcccttcctttttctatttcct
ttcttttaattttcatgctttcaaactaaattcaaattcgagttttgaatttcagcttctaaattgtacactaaaattatatgataaggtaacc
cctactattacttttaattttttattctaccccatattgtttacttaggggagaataattgacttaatcacattcttcctaggttttcaattctca
atctttcaaatccacattttagatttctattttgaatttaaataccagtttggatttagagttcaatttcaaaatacacaaccaaaatacca
gcatgaatgcaaatatattttatgttatgtatttactttcttttatactttgctcaaaatagttattttcatgtatgaaactcaataagcaag
gaactcacgttattatataacctaataggaataatttaggtaacataatttatcatcctcttgatttaaaagagatatgcctccagaata
agacacatactaaaaataactctaatattgaataactaaagtcgtacaaatctctactattattcctataaaataataaagaactagcta
caacttcttaaggcattattcagggtttacagcttgagaggcatgaacccatcctgtatactcctggacttggaagacaaaatgtca
accaaagtgaaaggttttcttatggttgctgctaagagatagattgaacactagatctctcctaagacgtcagggcatgcgtttaga
ctcctacacatgcgaaaactgcatcttacagttggaagaaactatatctcaccacttcctgcggtgtaactttgcccaaagatgttgg
ctcactgttggaatcactccgccccgaactttggatctaacgcttgcagtgctacatattagagcaagactaacaatgccgtggag
aatggaaggtattataaccatgtcatggtgcatatggaaatgtcgaaataactggatattcgaaaacataccgccaacggtggcg
gcctgcaaggaaatgttcaagactgaaatgaactacatctgctaccaagttaagctcgagacaggagctaaagtagaaactgg
atacaacactttgtaacatagtgacactcccctttccttttcttttaccttagaactatacatacaatccacattcaataaaaatttgtagg
tacgccatacacactaccggaatccggctctttgccgagtgtgaggcgctttgtcgagtgcttttttgtccagcactcggcaaaaaa
gtctttgccatgtgccgcactcggcaaagtcctgctctcggtaacgaccgcgtttaccgagagcaggactctcgacacagaaata
cactcgacaaagaaatctttgccgagagccaaacactcggcgaacggcagcgctcggcaaagggtcgtcagccgccgtctaa
agctgacggtcgttatctttgtcgagtgcccccctcgtccgacactcagtagagcaagcttgccgagtgccatccttggacactcga
taaagtatattttatttttttttatttgccaaccaaacttttttgtggtatgttcctacactatgtagatctacatgtaccattttggcacaatta
caaaaatgttttctataactattagatttagttcgtttatttgaatttcttcggaaaattcacatatgaactgcaagtcactcgaaacatga
aaaaccgtgcatgcaaaataaatgatatgcatgttatctagcacaagttacgaccgaattcagaagcagaccagaatcttcaagc
accatgctcactaaacatgaccgtgaacttgttatccagttgtttaaaaattgtataaaacacaaataaagtcagaaattaatgaaact
tgtccacatgtcatgatatcatatatagaggttgtgataaaaatttgataatgttcggtaaagttgtgacgtactatgtgtagaaacct
aagtgacctacacataaaatcatagagtttcaatgtagttcactcgacaaagactttgtcaagtgtccgataaaaagtattcagcaa
agaagccgttgtcgatttactgttcgtcgagatctctttgccgagtgtcacactaggcaaagtctttacggagtgttttttcaggctttg
acactcggcaaagcgctcgattccagtagtgacagtaatttgcatcaaaaatagccgagagatttaaaatgagtcaactaatagac
caactaattattagctattagtcgttagcttctttaatctaagctaaaaccaactaatagcttatttgttgaattacaattagctcaacgga
attctctgtttttctataaaaaaaagggaaactgccccctcatttacagcaaactgtccgctgcctgtcgtccagatacaatgaacgta
cctagtaggaactcttttacacgctcggtcgctcgccgcggatcggagtcccaggaacacgacaccactgtggaacacgacaa
agtctgctcagaggcggccacaccctggcgtgcaccgagccggagcccggataagcacggtaaggagagtacggcgggac
gtggcgacccgtgtgtctgctgccacgcagccttcctccacgtagccgcgcggccgcgccacgtaccagggccggcgctgg
tataaatgcgcgccacctccgctttagttctg**catacagccaacccaacacacacccgagcatatcacagtgacagacacta
cacgATG**

Figure 2

Figure 3 gcgatctgaagatctggtgaacctgagcctgacccatcaaatgtctataagttttctttgtagagaaattatcggctccccaaatgagtttccaa
gcatcatttgtattggccaccatgatttggccccaagttgcgtctaagtctagaaattgttcataagcttgcaccgacagaggtagctgaaaaat
ttcaataagttgttccttttggagagcttctttgatggtaagtttgctgttgcaagcaaaggaaaataactcaggatattgatgagccgggatgcc
cctattccacatatcttcccagaaaagaatggttcttccatccccgatagttggggcagccagtcccttgtaatcttggacaagagtaagcaag
cttttccaccaaaaggagccaattttttgagcaaccaggtagcctgactgtcctgtaatagttgctccaaaccaggttaacccagggaatatcat
gattgttgaaaaacttgtgcaaaaacttcagaagcaaggctttattgtgagtctctaatcttaccactcccaggcccccatttttttagtctgtgtaa
tcatactccaagtagctagagcaggtttctttgaattgacgtcgtttcctctccaaagacagtgtttccgataagaatcaatcttctttaccgtggt
aaccggaattttcagtgtgcacatcaaaaaggtcgggagagctgagaacaccgagttaacaagctcaagcctgccagcctgggagagga
gggcagaggtgcatgataatctcttttgaatcctatgaatgagcggtaaaaagtggcagattttaggctttgatagaccaagcggaacaccaa
gataggtaaagggcattgaacctatctgacagttgagggttcctgctaggatcgccattttagcaggactgacattgatggggtacatacttga
tttgttgtaattcaccttcaacccgtcgaagttgcaaaagagttcagaacggctctgagaaaaaatagctgtctagggcaagcttccattatca
gtagtgtgtcatccgcatattgaactatcggaaaatcttgaccacaattctcggccagggtaacttgagaaggtcttgctgccgcgctttattg
atgatgctctgtaacagatccgccgcgagaacaaaaagaagaggcgagaggggatctccctgcctaaccccacgcttgtagtgaaaggttt
tcccaggaacaccattaagaaggactgatgacgtgctagaccgaagaatatccctaatccagctcatccatctgggcccaaagcctctatgc
aacattacctgaagaatcaactcatgctcaagagaatcaaaagccttttcaaaatccaatttgagcacaataatctcttttttttgaaatatgacaaa
gatgaatatattcaaatgcccaggccagacaatcctgaatggttctttctttgatgaagccatattgattttgtgaacaagggaagtcatcactg
tctgtaaccggttagccagcagcttagtgatgattttcatactattattcagaagcgaaattggtctgaaatcgcccactaaactagcattatcctt
cttcggaatcaggacaatataagaaccattgatgcttcgaagacaaatatccccgtggtaaaattggtcacataagtcatagaagtcctggga
aataatcggacaacattttttttgataaagttggtattaaacccatcaggtcccggggatttatcagaaggaagggacgccacaatactatcaatt
tcttgctttgaaaaaggctcatctaaccaatgcaagtcattgcggcagagcaacaaactagaaagatcaaagacattatccacaaaatcgga
ggatcccaagcgacatttgaacatattccaaagcaggttagttttgagatcatgctctgtaaagattgagccactgtcatccaagagcaacgc
aattgtattacggccatgccacgcaactgtcatccaagaactttctactcttggattacacggataaagttgaagtactacaagcaactataaac
gactagagcctttgcttgagtcctttatacgcggtcgaagagtgtttgcctctttatttatttgttcagcaggccccgagaatcttcaccgctgaa
gcacacccgacccgaataattgataatattgctcaaatcatatgagatggacgctggctctgcagcttttagggcctgttcgtttgactcggaat
tcatcccggaattgttccagctaatcaaatgttatataaattagataaccaatccggctaggaatagttccggacggccaattcctcagaatcga
acgggcccttagctagtttcgagtcgtcggaatcagcttctgctagctaaatgttttgcttttcatagtctattttttgttagaatcgtttatataaaaat
tacatctaaatatagaatctatcgaatcgtcgtgatagtatgaatgtgatgctgcgcgtagactcctttgtcttctttagcacataaatcgtataaaa
attgtcgtaacagctattttttaagaatccagattatcagaaatctttgggaaaaaaagcactctctgaaaaagccccgcgtcgctacgtgcag
ctccatctgctccgtgttgtccccatcccaatcaccgctgtcgcttcgccgcaggcatcccagcagcgagctagcatgcacgcacgcacgc
aagcacacggcggcagctgcacggatgcggccgagtgcggtagcactgcagcgcgcgcgcgcgctccacatcgccttcgccccgcca
cgtacgcggcccggcctccacctggcggcgcgcatggctgcgaccctcgccgcgccaccctcttcatatacgccgcagctcgcttcgaacc
ctcgcatcgaacgcacactcgcactcgcagtcgcacgtacacggtacaccacactagctaccacagacgacgagcgccATG

Figure 4 cttcaattcctgtgtgttgtattactactgatacaatctccaattcttgtgaacttatgtatttggacttgtgtgaatttgtgatatgaacatatatccat
gtgtttgaaatctgtactgtatgtgatattttgtgttgcatgtgatattatgtttgtctaattttttatttctgtattttttattttttctagaaaagggttaaga
acgtgagtacccacgttcttaacgttaagaacgtgggtaccgtcgaacttattgtgcagacctcgcagacccacgcaggacacataaggtcg
acggccacgtggccccgtcgaacttaaccgtaagaacgtgggtgccgtcgaacttatgggaaaaaattcgacggccccgtcgaacttaaa
aacgcacgctcttaatgttaagttcgacggtacccacgttcttaatgttaagttcgacggtacccacattcttacttctctaagttcgtccaaaaat
cgctgtcggctatattcgtcggtaaacccacgttcttacggtaagttcgacggcttattacattaagttcgacggttttcacccacgttctttaac
cagtttcctgtagtgtatatgttggtaacctcgtacttagatgagcaatatgcactaccagaatcacgttctttgccgactgtctaagatactcacc
aaaagtcattttacactcggcaaataatactcgtcaaacattttatcggcaaaggattctttgccgagtactttttttggacactcggcaaagacttt
gccgagtgtcgaaaagcactcggcaaattaagaatcggaagcccccaaaaaacatcattttttttaaattataggaacaactctccaaccact
agtcattatcatatccaggtgatattcgaactcgcaacatctctctcgcgcataccctcctctaccactacactactacatcaattatgtctatatta
cgtttcattcctcatgtactataacaaatcgagagtaattttattatttaaggcactaaatgaattcatttgaaaatgtgaccaactataaagttgca
taacttttcgagacatataagttctattttgatagtttccacatacgagaccatttacaaaatttgaattcaaatttgaaaacttcacgcgaattttca
atgataagatgatttcaaatcaaaaaattgtcaattacaaagtttcattacatttcaagacctacaacttttatattggtgttttttccatccgaggtag
tttgaaaattcaaatttcaaaattcaaacatagttttgcatgacaatatgatttcaaaccaaaacattgtcaactacaaagttttcataactcttcaat
acctacaactttcatgttggtggttttttctttcggggtcgttttgaaaattcaaattttaaatattttaaattcagacgtagttttcgttgataaaatgac
ttcaaataaaaaagttgtcaactataaaaatgtgtaacttctcaaaatctataaaatttattttggttgtttggtcatttgttcatctcacattatggttct
aacaatatgcacaaatcttatacatctctctcgtagtttcataaactacgagagatatatgttttatgaacaaatttattttttattttgttatataagaa
atattcaaaatataaattgtacatcatgatgagttatacaaatttatagttgaaaattttttcatttaaattaatttactgcttaaaatgtgattttaaatt
gtccttacatagtgttgaaaaaagcactcggcaaaaaagctctttgccgagtgttttattttttgacactcggcaaaatgcttctttatcgagtgtaa
aaaaatactcgacaagtgtcaaaaataaaacactcggcaaagagcttctttgccgagtgttttgttttaccgagggttttgcgtgacactcgat
aaagagcttgtttgctgagttccgaaaaaaacactcgacgaaatatttagcattcgacgaagagccaaatttattagtgatgagactaaaaaa
ctgtttagttcgtggctaattatattatactttatttaaggttggttgttgtaatcgaagaactaacgttagatatagggccccttggtagggcttatt
tttcagcttcggctctggctcatgcaaaagttatgccaaacacctcttttttcaaatggcttcaccaatgaagtgcttttttcaaaatgaactagagg
gcatgagccaaaaaaagtggctcacccggcttcagctcacgtcattttgcacaatagccctcccaccagtccaaattatttttttggtcctgcc
ctcaatccctagccacgcacaatagccctcccaccagtccaaactatacaagggtctttctgaaaaataacctataagccgttttgccaaatga
attttcagaatggctttggctcatctaaagaagtggcttcacctcgtgagccagagccaaagccgttttggagaagccagagccctgccaaa
ggggcccataataagccgtagaaccaaacaatcccgaagctcaccagctactcactctagagtcctgctcctgccacagtgccagttgcgc
ctcacgcagccacgcaggaataggataagcactatactacgcacgctctggcttccgcttcgtagatgcatgcgtgtcgccgccggaggct
ctcgccgcgcacgcgtcgcgcgctgcggtggtaacga**cttcacggggtgtcccagcgtagcgtccgcgtcggcgcacacgcgccgg
cgcctgcccttgcggcgcaccgccatcagctgctataaaagggcggcacaccgggtctgagtagtcgtcatcaacgacagcccc
agacaacactcaccgatagcaagtagcgccgccgacgtttcgagagcagagtatccaagctagccaagcgcgcacctcggtgac
ctagctagttcaggcgacgatATG**

Figure 5

```
tcctcctgctccctcctacctctggtggaccatcgaccgcgcccggctccggtgcctgcaccgcacgcc
acatgcggccgatgggcagcggaagctagcagcccggcttgaatgacctatattatatgaagaagatgcc
tcagatgctactcgactacaaggtttatgtttctcaggtgactaaatagatcatgtgctgatgttagcga
ttcttgtgtggaagtgaattcatgccaatttgaagccaatatggtttaggtgtatttttttactggattta
ggttgaaggtcaatttgtcttcttttttattctgcaaatacacattgacaacctaatgactttctattgtt
ttaatatcagaccaataaacctttttctttttttaatatgctatgaactgtatcagctttgtgacctct
tgtttccatttcccttggattcatataattaactttcgacaccagagcaatacatctgtcatcaattat
taacataatatgttatgtcttgcttggtttagcctcaagaggttttatgcatgttcttttgtattgcttg
gggtgttaactttttttatccatttggtgtgggtgagggtgggatctgttattcctgatgtaatgcataa
tccattcattatgatcatagtaggaatatggctacactgactctttcttcctcagtggagtacaattggt
ggcctatatacttgatgtgggcgtcatttttacgattgcctctgaatgtgggagtagtcttatggtaat
aaaagtcaaacaattctaatgtgttgtgctagatctaaattaccttgaagacattgttgggggttccaat
gtcactgttgacatcatatccaaatttgtatccttctgtatggtgtgatatatctagaagctctaagaat
ttttgtcttgtgcaggtcctgtaattaatgaatgatttgaaccaaagtgttcgaggtactgttctcttgt
attgaggttagttaattccatatttgatactctataggcctactttagttgacattttgattttttccac
acccataatgactggtgtgatatctatttccattgatcttgttcaatttcccaatagttacatcctacat
ttacaacctggagagattgaagcattttttatagcaacatctgaactattaaaactcaccgtttgctccac
cacgggcttaggttcttcgacctctctatgaatcccctaagataccagaactgttgtagtggttatata
tattgagtatctgtttgaattgtaagaccttgtgatatttccagaagatttgtataagtctgtaatttgt
tgtgataatattagcatctaaatgatgcaattgatataacattattaaaatcataaatagaagtttgcat
ggtaccgatggttgcaatgtagtggtgaaataactatattaaaataacaaaatgtatgtatggctagcta
ggatttataaaatcttttcttataacacatatttgtatataaattatcatgatattatatgttcccgtt
gcaacgcacgggcacttatatatatatgtgtgtgttttttttttcacatgtacccatcagataggatg
ataagagaggttaaatcatgccttaaggaacatcttaagaagtgtttttacatgctacattttggtggat
tttatataaccgttttttacatacatacggccctatatatatcatagttcagtttgattcctccgttaca
aaccaactaaatgcatagaccacgcggaccgaaagcaacagggtcgatgagtcgaagcagcggggccgat
gaagtcgaagcggtctcctgaacgcagatgcacgtcggcgatcgggatggctgggatggcgacgcagttg
tgagtagaggcgaaaacttaatttgtgttgggattgacactaggcgccttatatagggccgtgtccacga
accgataacgatgcgcgatccgatctacacgttatccacgaatcgatagactcgcgttccgttcatatcc
ttatcggatcggttagggctctaaaattaacagccaagcaacagcctcggcccggcgaggcgagcgcgt
gtggttctccacactctctcctctcatccatgacttggtgagtgagcgtagcatccatatttaaactagt
tccactccacttgaactagcaatatgacactatttgtttccaccattctctagccataccatacatgcgct
tttgagatttttttaggatttaattgaatttctcaattgggcctatcccataaatccaacacgatataag
tctatctgtcgctggtagattgagagatgatgtgtgcatgtctgtaaataaaaaaaattgcttttacaca
taaattgcgctatgactttacatgaaataaatttttctaaaatttaaaacttacataagtaaaaaaaatat
aaagaaggaagaaacacgacatggaaaaaaatctctcgttgttttatatggaggcaacggctgcagtcc
ccgtgcaagcgatgctcatccgttcccatggcgtgcacggcccagaaacgacacgcttcacctacttctt
ccctgccaccacacccaccgtccacccacaccacaccgcgcgccacgcgcccacggcacctcggcacagt
gtcgtcgcatgtcgctcacgtactgtcgcagaactcacaccgtcacacggtgcctgctatctagctaatg
ctgctagcagccatgtcacaccgatataacccggccaccgcgcgccgcgccacgtcgccatgcacgcggc
cacgtccccgatcgatcgacgtcgtcctcctcatcctggctcctccattcccgcgcttcataaatacct
cggccatgtacatcgacccagccatctcctcaccctcgttcaccacacagcccgccactcctttagtagc
ttgtgatttgtacgtcgacgagatcactggttggcggacgacgacccatg
```

Figure 10
A. E1
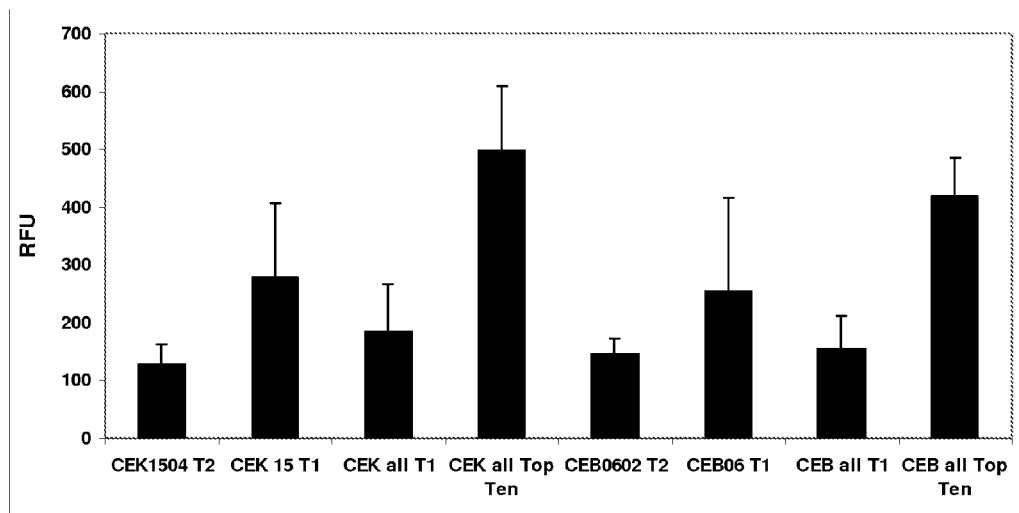
B. CBHI
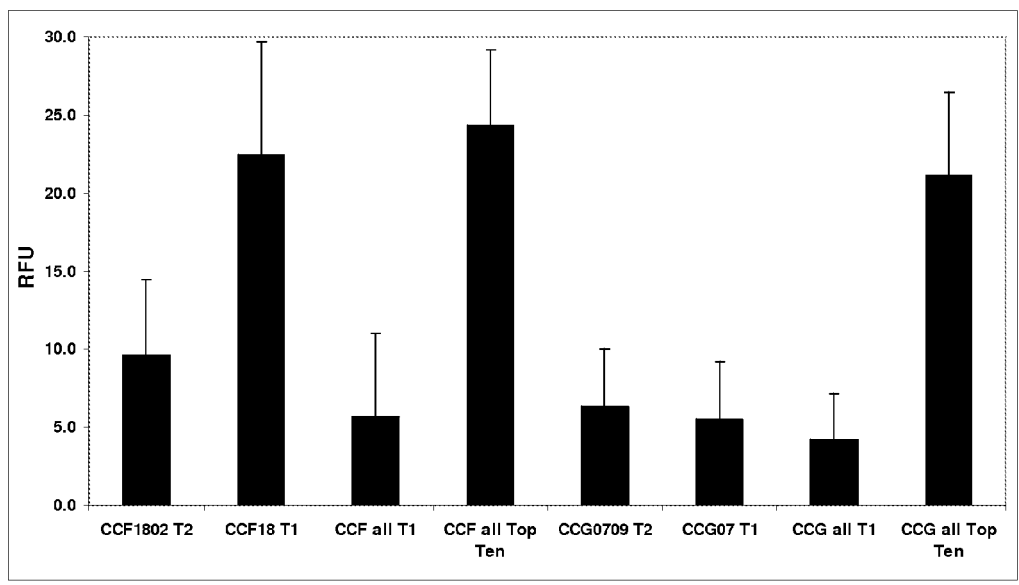

```
      ATGGCCAAC AAGCACCTGA GCCTCTCCCT CTTCCTCGTG CTCCTCGGCC
 51   TCTCCGCCTC CCTCGCCAGC GGCGAGTCCA CCACCTCCGG CTTCCTCGGC
101   CCGCTCCTCG TGCTCCAGGC CGGCTTCTCC CTCCTCACCC GCATCCTCAC
151   CATCCCGCAG TCCCTCGACT CCTGGTGGAC CTCCCTCAAC TTCCTCGGCG
201   GCGCCCCGAC CTGCCCGGGC CAGAACCTCC AGTCCCCGAC CTCCAACCAC
251   TCCCCGACCT CCTGCCCGCC CACCTGCCCG GCTACCGCT GGATGTGCCT
301   CCGCCGCTTC ATCATCTTCC TCTTCATCCT CCTGCTCTGC CTCATCTTCC
351   TCCTCGTGCT CGTGGACTAC CAGGGCATGC TCCCGGTGTG CCCGCTCCTC
401   CCGGGCACCT CCACGACCTC CACCGGCCCG TGCAAGACCT GCACCATCCC
451   GGCCCAGGGC ACCTCCATGT TCCCGTCCTG CTGCTGCACC AAGCCGTCCG
501   ACGGCAACTG CGCCTGCATC CCGATCCCGT CCTCCTGGGC CTTCGCCCGC
551   TTCCTCTGGG AGTGGGCCTC CGTGCGCTTC TCCTGGCTCT CCCTCCTCGT
601   GCCGTTCGTG CAGTGGTTCG TGGGCCTCTC CCCGACCGTG TGGCTCTCCG
651   TGATCTGGAT GATGTGGTAC TGGGGCCCGT CCCTCTACAA CATCCTCTCC
701   CCGTTCCTCC CGCTCCTCCC GATCTTCTTC TGCCTCTGGG TGTACATCTG
751   A
```

E1 cellulase gene sequence

GCCGGCGGTGGCTACTGGCACACCAGCGGCAGGGAGATCCTGGACGCCAAC
AATGTGCCGGTGAGGATCGCCGGCATCAACTGGTTTGGGTTCGAAACCTGCA
ATTACGTCGTGCACGGTCTCTGGTCACGCGACTACCGCAGCATGCTCGACCA
GATAAAGTCGCTCGGCTACAACACAATCCGGCTGCCGTACTCTGACGACATT
CTCAAGCCGGGCACCATGCCGAACAGCATCAATTTTTACCAGATGAATCAGG
ACCTGCAGGGTCTGACGTCCTTGCAGGTCATGGACAAAATCGTCGCGTACGC
CGGTCAGATCGGCCTGCGCATCATTCTTGACCGCCACCGACCGGATTGCAGC
GGGCAGTCGGCGCTGTGGTACACGAGCAGCGTCTCGGAGGCTACGTGGATTT
CCGACCTGCAAGCGCTGGCGCAGCGCTACAAGGGAAACCCGACGGTCGTCG
GCTTTGACTTGCACAACGAGCCGCATGACCCGGCCTGCTGGGGCTGCGGCGA
TCCGAGCATCGACTGGCGATTGGCCGCCGAGCGGGCCGGAAACGCCGTGCTC
TCGGTGAATCCGAACCTGCTCATTTTCGTCGAAGGTGTGCAGAGCTACAACG
GAGACTCCTACTGGTGGGGCGGCAACCTGCAAGGAGCCGGCCAGTACCCGGT
CGTGCTGAACGTGCCGAACCGCCTGGTGTACTCGGCGCACGACTACGCGACG
AGCGTCTACCCGCAGACGTGGTTCAGCGATCCGACCTTCCCCAACAACATGC
CCGGCATCTGGAACAAGAACTGGGGATACCTCTTCAATCAGAACATTGCACC
GGTATGGCTGGGCGAATTCGGTACGACACTGCAATCCACGACCGACCAGACG
TGGCTGAAGACGCTCGTCCAGTACCTACGGCCGACCGCGCAATACGGTGCGG
ACAGCTTCCAGTGGACCTTCTGGTCCTGGAACCCCGATTCCGGCGACACAGG
AGGAATTCTCAAGGATGACTGGCAGACGGTCGACACAGTAAAAGACGGCTAT
CTCGCGCCGATCAAGTCGTCGATTTTCGATCCTGTCGGCGCGTCTGCATCGCC
TAGCAGTCAACCGTCCCCGTCGGTGTCGCCGTCTCCGTCGCCGAGCCCGTCGG
CGAGTCGGACGCCGACGCCTACTCCGACGCCGACAGCCAGCCCGACGCCAAC
GCTGACCCCTACTGCTACGCCCACGCCCACGGCAAGCCCGACGCCGTCACCG
ACGGCAGCCTCCGGAGCCCGCTGCACCGCGAGTTACCAGGTCAACAGCGATT
GGGGCAATGGCTTCACGGTAACGGTGGCCGTGACAAATTCCGGATCCGTCGC
GACCAAGACATGGACGGTCAGTTGGACATTCGGCGGAAATCAGACGATTACC
AATTCGTGGAATGCAGCGGTCACGCAGAACGGTCAGTCGGTAACGGCTCGGA
ATATGAGTTATAACAACGTGATTCAGCCTGGTCAGAACACCACGTTCGGATT
CCAGGCGAGCTATACCGGAAGCAACGCGGCACCGACAGTCGCCTGCGCAGC
AAGTTAA

Figure 15

CBHI gene sequence

CAGAGCGCCTGCACCCTGCAGAGCGAGACCCACCCGCCACTGACCTGGCAGA
AATGCTCGTCTGGTGGCACGTGCACTCAACAGACAGGCTCCGTGGTCATCGA
CGCCAACTGGCGCTGGACTCACGCTACGAACAGCAGCACGAACTGCTACGAT
GGCAACACTTGGAGCTCGACCCTATGTCCTGACAACGAGACCTGCGCGAAGA
ACTGCTGTCTGGACGGTGCCGCCTACGCGTCCACGTACGGAGTTACCACGAG
CGGTAACAGCCTCTCCATTGGCTTTGTCACCCAGTCTGCGCAGAAGAACGTTG
GCGCTCGCCTTTACCTTATGGCGAGCGACACGACCTACCAGGAATTCACCCT
GCTTGGCAACGAGTTCTCTTTCGATGTTGATGTTTCGCAGCTGCCGTGCGGCT
TGAACGGAGCTCTCTACTTCGTGTCCATGGACGCGGATGGTGGCGTGAGCAA
GTATCCCACCAACACCGCTGGCGCCAAGTACGGCACGGGGTACTGTGACAGC
CAGTGTCCCCGCGATCTGAAGTTCATCAATGGCCAGGCCAACGTTGAGGGCT
GGGAGCCGTCATCCAACAACGCGAACACGGGCATTGGAGGACACGGAAGCT
GCTGCTCTGAGATGGATATCTGGGAGGCCAACTCCATCTCCGAGGCTCTTACC
CCCCACCCTTGCACGACTGTCGGCCAGGAGATCTGCGAGGGTGATGGGTGCG
GCGGAACTTACTCCGATAACAGATATGGCGGCACTTGCGATCCCGATGGCTG
CGACTGGAACCCATACCGCCTGGGCAACACCAGCTTCTACGGCCCTGGCTCA
AGCTTTACCCTCGATACCACCAAGAAATTGACCGTTGTCACCCAGTTCGAGA
CGTCGGGTGCCATCAACCGATACTATGTCCAGAATGGCGTCACTTTCCAGCA
GCCCAACGCCGAGCTTGGTAGTTACTCTGGCAACGAGCTCAACGATGACTAC
TGCACAGCTGAGGAGGCAGAATTCGGCGGATCCTCTTTCTCAGACAAGGGCG
GCCTGACTCAGTTCAAGAAGGCTACCTCTGGCGGCATGGTTCTGGTCATGAGT
CTGTGGGATGACTACTACGCCAACATGCTGTGGCTGGACTCCACCTACCCGA
CAAACGAGACCTCCTCCACACCCGGTGCCGTGCGCGGAAGCTGCTCCACCAG
CTCCGGTGTCCCTGCTCAGGTCGAATCTCAGTCTCCCAACGCCAAGGTCACCT
TCTCCAACATCAAGTTCGGACCCATTGGCAGCACCGGCAACCCTAGCGGCGG
CAACCCTCCCGGCGGAAACCCGCCTGGCACCACCACCACCCGCCGCCCAGCC
ACTACCACTGGAAGCTCTCCCGGACCTACCCAGTCTCACTACGGCCAGTGCG
GCGGTATTGGCTACAGCGGCCCCACGGTCTGCGCCAGCGGCACAACTTGCCA
GGTCCTGAACCCTTACTACTCTCAGTGCCTGTAA

SEQUENCE LISTING

```
<160> NUMBER OF SEQ ID NOS: 21

<210> SEQ ID NO 1
<211> LENGTH: 1401
<212> TYPE: DNA
<213> ORGANISM: Zea mays

<400> SEQUENCE: 1
aagcttgccg agtgccatcc ttggacactc gataaagtat attttatttt ttttattttg      60
ccaaccaaac tttttgtggt atgttcctac actatgtaga tctacatgta ccattttggc     120
acaattacat atttacaaaa atgttttcta taaatattag atttagttcg tttatttgaa     180
tttcttcgga aaattcacat ttaaactgca agtcactcga aacatggaaa accgtgcatg     240
caaaataaat gatatgcatg ttatctagca caagttacga ccgatttcag aagcagacca     300
gaatcttcaa gcaccatgct cactaaacat gaccgtgaac ttgttatcta gttgtttaaa     360
aattgtataa aacacaaata aagtcagaaa ttaatgaaac ttgtccacat gtcatgatat     420
catatataga ggttgtgata aaaatttgat aatgtttcgg taaagttgtg acgtactatg     480
tgtagaaacc taagtgacct acacataaaa tcatagagtt tcaatgtagt tcactcgaca     540
aagactttgt caagtgtccg ataaaaagta ctcgacaaag aagccgttgt cgatgtactg     600
ttcgtcgaga tctctttgtc gagtgtcaca ctaggcaaag tctttacgga gtgttttca     660 ggctttgaca ctcggcaaag cgctcgattc cagtagtgac agtaatttgc atcaaaaata     720
gctgagagat ttaggccccg tttcaatctc acgggataaa gtttagcttc ctgctaaact     780
ttagctatat gaattgaagt gctaaagttt agtttcaatt accaccatta gctctcctgt     840
ttagattaca aatggctaaa agtagctaaa aaatagctgc taaagtttat ctcgcgagat     900
tgaaacaggg ccttaaaatg agtcaactaa tagaccaact aattattagc tattagtcgt     960
```

```
tagcttctttt aatctaagct aaaaccaact aatagcttat ttgttgaatt acaattagct    1020
caacggaatt ctctgttttt ctaaaaaaaa actgcccctc tcttacagca aattgtccgc    1080
tgcccgtcgt ccagatacaa tgaacgtacc tagtaggaac tcttttacac gctcggtcgc    1140
tcgccgcgga tcggagtccc cggaacacga caccactgtg gaacacgaca aagtctgctc    1200
agaggcggcc acaccctggc gtgcaccgag ccggagcccg ataagcacg gtaaggagag     1260 tacggcggga cgtggcgacc cgtgtgtctg ctgccacgca gccttcctcc acgtagccgc    1320
gcggccgcgc cacgtaccag ggcccggcgc tggtataaat gcgcgccacc tccgctttag    1380
ttctgcatac agccaaccca a                                              1401

<210> SEQ ID NO 2
<211> LENGTH: 1386
<212> TYPE: DNA
<213> ORGANISM: Zea mays

<400> SEQUENCE: 2
aagcttgccg agtgccatcc ttggacactc gataaagtat atttatttt ttttattttg     60 ccaaccaaac ttttttgtggt atgttcctac actatgtaga tctacatgta ccattttggc   120
acaattacat atttacaaaa atgttttcta taaatattag atttagttcg tttatttgaa    180
tttcttcgga aaattcacat ttaaactgca agtcactcga acatggaaa accgtgcatg     240 caaaataaat gatatgcatg ttatctagca caagttacga ccgatttcag aagcagacca    300
gaatcttcaa gcaccatgct cactaaacat gaccgtgaac ttgttatcta gttgtttaaa   360
aattgtataa aacacaaata aagtcagaaa ttaatgaaac ttgtccacat gtcatgatat    420
catatataga ggttgtgata aaaatttgat aatgtttcgg taaagttgtg acgtactatg    480
tgtagaaacc taagtgaccct acacataaaa tcatagagtt tcaatgtagt tcactcgaca   540
aagactttgt caagtgtccg ataaaaagta ctcgacaaag aagccgttgt cgatgtactg    600
ttcgtcgaga tctctttgtc gagtgtcaca ctaggcaaag tctttacgga gtgttttttca   660 ggctttgaca ctcggcaaag cgctcgattc cagtagtgac agtaatttgc atcaaaaata    720
gctgagagat ttaggccccg tttcaatctc acgggataaa gtttagcttc ctgctaaact    780
ttagctatat gaattgaagt gctaaagttt agtttcaatt accaccatta gctctcctgt    840
ttagattaca aatggctaaa agtagctaaa aaatagctgc taaagtttat ctcgcgagat    900
tgaaacaggg ccttaaaatg agtcaactaa tagaccaact aattattagc tattagtcgt    960 tagcttctttt aatctaagct aaaaccaact aatagcttat ttgttgaatt acaattagct   1020
caacggaatt ctctgttttt ctaaaaaaaa actgcccctc tcttacagca aattgtccgc    1080
tgcccgtcgt ccagatacaa tgaacgtacc tagtaggaac tcttttacac gctcggtcgc    1140
tcgccgcgga tcggagtccc cggaacacga caccactgtg gaacacgaca aagtctgctc    1200
agaggcggcc acaccctggc gtgcaccgag ccggagcccg ataagcacg gtaaggagag     1260 tacggcggga cgtggcgacc cgtgtgtctg ctgccacgca gccttcctcc acgtagccgc    1320
gcggccgcgc cacgtaccag ggcccggcgc tggtataaat gcgcgccacc tccgctttag    1380
ttctgc                                                               1386

<210> SEQ ID NO 3
<211> LENGTH: 15
<212> TYPE: DNA
<213> ORGANISM: Zea mays

<400> SEQUENCE: 3
```

```
atacagccaa cccaa                                                    15

<210> SEQ ID NO 4
<211> LENGTH: 43
<212> TYPE: DNA
<213> ORGANISM: Zea mays

<400> SEQUENCE: 4
ggatccaaca cacacccgag gatatcacag tcgacactac acc                     43

<210> SEQ ID NO 5
<211> LENGTH: 3006
<212> TYPE: DNA
<213> ORGANISM: Zea mays

<400> SEQUENCE: 5
cggtatgaat ttggaaacaa attcagtact tttaaaaaaa tttgttgtag ggagcaaata   60
atacataaaa taatttatgc attattttat tttttatttg taataatatg cttgaaacga  120
taattcagta tgcatgttgt gccagtgtac tacacgggcg gggggagggg attgagtggg  180
ccagcgcggt gcgtagggta gatgggctga aattgataac tcaagtccga ctaggttctc  240
tttttatttc ccttcctttt ctattttcct ttcttttaat tttcatgctt tcaaactaaa  300
ttcaaattcg agttttgaat ttcagcttct aaattgtaca ctaaaattat atgataaggt  360
aaccctact attacttta atttttttat tctacccat attgtttact taggggagaa   420
taattgactt aatcacattc ttcctaggtt tcaattctca atctttcaaa tccacatttt  480
tagatttcta ttttgaattt aaataccagt ttggatttag agttcaattt caaaatacac  540
aaccaaaata ccagcatgaa tgcaaatata ttttatgttt atgtatttac ttttcttta   600
tactttgctc aaaatagtta ttttcatgta tgaaactcaa taagcaagga actcacgtta  660
ttatataacc taataggaat aatttaggta acataattta tcatcctctt gatttaaaag  720
agatatgcct ccagaataag acacatacta aaaataactc taatattgaa taactaaagt  780
cgtacaaatc tctactatta ttcctataaa ataataaaga actagctaca acttctttaa  840
ggcattattc agggtttaca gcttgagagg catgaaccca tcctgtatac tcctggactt  900
ggaagacaaa atgtcaacca agtgaaaagg ttttcttatg gttgctgcta agagatagat  960
tgaacactag atctctccta agacgtcagg gcatgcgttt agactcctac acatgcgaaa 1020
actgcatctt acagttggaa gaaactatat ctcaccactt cctgcggtgt aactttgccc 1080
aaagatgttg gctcactgtt ggaatcactc cgccccgaac tttggatcta acgcttgcag 1140
tgctacatat tagagcaaga ctaacaatgc cgtggagaat ggaaggtatt ataaccatgt 1200
catggtgcat atgaaaatgt cgaaataact ggatattcga aaacataccg ccaacggtgg 1260
cggcctgcaa ggaaatgttc aagactgaaa tgaactacat ctgctaccaa gttaagctcg 1320
agacaggagc taaaagtaga aactggatac aacactttgt aacatagtga cactcccctt 1380
ttccttcctt ttaccttaga actatacata caatccacat tcaataaaaa tttgtaggta 1440
cgccatacac actaccggaa tccggctctt tgccgagtgt gaggcgcttt gtcgagtgct 1500
ttttgtccag cactcggcaa aaaagtcttt gccatgtgcc gcactcggca aagtcctgct 1560
ctcggtaacg accgcgttta ccgagagcag gactctcgac acagaaatac actcgacaaa 1620
gaaatctttg ccgagagcca aacactcggc gaacggcagc gctcggcaaa gggtcgtcag 1680
ccgccgtcta aagctgacgg tcgttatctt tgtcgagtgc ccctcgtcc gacactcagt  1740
```

```
agagcaagct tgccgagtgc catccttgga cactcgataa agtatatttt attttttttt   1800
attttgccaa ccaaacttt tgtggtatgt tcctacacta tgtagatcta catgtaccat    1860
tttggcacaa ttacaaaaat gttttctata actattagat ttagttcgtt tatttgaatt   1920
tcttcggaaa attcacatat gaactgcaag tcactcgaaa catgaaaaac cgtgcatgca   1980
aaataaatga tatgcatgtt atctagcaca agttacgacc gaattcagaa gcagaccaga   2040
atcttcaagc accatgctca ctaaacatga ccgtgaactt gttatccagt tgtttaaaaa   2100
ttgtataaaa cacaaataaa gtcagaaatt aatgaaactt gtccacatgt catgatatca   2160
tatatagagg ttgtgataaa aatttgataa tgtttcggta agttgtgac gtactatgtg    2220
tagaaaccta agtgacctac acataaaatc atagagtttc aatgtagttc actcgacaaa   2280
gactttgtca agtgtccgat aaaaagtatt cagcaaagaa gccgttgtcg atttactgtt   2340
cgtcgagatc tctttgccga gtgtcacact aggcaaagtc tttacggagt gttttttcagg  2400
ctttgacact cggcaaagcg ctcgattcca gtagtgacag taatttgcat caaaaatagc   2460
cgagagattt aaaatgagtc aactaataga ccaactaatt attagctatt agtcgttagc   2520
ttctttaatc taagctaaaa ccaactaata gcttatttgt tgaattacaa ttagctcaac   2580
ggaattctct gtttttcta taaaaaaag ggaaactgcc cctcatttac agcaaactgt    2640
ccgctgcctg tcgtccagat acaatgaacg tacctagtag gaactctttt acacgctcgg   2700
tcgctcgccg cggatcggag tcccaggaac acgacaccac tgtggaacac gacaaagtct   2760
gctcagaggc ggccacaccc tggcgtgcac cgagccggag cccggataag cacggtaagg   2820
agagtacggc gggacgtggc gacccgtgtg tctgctgcca cgcagccttc ctccacgtag   2880
ccgcgcggcc gcgccacgta ccagggcccg gcgctggtat aaatgcgcgc cacctccgct   2940
ttagttctgc atacagccaa cccaacacac acccgagcat atcacagtga cagacactac   3000
acgatg                                                              3006

<210> SEQ ID NO 6
<211> LENGTH: 53
<212> TYPE: DNA
<213> ORGANISM: Zea mays

<400> SEQUENCE: 6
atacagccaa cccaacacac acccgagcat atcacagtga cagacactac acg           53

<210> SEQ ID NO 7
<211> LENGTH: 2950
<212> TYPE: DNA
<213> ORGANISM: Zea mays

<400> SEQUENCE: 7
cggtatgaat ttggaaacaa attcagtact tttaaaaaaa tttgttgtag ggagcaaata    60
atacataaaa taattatgc attatttat tttttatttg taataatatg cttgaaacga    120
taattcagta tgcatgttgt gccagtgtac tacacgggcg gggggagggg attgagtggg   180
ccagcgcggt gcgtagggta gatgggctga aattgataac tcaagtccga ctaggttctc   240
tttttatttc ccttccttt ctattttcct ttcttttaat tttcatgctt tcaaactaaa   300
ttcaaattcg agttttgaat ttcagcttct aaattgtaca ctaaaattat atgataaggt   360
aaccccctact attactttta atttttttat tctaccccat attgtttact taggggagaa  420
taattgactt aatcacattc ttcctaggtt tcaattctca atctttcaaa tccacatttt   480
tagatttcta ttttgaattt aaataccagt ttggatttag agttcaattt caaaatacac   540
```

```
aaccaaaata ccagcatgaa tgcaaatata ttttatgttt atgtatttac ttttctttta      600
tactttgctc aaaatagtta ttttcatgta tgaaactcaa taagcaagga actcacgtta      660
ttatataacc taataggaat aatttaggta acataattta tcatcctctt gatttaaaag      720
agatatgcct ccagaataag acacatacta aaaataactc taatattgaa taactaaagt      780
cgtacaaatc tctactatta ttcctataaa ataataaaga actagctaca acttctttaa      840
ggcattattc agggtttaca gcttgagagg catgaaccca tcctgtatac tcctggactt      900
ggaagacaaa atgtcaacca aagtgaaagg ttttcttatg gttgctgcta agagatagat      960
tgaacactag atctctccta agacgtcagg gcatgcgttt agactcctac acatgcgaaa     1020
actgcatctt acagttggaa gaaactatat ctcaccactt cctgcggtgt aactttgccc     1080
aaagatgttg gctcactgtt ggaatcactc cgccccgaac tttggatcta acgcttgcag     1140
tgctacatat tagagcaaga ctaacaatgc cgtggagaat ggaaggtatt ataaccatgt     1200
catggtgcat atggaaatgt cgaaataact ggatattcga aaacataccg ccaacggtgg     1260
cggcctgcaa ggaaatgttc aagactgaaa tgaactacat ctgctaccaa gttaagctcg     1320
agacaggagc taaagtagaa aactggatac aacactttgt aacatagtga cactcccctt     1380
ttcctttctt ttaccttaga actatacata caatccacat tcaataaaaa tttgtaggta     1440
cgccatacac actaccggaa tccggctctt gccgagtgt gaggcgcttt gtcgagtgct     1500
ttttgtccag cactcggcaa aaagtctttt gccatgtgcc gcactcggca aagtcctgct     1560
ctcggtaacg accgcgttta ccgagagcag gactctcgac acagaaatac actcgacaaa     1620
gaaatctttg ccgagagcca aacactcggc gaacggcagc gctcggcaaa gggtcgtcag     1680
ccgccgtcta aagctgacgg tcgttatctt tgtcgagtgc cccctcgtcc gacactcagt     1740
agagcaagct tgccgagtgc catccttgga cactcgataa agtatatttt atttttttt     1800 attttgccaa ccaaactttt tgtggtatgt tcctacacta tgtagatcta catgtaccat     1860
tttggcacaa ttacaaaaat gttttctata actattagat ttagttcgtt tatttgaatt     1920
tcttcggaaa attcacatat gaactgcaag tcactcgaaa catgaaaaac cgtgcatgca     1980
aaataaatga tatgcatgtt atctagcaca agttacgacc gaattcagaa gcagaccaga     2040
atcttcaagc accatgctca ctaaacatga ccgtgaactt gttatccagt tgtttaaaaa     2100
ttgtataaaa cacaaataaa gtcagaaatt aatgaaactt gtccacatgt catgatatca     2160
tatatagagg ttgtgataaa aatttgataa tgtttcggta agttgtgac gtactatgtg      2220 tagaaaccta agtgacctac acataaaatc atagagtttc aatgtagttc actcgacaaa     2280
gactttgtca agtgtccgat aaaagtatt cagcaaagaa gccgttgtcg atttactgtt     2340
cgtcgagatc tctttgccga gtgtcacact aggcaaagtc tttacggagt gtttttcagg     2400
ctttgacact cggcaaagcg ctcgattcca gtagtgacag taatttgcat caaaaatagc     2460
cgagagattt aaaatgagtc aactaataga ccaactaatt attagctatt agtcgttagc     2520
ttctttaatc taagctaaaa ccaactaata gcttatttgt tgaattacaa ttagctcaac     2580
ggaattctct gttttttcta taaaaaaaag ggaaactgcc cctcatttac agcaaactgt     2640
ccgctgcctg tcgtccagat acaatgaacg tacctagtag gaactctttt acacgctcgg     2700
tcgctcgccg cggatcggag tcccaggaac acgacaccac tgtggaacac gacaaagtct     2760
gctcagaggc ggccacaccc tggcgtgcac cgagccggag cccggataag cacggtaagg     2820
agagtacggc gggacgtggc gacccgtgtg tctgctgcca cgcagccttc ctccacgtag     2880
```

```
ccgcgcggcc gcgccacgta ccagggcccg gcgctggtat aaatgcgcgc cacctccgct    2940
ttagttctgc                                                          2950

<210> SEQ ID NO 8
<211> LENGTH: 3004
<212> TYPE: DNA
<213> ORGANISM: Zea mays

<400> SEQUENCE: 8
gcgatctgaa gatctggtga acctgagcct gacccatcaa atgtctataa gttttctttg      60
tagagaaatt atcggctccc caaatgagtt tccaagcatc atttgtattg gccaccatga     120
tttggcccca agttgcgtct aagtctagaa attgttcata agcttgcacc gacagaggta     180
gctgaaaaat ttcaataagt tgttcctttt ggagagcttc tttgatggta agtttgctgt     240
tgcaagcaaa ggaaaataac tcaggatatt gatgagccgg gatgccccta ttccacatat     300
cttcccagaa aagaatggtt cttccatccc cgatagttgg ggcagccagt cccttgtaat     360
cttggacaag agtaagcaag cttttccacc aaaaggagcc aattttttga gcaaccaggta     420 gcctgactgt cctgtaatag ttgctccaaa ccaggttaac ccagggaata tcatgattgt     480
tgaaaaactt gtgcaaaaac ttcagaagca aggctttatt gtgagtctct aatcttacca     540
ctcccaggcc cccattttt tagtctgtgt aatcatactc caagtagcta gagcaggttt     600
ctttgaattg acgtcgtttc ctctccaaag acagtgtttc cgataagaat caatcttctt     660
taccgtggta accggaattt tcagtgtgca catcaaaaag gtcgggagag ctgagaacac     720
cgagttaaca agctcaagcc tgccagcctg ggagaggagg gcagaggtgc atgataatct     780
cttttgaatc ctatgaatga gcggtaaaaa gtggcagatt ttaggctttg atagaccaag     840
cggaacacca agataggtaa agggcattga acctatctga cagttgaggg ttcctgctag     900
gatcgccatt ttagcaggac tgacattgat ggggtacata cttgatttgt tgtaattcac     960
cttcaacccc gtcgaagttg caaagagtt cagaacggct ctgagaaaaa atagctgtct    1020
agggcaagct tccattatca gtagtgtgtc atccgcatat tgaactatcg gaaaatcttg    1080
accacaattc tcggccaggg gtaacttgag aaggtcttgc tgccgcgctt tattgatgat    1140
gctctgtaac agatccgccg cgagaacaaa agaagaggc gagaggggat ctccctgcct    1200
aaccccacgc ttgtagtgaa aggttttccc aggaacacca ttaagaagga ctgatgacgt    1260
gctagaccga agaatatccc taatccagct catccatctg ggcccaaagc ctctatgcaa    1320
cattacctga agaatcaact catgctcaag agaatcaaaa gccttttcaa atccaatttt    1380
gagcacaata atctcttttt ttgaaatatg acaaagatga atatattcaa atgcccaggc    1440
cagacaatcc tgaatggttc tttctttgat gaagccatat tgattttgt gaacaaggga    1500 agtcatcact gtctgtaacc ggttagccag cagcttagtg atgattttca tactattatt    1560
cagaagcgaa attggtctga aatcgcccac taaactagca ttatccttct tcggaatcag    1620
gacaatataa gaaccattga tgcttcgaag acaaatatcc ccgtggtaaa attggtcaca    1680
taagtcatag aagtcctggg aaataatcgg acaacatttt tttgataaag ttggtattaa    1740
acccatcagg tccgggggat ttatcagaag gaagggacgc cacaatacta tcaatttctt    1800
gctttgaaaa aggctcatct aaccaatgca agtcattgcg gcagagcaac aaactagaaa    1860
gatcaaagac attatccaca aaatcggagg atcccaagcg acatttgaac atattccaaa    1920
gcaggttagt tttgagatca tgctctgtaa agattgagcc actgtcatcc aagagcaacg    1980
caattgtatt acggccatgc cacgcaactg tcatccaaga actttctact cttggattac    2040
```

```
acggataaag ttgaagtact acaagcaact ataaacgact agagcctttg cttgagtcct    2100
tttatacgcg gtcgaagagt gtttgcctct ttatttattt gttcagcagg ccccgagaat    2160
cttcaccgct gaagcacacc cgacccgaat aattgataat attgctcaaa tcatatgaga    2220
tggacgctgg ctctgcagct tttagggcct gttcgtttga ctcggaattc atcccggaat    2280
tgttccagct aatcaaatgt tatataaatt agataaccaa tccggctagg aatagttccg    2340
gacggccaat tcctcagaat cgaacgggcc cttagctagt ttcgagtcgt cggaatcagc    2400
ttctgctagc taaatgtttt gcttttcata gtctattttt gttagaatcg tttatataaa    2460
aattacatct aaatatagaa tctatcgaat cgtcgtgata gtatgaatgt gatgctgcgc    2520
gtagactcct ttgtcttctt tagcacataa atcgtataaa aattgtcgta acagctattt    2580
tttaagaatc cagattatca gaaatctttg ggaaaaaaag cactctctga aaaagccccg    2640
cgtcgctacg tgcagctcca tctgctccgt gttgtcccca tcccaatcac cgctgtcgct    2700
tcgccgcagg catcccagca gcgagctagc atgcacgcac gcacgcaagc acacggcggc    2760
agctgcacgg atgcggccga gtgcggtagc actgcagcgc gcgcgcgcgc tccacatcgc    2820
cttcgccccg ccacgtacgc ggcccggcct ccacctggcg gcgcgcatgg ctgcgaccct    2880
cgccgcgcca cctcttcata tacgccgcag ctcgcttcga accctcgcat cgaacgcaca    2940
ctcgcactcg cagtcgcacg tacacggtac accacactag ctaccacaga cgacgagcgc    3000
catg                                                                3004

<210> SEQ ID NO 9
<211> LENGTH: 48
<212> TYPE: DNA
<213> ORGANISM: Zea mays

<400> SEQUENCE: 9
tcgcacgtac acggtacacc acactagcta ccacagacga cgagcgcc                  48

<210> SEQ ID NO 10
<211> LENGTH: 2953
<212> TYPE: DNA
<213> ORGANISM: Zea mays

<400> SEQUENCE: 10
gcgatctgaa gatctggtga acctgagcct gacccatcaa atgtctataa gttttctttg      60
tagagaaatt atcggctccc caaatgagtt ccaagcatc atttgtattg gccaccatga     120
tttggcccca agttgcgtct aagtctagaa attgttcata agcttgcacc gacagaggta     180
gctgaaaaat ttcaataagt tgttccttt ggagagcttc tttgatggta agtttgctgt      240
tgcaagcaaa ggaaaataac tcaggatatt gatgagccgg gatgccccta ttccacatat     300
cttcccagaa aagaatggtt cttccatccc cgatagttgg ggcagccagt cccttgtaat     360
cttggacaag agtaagcaag cttttccacc aaaaggagcc aattttttgag caaccaggta     420 gcctgactgt cctgtaatag ttgctccaaa ccaggttaac ccagggaata tcatgattgt     480
tgaaaaactt gtgcaaaaac ttcagaagca aggctttatt gtgagtctct aatcttacca     540
ctcccaggcc cccatttttt tagtctgtgt aatcatactc caagtagcta gagcaggttt     600
ctttgaattg acgtcgtttc ctctccaaag acagtgtttc cgataagaat caatcttctt     660
taccgtggta accggaattt tcagtgtgca catcaaaaag gtcgggagag ctgagaacac     720
cgagttaaca agctcaagcc tgccagcctg ggagaggagg gcagaggtgc atgataatct     780
```

```
cttttgaatc ctatgaatga gcggtaaaaa gtggcagatt ttaggctttg atagaccaag    840
cggaacacca agataggtaa agggcattga acctatctga cagttgaggg ttcctgctag    900
gatcgccatt ttagcaggac tgacattgat ggggtacata cttgatttgt tgtaattcac    960
cttcaacccc gtcgaagttg caaaagagtt cagaacggct ctgagaaaaa atagctgtct   1020
agggcaagct tccattatca gtagtgtgtc atccgcatat tgaactatcg gaaaatcttg   1080
accacaattc tcggccaggg gtaacttgag aaggtcttgc tgccgcgctt tattgatgat   1140
gctctgtaac agatccgccg cgagaacaaa agaagaggc gagagggat ctccctgcct    1200 aaccccacgc ttgtagtgaa aggttttccc aggaacacca ttaagaagga ctgatgacgt   1260
gctagaccga agaatatccc taatccagct catccatctg ggcccaaagc ctctatgcaa   1320
cattacctga agaatcaact catgctcaag agaatcaaaa gccttttcaa aatccaattt   1380
gagcacaata atctcttttt ttgaaatatg acaaagatga atatattcaa atgcccaggc   1440
cagacaatcc tgaatggttc tttctttgat gaagccatat tgattttttgt gaacaaggga   1500 agtcatcact gtctgtaacc ggttagccag cagcttagtg atgattttca tactattatt   1560
cagaagcgaa attggtctga aatcgcccac taaactagca ttatccttct tcggaatcag   1620
gacaatataa gaaccattga tgcttcgaag acaaatatcc ccgtggtaaa attggtcaca   1680
taagtcatag aagtcctggg aaataatcgg acaacatttt tttgataaag ttggtattaa   1740
acccatcagg tcccggggat ttatcagaag gaagggacgc cacaatacta tcaatttctt   1800
gctttgaaaa aggctcatct aaccaatgca agtcattgcg gcagagcaac aaactagaaa   1860
gatcaaagac attatccaca aaatcggagg atcccaagcg acatttgaac atattccaaa   1920
gcaggttagt tttgagatca tgctctgtaa agattgagcc actgtcatcc aagagcaacg   1980
caattgtatt acgccatgc cacgcaactg tcatccaaga actttctact cttggattac    2040
acggataaag ttgaagtact acaagcaact ataaacgact agagcctttg cttgagtcct   2100
tttatacgcg gtcgaagagt gttttgcctct ttatttattt gttcagcagg ccccgagaat   2160
cttcaccgct gaagcacacc cgacccgaat aattgataat attgctcaaa tcatatgaga   2220
tggacgctgg ctctgcagct tttagggcct gttcgtttga ctcggaattc atcccggaat   2280
tgttccagct aatcaaatgt tatataaatt agataaccaa tccggctagg aatagttccg   2340
gacggccaat tcctcagaat cgaacgggcc cttagctagt ttcgagtcgt cggaatcagc   2400
ttctgctagc taaatgtttt gcttttcata gtctattttt gttagaatcg tttatataaa   2460
aattacatct aaatatagaa tctatcgaat cgtcgtgata gtatgaatgt gatgctgcgc   2520
gtagactcct ttgtcttctt tagcacataa atcgtataaa aattgtcgta acagctattt   2580
tttaagaatc cagattatca gaaatctttg ggaaaaaaag cactctctga aaaagccccg   2640
cgtcgctacg tgcagctcca tctgctccgt gttgtcccca tcccaatcac cgctgtcgct   2700
tcgccgcagg catcccagca gcgagctagc atgcacgcac gcacgcaagc acacggcggc   2760
agctgcacgg atgcggccga gtgcggtagc actgcagcgc gcgcgcgcgc tccacatcgc   2820
cttcgccccg ccacgtacgc ggcccggcct ccacctggcg gcgcgcatgg ctgcgaccct   2880
cgccgcgcca cctcttcata tacgccgcag ctcgcttcga accctcgcat cgaacgcaca   2940
ctcgcactcg cag                                                      2953
```

<210> SEQ ID NO 11
<211> LENGTH: 2999
<212> TYPE: DNA
<213> ORGANISM: Zea mays

<400> SEQUENCE: 11

```
cttcaattcc tgtgtgttgt attactactg atacaatctc caattcttgt gaacttatgt        60
atttggactt gtgtgaattt gtgatatgaa catatatcca tgtgtttgaa atctgtactg       120
tatgtgatat tttgtgttgc atgtgatatt atgtttgtct aattttttat ttctgtattt       180
tttattttt  ctagaaaagg gttaagaacg tgagtaccca cgttcttaac gttaagaacg       240
tgggtaccgt cgaacttatt gtgcagacct cgcagaccca cgcaggacac ataaggtcga       300
cggccacgtg gccccgtcga acttaaccgt aagaacgtgg gtgccgtcga acttatggga       360
aaaaattcga cggccccgtc gaacttaaaa acgcacgctc ttaatgttaa gttcgacggt       420
acccacgttc ttaatgttaa gttcgacggt acccacattc ttacttctct aagttcgtcc       480
aaaaatcgct gtcggctata ttcgtcggta aacccacgtt cttacggtaa gttcgacggc       540
ttattacatt aagttcgacg gttttcacc  cacgttcttt aaccagtttc ctgtagtgta       600
tatgttggta acctcgtact tagatgagca atatgcacta ccagaatcac gttctttgcc       660
gactgtctaa gatactcacc aaaagtcatt ttacactcgg caaataatac tcgtcaaaca       720
ttttatcggc aaaggattct tgccgagta  cttttttgga cactcggcaa agactttgcc       780
gagtgtcgaa aagcactcgg caaattaaga atcggaagcc cccaaaaaac atcattttt       840
ttaaattata ggaacaactc tccaaccact agtcattatc atatccaggt gatattcgaa       900
ctcgcaacat ctctctcgcg catacccctcc tctaccacta cactactaca tcaattatgt       960
ctatattacg ttttcattcc tcatgtacta taacaaatcg agagtaattt tattatttaa      1020
ggcactaaat gaattcattt gaaaatgtga ccaactataa agttgcataa cttttcgaga      1080
catataagtt ctattttgat agtttccaca tacgagacca tttacaaaat ttgaattcaa      1140
atttgaaaac ttcacgcgaa ttttttcaatg ataagatgat ttcaaatcaa aaaattgtca      1200
attacaaagt ttcattacat ttcaagacct acaactttta tattggtgtt ttttccatcc      1260
gaggtagttt gaaaattcaa atttcaaaat tcaaacatag ttttgcatga caatatgatt      1320
tcaaaccaaa acattgtcaa ctacaaagtt tcataactc  ttcaataccct acaactttca      1380
tgttggtggt tttttctttc ggggtcgttt tgaaaattca aatttttaaat attttaaatt      1440
cagacgtagt tttcgttgat aaaatgactt caaataaaaa agttgtcaac tataaaaatg      1500
tgtaacttct caaaatctat aaaatttatt ttggttgttt ggtcatttgt tcatctcaca      1560
ttatggttct aacaatatgc acaaatctta tacatctctc tcgtagtttc ataaactacg      1620
agagatatat gttttatgaa caaatttatt tttattttgt tatataaaga aatattcaaa      1680
atataaattg tacatcatga tgagttatac aaatttatag ttgaaaattt tttcatttaa      1740
attaattttac tgcttaaaat gtgattttta aattgtcctt acatagtgtt gaaaaaagca      1800
ctcggcaaaa aagctctttg ccgagtgttt tattttttgac actcggcaaa atgcttcttt      1860
atcgagtgta aaaaaatact cgacaagtgt caaaaataaa acactcggca aagagcttct      1920
ttgccgagtg ttttgtttta ccgagggttt ttgcgtgaca ctcgataaag agcttgtttg      1980
ctgagttccg aaaaaaacac tcgacgaaat atttagcatt cgacgaagag ccaaattta      2040
ttagtgatga gactaaaaaa ctgtttagtt cgtggctaat tatattatac tttatttaag      2100
gttggttgtt gtaatcgaag aactaacgtt agatataggg cccctttggt agggcttatt      2160
tttcagcttc ggctctggct catgcaaaag ttatgccaaa cacctctttt tcaaatggct      2220
tcaccaatga agtgcttttt caaaatgaac tagagggcat gagccaaaaa aagtggctca      2280
```

```
cccggcttca gctcacgtca ttttttgcaca atagccctcc caccagtcca aattattttt    2340
ttggtcctgc cctcaatccc tagccacgca aatagccct cccaccagtc caaactatac    2400
aagggtcttt ctgaaaaata acctataagc cgttttgcca aatgaatttt cagaatggct    2460
ttggctcatc taaagaagtg gcttcacctc gtgagccaga gccaaagccg ttttggaga    2520 agccagagcc ctgccaaagg gcccataat aagccgtaga accaaacaat cccgaagctc    2580
accagctact cactctagag tcctgctcct gccacagtgc cagttgcgcc tcacgcagcc    2640
acgcaggaat aggataagca ctatactacg cacgctctgg cttccgcttc gtagatgcat    2700
gcgtgtcgcc gccggaggct ctcgccgcgc acgcgtcgcg cgctgcggtg gtaacgactt    2760
cacggggtgt cccagcgtag cgtccgcgtc ggcgcacacg cgccggcgcc tgcccttgcg    2820
gcgcaccgcc catcagctgc tataaaaggg cggcacaccg ggtctgagta gtcgtcatca    2880
acgacagccc cagacaacac tcaccgatag caagtagcgc cgccgacgtt tcgagagcag    2940
agtatccaag ctagccaagc gcgcacctcg gtgacctagc tagttcaggc gacgatatg    2999

<210> SEQ ID NO 12
<211> LENGTH: 239
<212> TYPE: DNA
<213> ORGANISM: Zea mays

<400> SEQUENCE: 12
cttcacgggg tgtcccagcg tagcgtccgc gtcggcgcac acgcgccggc gcctgcccttt    60 gcggcgcacc gcccatcagc tgctataaaa gggcggcaca ccgggtctga gtagtcgtca    120
tcaacgacag ccccagacaa cactcaccga tagcaagtag cgccgccgac gtttcgagag    180
cagagtatcc aagctagcca agcgcgcacc tcggtgacct agctagttca ggcgacgat    239

<210> SEQ ID NO 13
<211> LENGTH: 2757
<212> TYPE: DNA
<213> ORGANISM: Zea mays

<400> SEQUENCE: 13
cttcaattcc tgtgtgttgt attactactg atacaatctc caattcttgt gaacttatgt    60
atttggactt gtgtgaattt gtgatatgaa catatatcca tgtgtttgaa atctgtactg    120
tatgtgatat tttgtgttgc atgtgatatt atgtttgtct aatttttat ttctgtattt    180 tttattttt ctagaaaagg gttaagaacg tgagtaccca cgttcttaac gttaagaacg    240
tgggtaccgt cgaacttatt gtgcagacct cgcagaccca cgcaggacac ataaggtcga    300
cggccacgtg gccccgtcga acttaaccgt aagaacgtgg gtgccgtcga acttatggga    360
aaaaattcga cggccccgtc gaacttaaaa acgcacgctc ttaatgttaa gttcgacggt    420
acccacgttc ttaatgttaa gttcgacggt acccacattc ttacttctct aagttcgtcc    480
aaaaatcgct gtcggctata ttcgtcggta aacccacgtt cttacggtaa gttcgacggc    540
ttattacatt aagttcgacg gttttcacc cacgttcttt aaccagttc ctgtagtgta    600 tatgttggta acctcgtact tagatgagca atatgcacta ccagaatcac gttctttgcc    660
gactgtctaa gatactcacc aaaagtcatt ttacactcgg caaataatac tcgtcaaaca    720
ttttatcggc aaaggattct ttgccgagta cttttttgga cactcggcaa agactttgcc    780
gagtgtcgaa aagcactcgg caaattaaga atcggaagcc cccaaaaaac atcattttt    840 ttaaattata ggaacaactc tccaaccact agtcattatc atatccaggt gatattcgaa    900
ctcgcaacat ctctctcgcg catacccttcc tctaccacta cactactaca tcaattatgt    960
```

```
ctatattacg ttttcattcc tcatgtacta taacaaatcg agagtaattt tattatttaa    1020
ggcactaaat gaattcattt gaaaatgtga ccaactataa agttgcataa cttttcgaga    1080
catataagtt ctattttgat agtttccaca tacgagacca tttacaaaat ttgaattcaa    1140
atttgaaaac ttcacgcgaa ttttcaatg ataagatgat ttcaaatcaa aaaattgtca     1200
attacaaagt ttcattacat ttcaagacct acaactttta tattggtgtt ttttccatcc    1260
gaggtagttt gaaaattcaa atttcaaaat tcaaacatag ttttgcatga caatatgatt    1320
tcaaaccaaa acattgtcaa ctacaaagtt ttcataactc ttcaatacct acaactttca    1380
tgttggtggt ttttcttc ggggtcgttt tgaaaattca aattttaaat attttaaatt      1440
cagacgtagt tttcgttgat aaaatgactt caaataaaaa agttgtcaac tataaaaatg    1500
tgtaacttct caaaatctat aaaatttatt ttggttgttt ggtcatttgt tcatctcaca    1560
ttatggttct aacaatatgc acaaatctta tacatctctc tcgtagtttc ataaactacg    1620
agagatatat gttttatgaa caaatttatt tttatttgt tatataaaga aatattcaaa     1680
atataaattg tacatcatga tgagttatac aaatttatag ttgaaaattt tttcatttaa    1740
attaatttac tgcttaaaat gtgatttta aattgtcctt acatagtgtt gaaaaaagca     1800
ctcggcaaaa aagctctttg ccgagtgttt tattttgac actcggcaaa atgcttcttt     1860
atcgagtgta aaaaatact cgacaagtgt caaaaataaa acactcggca aagagcttct     1920
ttgccgagtg ttttgtttta ccgagggttt ttgcgtgaca ctcgataaag agcttgtttg    1980
ctgagttccg aaaaaaacac tcgacgaaat atttagcatt cgacgaagag ccaaattta     2040 ttagtgatga gactaaaaaa ctgtttagtt cgtggctaat tatattatac tttatttaag    2100
gttggttgtt gtaatcgaag aactaacgtt agatataggg ccccttggt agggcttatt     2160 tttcagcttc ggctctggct catgcaaaag ttatgccaaa cacctctttt tcaaatggct    2220
tcaccaatga agtgctttt caaaatgaac tagagggcat gagccaaaaa aagtggctca     2280
cccggcttca gctcacgtca tttttgcaca atagccctcc caccagtcca aattatttt     2340 ttggtcctgc cctcaatccc tagccacgca caatagccct cccaccagtc caaactatac    2400
aagggtcttt ctgaaaaata acctataagc cgttttgcca aatgaatttt cagaatggct    2460
ttggctcatc taaagaagtg gcttcacctc gtgagccaga gccaaagccg ttttgggaga    2520
agccagagcc ctgccaaagg gcccataat aagccgtaga accaaacaat cccgaagctc     2580
accagctact cactctagag tcctgctcct gccacagtgc cagttgcgcc tcacgcagcc    2640
acgcaggaat aggataagca ctatactacg cacgctctgg cttccgcttc gtagatgcat    2700
gcgtgtcgcc gccggaggct ctcgccgcgc acgcgtcgcg cgctgcggtg gtaacga       2757
```

<210> SEQ ID NO 14
<211> LENGTH: 2990
<212> TYPE: DNA
<213> ORGANISM: Zea mays

<400> SEQUENCE: 14

```
tcctcctgct cccctcctac ctctggtgga ccatcgaccg cgcccggctc cggtgcctgc      60
accgcacgcc acatgcggcc gatgggcagc ggaagctagc agcccggctt gaatgaccta     120
tattatatga agaagatgcc tcagatgcta ctcgactaca aggtttatgt ttctcaggtg     180
actaaataga tcatgtgctg atgttagcga ttccttgtgt gaagtgaatt catgccaatt     240
tgaagccaat atggtttagg tgtattttt actggattta ggttgaaggt caatttgtct      300
```

```
tcttttatt  ctgcaaatac  acattgacaa  cctaatgact  ttctattgtt  ttaatatcag    360
accaataaac  cttttttctt  ttttaatat   gctatgaact  gtatcagctt  tgtgacctct    420
tgtttccatt  tccccttgga  ttcatataat  taactttcga  caccagagca  atacatctgt    480
catcaattat  taacataata  tgttatgtct  tgcttggttt  agcctcaaga  ggttttatgc    540
atgttctttt  gtattgcttg  gggtgttaac  ttttttatc   catttggtgt  gggtgagggt    600
gggatctgtt  attcctgatg  taatgcataa  tccattcatt  atgatcatag  taggaatatg    660
gctacactga  ctcttctcc   ctcagtggag  tacaattggt  ggccttatat  acttgatgtg    720
ggcgtcattt  ttacgattgc  ctctgaatgt  gggagtagtc  ttatggtaat  aaaagtcaaa    780
caattctaat  gtgttgtgct  agatctaaat  taccttgaag  acattgttgg  gggttccaat    840
gtcactgttg  acatcatatc  caaatttgta  tccttctgta  tggtgtgata  tatctagaag    900
ctctaagaat  ttttgtcttg  tgcaggtcct  gtaattaatg  aatgatttga  accaaagtgt    960
tcgaggtact  gttctcttgt  attgaggtta  gttaattcca  tatttgatac  tctataggcc   1020
tactttagtt  gacatttga   ttttttccac  acccataatg  actggtgtga  tatctatttc   1080
cattgatctt  gttcaatttc  ccaatagtta  catcctacat  ttacaacctg  gagagattga   1140 agcatttta   tagcaacatc  tgaactatta  aaactcaccg  tttgctccac  cacgggctta   1200
ggttcttcga  cctctctatg  aatcccccta  agataccaga  actgttgtag  tggttatata   1260
tattgagtat  ctgtttgaat  tgtaagacct  tgtgatattt  ccagaagatt  tgtataagtc   1320
tgtaatttgt  tgtgataata  ttagcatcta  aatgatgcaa  ttgatataac  attattaaaa   1380
tcataaatag  aagtttgcat  ggtaccgatg  gttgcaatgt  agtggtgaaa  taactatatt   1440
aaaataacaa  aatgtatgta  tggctagcta  ggatttataa  aatcttttc   ttataacaca   1500 tatttgtata  taaattatca  tgatattata  tgttcccgtt  gcaacgcacg  ggcacttata   1560
tatatatatg  tgtgtgtttt  tttttcaca   tgtacccatc  agataggatg  ataagagagg   1620
ttaaatcatg  ccttaaggaa  catcttaaga  agtgttttta  catgctacat  tttggtggat   1680
tttatataac  cgttttttac  atacatacgg  ccctatatat  atcatagttc  agtttgattc   1740
ctccgttaca  aaccaactaa  atgcatagac  cacgcggacc  gaaagcaaca  gggtcgatga   1800
gtcgaagcag  cggggccgat  gaagtcgaag  cggtctcctg  aacgcagatg  cacgtcggcg   1860
atcgggatgg  ctgggatggc  gacgcagttg  tgagtagagg  cgaaaactta  atttgtgttg   1920
ggattgacac  taggcgcctt  atatagggcc  gtgtccacga  accgataacg  atgcgcgatc   1980
cgatctacac  gttatccacg  aatcgataga  ctcgcgttcc  gttcatatcc  ttatcgggat   2040
cggttagggc  tctaaaatta  acagccaagc  aacagcctcg  gcccggcgag  gcgagcgcgt   2100
gtggttctcc  acactctctc  ctctcatcca  tgcttggtg   agtgagcgta  gcatccatat   2160
ttaaactagt  tccactccac  ttgaactagc  aatatgacac  tatttgtttc  accattctct   2220
agccatacca  tacatgcgct  tttgagattt  tttaggatt   taattgaatt  tctcaattgg   2280
gcctatccca  taaatccaac  acgatataag  tctatctgtc  gctggtagat  tgagagatga   2340
tgtgtgcatg  tctgtaaata  aaaaaaattg  cttttacaca  taaattgcgc  tatgacttta   2400
catgaaataa  attttctaaa  atttaaaact  tacataagta  aaaaaaatat  aaagaaggaa   2460
gaaacacgac  atggaaaaaa  aatctctcgt  tgttttatat  ggaggcaacg  gctgcagtcc   2520
ccgtgcaagc  gatgctcatc  cgttcccatg  gcgtgcacgg  cccagaaacg  acacgcttca   2580
cctacttctt  ccctgccacc  acacccaccg  tccacccaca  ccacaccgcg  cgccacgcgc   2640
ccacggcacc  tcggcacagt  gtcgtcgcat  gtcgctcacg  tactgtcgca  gaactcacac   2700
```

```
cgtcacacgg tgcctgctat ctagctaatg ctgctagcag ccatgtcaca ccgatataac    2760
ccggccaccg cgcgccgcgc cacgtcgcca tgcacgcggc cacgtccccg atcgatcgac    2820
gtcgtcctcc tcatcctggc tcctccattc ccgcgcttct ataaatacct cggccatgta    2880
catcgaccca gccatctcct caccctcgtt caccacacag cccgccactc ctttagtagc    2940
ttgtgatttg tacgtcgacg agatcactgg ttggcggacg acgacccatg              2990

<210> SEQ ID NO 15
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atggcccacg cccgcgtcct cctcctggcg ctcgccgtcc tggccacggc cgccgtcgcc    60
gtcgcctcct cctcctcctt cgccgactcc aacccgatcc ggccggtcac cgaccgcgcc    120
gcgtccacc                                                           129

<210> SEQ ID NO 16
<211> LENGTH: 750
<212> TYPE: DNA
<213> ORGANISM: Hepatitis b virus

<400> SEQUENCE: 16
atggccaaca agcacctgag cctctcccte ttcctcgtgc tcctcggcct ctccgcctcc    60
ctcgccagcg gcgagtccac cacctccggc ttcctcggcc cgctcctcgt gctccaggcc    120
ggcttctccc tcctcacccg catcctcacc atcccgcagt ccctcgactc ctggtggacc    180
tccctcaact tcctcggcgg cgccccgacc tgcccgggcc agaacctcca gtccccgacc    240
tccaaccact ccccgacctc ctgcccgccc acctgcccgg ctaccgctg gatgtgcctc    300 cgccgcttca tcatcttcct cttcatcctc ctgctctgcc tcatcttcct cctcgtgctc    360
gtggactacc agggcatgct cccggtgtgc ccgctcctcc cgggcacctc cacgacctcc    420
accggcccgt gcaagacctg caccatcccg gcccagggca cctccatgtt cccgtcctgc    480
tgctgcacca gccgtccga cggcaactgc gcctgcatcc cgatcccgtc ctcctgggcc    540
ttcgcccgct tcctctggga gtgggcctcc gtgcgcttct cctggctctc cctcctcgtg    600
ccgttcgtgc agtggttcgt gggcctctcc ccgaccgtgt ggctctccgt gatctggatg    660
atgtggtact ggggcccgtc cctctacaac atcctctccc cgttcctccc gctcctcccg    720
atcttcttct gcctctgggt gtacatctga                                    750

<210> SEQ ID NO 17
<211> LENGTH: 72
<212> TYPE: DNA
<213> ORGANISM: Hepatitis b virus

<400> SEQUENCE: 17
atggccaaca agcacctgag cctctcccte ttcctcgtgc tcctcggcct ctccgcctcc    60
ctcgccagcg gc                                                       72

<210> SEQ ID NO 18
<211> LENGTH: 1566
<212> TYPE: DNA
<213> ORGANISM: Acidothermus cellulolyticus
```

<400> SEQUENCE: 18

```
gccggcggtg gctactggca caccagcggc agggagatcc tggacgccaa caatgtgccg      60
gtgaggatcg ccggcatcaa ctggtttggg ttcgaaacct gcaattacgt cgtgcacggt     120
ctctggtcac gcgactaccg cagcatgctc gaccagataa agtcgctcgg ctacaacaca     180
atccggctgc cgtactctga cgacattctc aagccgggca ccatgccgaa cagcatcaat     240
ttttaccaga tgaatcagga cctgcagggt ctgacgtcct gcaggtcat ggacaaaatc      300
gtcgcgtacg ccggtcagat cggcctgcgc atcattcttg accgccaccg accggattgc     360
agcgggcagt cggcgctgtg gtacacgagc agcgtctcgg aggctacgtg gatttccgac     420
ctgcaagcgc tggcgcagcg ctacaaggga acccgacgg tcgtcggctt tgacttgcac      480
aacgagccgc atgaccccgg ctgctggggc tgcggcgatc cgagcatcga ctggcgattg     540
gccgccgagc gggccggaaa cgccgtgctc tcggtgaatc cgaacctgct cattttcgtc     600
gaaggtgtgc agagctacaa cggagactcc tactggtggg cggcaacct gcaaggagcc      660
ggccagtacc cggtcgtgct gaacgtgccg aaccgcctgg tgtactcggc gcacgactac     720
gcgacgagcc tctacccgca gacgtggttc agcgatccga ccttcccaa caacatgccc      780
ggcatctgga caagaactg gggatacctc ttcaatcaga acattgcacc ggtatggctg      840
ggcgaattcg gtacgacact gcaatccacg accgaccaga cgtggctgaa gacgctcgtc     900
cagtacctac ggccgaccgc gcaatacggt gcggacagct tccagtggac cttctggtcc     960
tggaaccccg attccggcga cacaggagga attctcaagg atgactgca gacggtcgac      1020
acagtaaaag acggctatct cgcgccgatc aagtcgtcga ttttcgatcc tgtcggcgcg     1080
tctgcatcgc ctagcagtca accgtccccg tcggtgtcgc cgtctccgtc gccgagcccg     1140
tcggcgagtc ggacgccgac gcctactccg acgccgacag ccagcccgac gccaacgctg     1200
acccctactg ctacgcccac gcccacggca agcccgacgc cgtcaccgac ggcagcctcc     1260
ggagcccgct gcaccgcgag ttaccaggtc aacagcgatt ggggcaatgg cttcacggta     1320
acggtggccg tgacaaattc cggatccgtc gcgaccaaga catggacggt cagttggaca     1380
ttcggcggaa atcagacgat taccaattcg tggaatgcag cggtcacgca gaacggtcag     1440
tcggtaacgg ctcggaatat gagttataac aacgtgattc agcctggtca gaacaccacg     1500
ttcggattcc aggcgagcta taccggaagc aacgcggcac cgacagtcgc ctgcgcagca     1560
agttaa                                                                 1566
```

<210> SEQ ID NO 19
<211> LENGTH: 1494
<212> TYPE: DNA
<213> ORGANISM: Trichoderma viride

<400> SEQUENCE: 19

```
cagagcgcct gcaccctgca gagcgagacc caccgccac tgacctggca gaaatgctcg       60
tctggtggca cgtgcactca acagacaggc tccgtggtca tcgacgccaa ctggcgctgg     120
actcacgcta cgaacagcag cacgaactgc tacgatggca acacttggag ctcgacccta     180
tgtcctgaca acgagacctg cgcgaagaac tgctgtctgg acggtgccgc ctacgcgtcc     240
acgtacggag ttaccacgag cggtaacagc ctctccattg gctttgtcac ccagtctgcg     300
cagaagaacg ttggcgctcg cctttacctt atggcgagcg acacgaccta ccaggaattc     360
accctgcttg gcaacgagtt ctctttcgat gttgatgttt cgcagctgcc gtgcggcttg     420
```

```
aacggagctc tctacttcgt gtccatggac gcggatggtg gcgtgagcaa gtatcccacc      480
aacaccgctg cgccaagta cggcacgggg tactgtgaca gccagtgtcc ccgcgatctg      540
aagttcatca atggccaggc caacgttgag ggctgggagc cgtcatccaa caacgcgaac      600
acgggcattg gaggacacgg aagctgctgc tctgagatgg atatctggga ggccaactcc      660
atctccgagg ctcttacccc ccacccttgc acgactgtcg gccaggagat ctgcgagggt      720
gatgggtgcg gcggaactta ctccgataac agatatggcg gcacttgcga tcccgatggc      780
tgcgactgga acccataccg cctgggcaac accagcttct acggccctgg ctcaagcttt      840
accctcgata ccaccaagaa attgaccgtt gtcacccagt cgagacgtc gggtgccatc       900
aaccgatact atgtccagaa tggcgtcact ttccagcagc ccaacgccga gcttggtagt      960
tactctggca acgagctcaa cgatgactac tgcacagctg aggaggcaga attcggcgga     1020
tcctctttct cagacaaggg cggcctgact cagttcaaga aggctacctc tggcggcatg     1080
gttctggtca tgagtctgtg ggatgactac tacgccaaca tgctgtggct ggactccacc     1140
tacccgacaa acgagacctc ctccacaccc ggtgccgtgc gcggaagctg ctccaccagc     1200
tccggtgtcc ctgctcaggt cgaatctcag tctcccaacg ccaaggtcac cttctccaac     1260
atcaagttcg gacccattgg cagcaccggc aaccctagcg gcgcaaccc tcccggcgga      1320
aacccgcctg gcaccaccac cacccgccgc ccagccacta ccactggaag ctctcccgga     1380
cctacccagt ctcactacgg ccagtgcggc ggtattggct acagcggccc cacggtctgc     1440
gccagcggca aacttgcca ggtcctgaac ccttactact ctcagtgcct gtaa            1494

<210> SEQ ID NO 20
<211> LENGTH: 3003
<212> TYPE: DNA
<213> ORGANISM: Zea mays

<400> SEQUENCE: 20
gcgatctgaa gatctggtga acctgagcct gacccatcaa atgtctataa gtttctttg       60
tagagaaatt atcggctccc caaatgagtt tccaagcatc atttgtattg ccaccatga      120
tttggcccca agttgcgtct aagtctagaa attgttcata agcttgcacc gacagaggta     180
gctgaaaaat ttcaataagt tgttcctttt ggagagcttc tttgatggta agtttgctgt     240
tgcaagcaaa ggaaaataac tcaggatatt gatgagccgg atgccccat tccacatatc      300
ttcccagaaa agaatggttc ttccatcccc gatagttggg gcagccagtc ccttgtaatc     360
ttggacaaga gtaagcaagc ttttccacca aaaggagcca atttttgagc aaccaggtag     420
cctgactgtc ctgtaatagt tgctccaaac caggttaacc cagggaatat catgattgtt     480
gaaaaacttg tgcaaaaact tcagaagcaa ggctttattg tgagtctcta atcttaccac     540
tcccaggccc ccattttttt agtctgtgta atcatactcc aagtagctag agcaggtttc     600
tttgaattga cgtcgtttcc tctccaaaga cagtgtttcc gataagaatc aatcttcttt     660
accgtggtaa ccggaatttt cagtgtgcac atcaaaaagg tcgggagagc tgagaacacc     720
gagttaccaa gctcaagcct gccagcctgg gagaggaggg cagaggtgca tgataatctc     780
ttttgaatcc tatgaatgag cggtaaaaag tggcagattt taggctttga tagaccaagc     840
ggaacaccaa gataggtaaa gggcattgaa cctatctgac agttgagggt tcctgctagg     900
atcgccattt tagcaggact gacattgatg gggtacatac ttgatttgtt gtaattcacc     960
ttcaaccccg tcgaagttgc aaaagagttc agaacggctc tgagaaaaaa tagctgtcta    1020
gggcaagctt ccattatcag tagtgtgtca tccgcatatt gaactatcgg aaaatcttga    1080
```

```
ccacaattct cggccagggg taacttgaga aggtcttgct gccgcgcttt attgatgatg    1140
ctctgtaaca gatccgccgc gagaacaaaa agaagaggcg agaggggatc tccctgccta    1200
accccacgct tgtagtgaaa ggttttccca ggaacaccat taagaaggac tgatgacgtg    1260
ctagaccgaa gaatatccct aatccagctc atccatctgg gcccaaagcc tctatgcaac    1320
attacctgaa gaatcaactc atgctcaaga gaatcaaaag ccttttcaaa atccaatttg    1380
agcacaataa tctcttttt tgaaatatga caaagatgaa tatattcaaa tgcccaggcc    1440
agacaatcct gaatggttct ttctttgatg aagccatatt gattttgtg aacaagggaa     1500 gtcatcactg tctgtaaccg gttagccagc agcttagtga tgattttcat actattattc    1560
agaagcgaaa ttggtctgaa atcgcccact aaactagcat tatccttctt cggaatcagg    1620
acaatataag aaccattgat gcttcgaaga caaatatccc cgtggtaaaa ttggtcacat    1680
aagtcataga agtcctggga ataatcgga caacattttt ttgataaagt tggtattaaa     1740
cccatcaggt cccggggatt tatcagaagg aagggacgcc acaatactat caatttcttg    1800
ctttgaaaaa ggctcatcta accaatgcaa gtcattgcgg cagagcaaca aactagaaag    1860
atcaaagaca ttatccacaa aatcggagga tcccaagcga catttgaaca tattccaaag    1920
caggttagtt ttgagatcat gctctgtaaa gattgagcca ctgtcatcca agagcaacgc    1980
aattgtatta cggccatgcc acgcaactgt catccaagaa ctttctactc ttggattaca    2040
cggataaagt tgaagtacta caagcaacta taaacgacta gagcctttgc ttgagtcctt    2100
ttatacgcgg tcgaagagtg tttgcctctt tatttatttg ttcagcaggc cccgagaatc    2160
ttcaccgctg aagcacaccc gacccgaata attgataata ttgctcaaat catatgagat    2220
ggacgctggc tctgcagctt ttagggcctg ttcgtttgac tcggaattca tcccggaatt    2280
gttccagcta atcaaatgtt atataaatta gataaccaat ccggctagga atagttccgg    2340
acggccaatt cctcagaatc gaacgggccc ttagctagtt tcgagtcgtc ggaatcagct    2400
tctgctagct aaatgttttg ctttttcatag tctattttg ttagaatcgt ttatataaaa     2460
attacatcta aatatagaat ctatcgaatc gtcgtgatag tatgaatgtg atgctgcgcg    2520
tagactcctt tgtcttcttt agcacataaa tcgtataaaa attgtcgtaa cagctatttt    2580
ttaagaatcc agattatcag aaatctttgg gaaaaaaagc actctctgaa aaagccccgc    2640
gtcgctacgt gcagctccat ctgctccgtg ttgtccccat cccaatcacc gctgtcgctt    2700
cgccgcaggc atcccagcag cgagctagca tgcacgcacg cacgcaagca cacggcggca    2760
gctgcacgga tgcggccgag tgcggtagca ctgcagcgcg cgcgcgcgct ccacatcgcc    2820
ttcgccccgc cacgtacgcg gcccggcctc cacctggcgg cgcgcatggc tgcgaccctc    2880
gccgcgccac ctcttcatat acgccgcagc tcgcttcgaa ccctcgcatc gaacgcacac    2940
tcgcactcgc agtcgcacgt acacggtaca ccacactagc taccacagac gacgagcgcc    3000
atg                                                                 3003

<210> SEQ ID NO 21
<211> LENGTH: 2998
<212> TYPE: DNA
<213> ORGANISM: Zea mays

<400> SEQUENCE: 21
tcctcctgct cccctcctac ctctggtgga ccatcgaccg cgcccggctc cggtgcctgc     60
accgcacgcc acatgcggcc gatgggcagc ggaagctagc agcccggctt gaatgaccta    120
```

```
tattatatga agaagatgcc tcagatgcta ctcgactaca aggtttatgt ttctcaggtg      180
actaaataga tcatgtgctg atgttagcga ttcttgtgtg aagtgaatt catgccaatt       240 tgaagccaat atggtttagg tgtatttttt actggattta ggttgaaggt caatttgtct     300 tcttttatt ctgcaaatac acattgacaa cctaatgact ttctattgtt ttaatatcag      360
accaataaac ctttttttctt ttttaatat gctatgaact gtatcagctt tgtgacctct     420
tgtttccatt tccccttgga ttcatataat taactttcga caccagagca atacatctgt    480
catcaattat taacataata tgttatgtct tgcttggttt agcctcaaga ggttttatgc    540
atgttctttt gtattgcttg gggtgttaac ttttttttatc catttggtgt gggtgagggt   600
gggatctgtt attcctgatg taatgcataa tccattcatt atgatcatag taggaatatg   660
gctacactga ctcttctc ctcagtggag tacaattggt ggccttatat acttgatgtg       720
ggcgtcattt ttacgattgc ctctgaatgt gggagtagtc ttatggtaat aaaagtcaaa    780
caattctaat gtgttgtgct agatctaaat taccttgaag acattgttgg gggttccaat   840
gtcactgttg acatcatatc caaatttgta tccttctgta tggtgtgata tatctagaag   900
ctctaagaat ttttgtcttg tgcaggtcct gtaattaatg aatgatttga accaaagtgt   960
tcgaggtact gttctcttgt attgaggtta gttaattcca tatttgatac tctataggcc  1020
tactttagtt gacattttga tttttttccac acccataatg actggtgtga tatctatttc  1080
cattgatctt gttcaatttc ccaatagtta catcctacat ttacaacctg agagagttga  1140
agcattttta tagcaacatc tgaactatta aaactcaccg tttgctccac cacgggctta  1200
ggttcttcga cctctctatg aatcccccta agataccaga actgttgtag tggttatata  1260
tattgagtat ctgtttgaat tgtaagacct tgtgatattt ccagaagatt tgtataagtc  1320
tgtaatttgt tgtgataata ttagcatcta aatgatgcaa ttgatataac attattaaaa  1380
tcataaatag aagtttgcat ggtaccgatg gttgcaatgt agtggtgaaa taactatatt  1440
aaaataacaa aatgtatgta tggctagcta ggatttataa aatcttttttc ttataacaca 1500 tatttgtata taaattatca tgatattata tgttcccgtt gcaacgcacg ggcacttata  1560
tatatatatg tgtgtgtttt tttttttcaca tgtacccatc agataggatg ataagagagg 1620
ttaaatcatg ccttaaggaa catcttaaga agtgttttta catgctacat tttggtggat  1680
tttatataac cgtttttttac atacatacgg ccctatatat atcatagttc agtttgattc 1740
ctccgttaca aaccaactaa atgcatagac cacgcggacc gaaagcaaca gggtcgatga  1800
gtcgaagcag cggggccgat gaagtcgaag cggtctcctg aacgcagatg cacgtcggcg  1860
atcgggatgg ctgggatggc gacgcagttg tgagtagagg cgaaaactta atttgtgttg  1920
ggattgacac taggcgcctt atatagggcc gtgtccacga accgataacg atgcgcgatc  1980
cgatctacac gttatccacg aatcgataga ctcgcgttcc gttcatatcc ttatcgggat  2040
cggttagggc tctaaaatta acagccaagc aacagcctcg gcccggcgag gcgagcgcgt  2100
gtggttctcc acactctctc ctctcatcca tgacttggtg agtgagcgta gcatccatat  2160
ttaaactagt tccactccac ttgaactagc aatatgacac tatttgtttc accattctct  2220
agccatacca tacatgcgct tttgagattt ttttaggatt taattgaatt tctcaattgg  2280
gcctatccca taaatccaac acgatataag tctatctgtc gctggtagat tgagagatga  2340
tgtgtgcatg tctgtaaata aaaaaaattg cttttacaca taaattgcgc tatgacttta  2400
catgaaataa attttctaaa atttaaaact tacataagta aaaaaaatat aaagaaggaa  2460
gaaacacgac atggaaaaaa aatctctcgt tgttttatat ggaggcaacg gctgcagtcc  2520
```

```
ccgtgcaagc gatgctcatc cgttcccatg gcgtgcacgg cccagaaacg acacgcttca    2580
cctacttctt ccctgccacc acacccaccg tccacccaca ccacaccgcg cgccacgcgc    2640
ccacggcacc tcggcacagt gtcgtcgcat gtcgctcacg tactgtcgca gaactcacac    2700
cgtcacacgg tgcctgctat ctagctaatg ctgctagcag ccatgtcaca ccgatataac    2760
ccggccaccg cgcgccgcgc cacgtcgcca tgcacgcggc cacgtccccg atcgatcgac    2820
gtcgtcctcc tcatcctggc tcctccattc ccgcgcttct ataaatacct cggccatgta    2880
catcgaccca gccatctcct caccctcgtt caccacacag cccgccactc ctttagtagc    2940
ttgtgatttg tacgtcgacg agatcactgg ttggcggacg acgacccggg caaccatg     2998
```

METHOD OF INCREASING EXPRESSION OF NUCLEIC ACID MOLECULES IN PLANTS USING MULTIPLE TRANSCRIPTION UNITS

REFERENCE TO RELATED APPLICATION

This application claims priority to previously filed and co-pending application U.S. Ser. No. 61/549,343, filed Oct. 20, 2011, and is a continuation-in-part of previously filed and copending application U.S. Ser. No. 13/558,834 filed Jul. 26, 2012, which claims priority to U.S. Ser. No. 61/512,347 filed Jul. 27, 2011, the contents of each are incorporated herein by reference in its entirety.

STATEMENT REGARDING FEDERALLY SPONSORED RESEARCH OR DEVELOPMENT

This invention was made with government support under No. DOE DE FG36 GO88025 awarded by the United States Department of Energy. The government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 15, 2012, is named AB00016.txt and is 46,682 bytes in size.

BACKGROUND

Plants are a promising system for synthesis of foreign proteins due to their potential for low-cost high-volume production, ability to perform post-translational modifications, and lack of possible pathogen contamination. Many plant systems ranging from dicot model species such as tobacco and *Arabidopsis* to monocots including rice and maize have been used to express genes for disease resistance, enhanced nutrient quality, and production of pharmaceuticals and industrially valuable proteins (reviewed in Streatfield, 2007, Khan, 2010, Khan, in press). There has been a continued effort to increase and tightly regulate expression of proteins and products in plants.

BRIEF DESCRIPTION OF THE DRAWINGS

FIG. 1 shows the nucleotide sequence of the approximately 1.4 kb globulin-1 promoter (SEQ ID NO: 1) with the regulatory region at bases 1-1386 (SEQ ID NO: 2), the TATA box at bases 1354-1360 and the untranslated region at bases 1387-1401 shown in italics (SEQ ID NO: 3). An extra 43 bases appears in bold and below the sequence (SEQ ID NO: 4).

FIG. 2 shows the nucleotide sequence of the approximately 3 kb extended globulin-1 promoter (SEQ ID NO: 5) with the untranslated region in bold (SEQ ID NO: 6) and the translation start codon capitalized.

FIG. 3 shows the nucleotide sequence of the globulin-2 promoter (SEQ ID NO: 8) with the untranslated leader sequence in bold (SEQ ID NO: 9) and the translation start codon capitalized.

FIG. 4 shows the nucleotide sequences of the pr26 promoter (SEQ ID NO: 11) with the predicted untranslated leader in bold (SEQ ID NO: 12).

FIG. 5 shows the nucleotide sequence of the pr36 promoter (SEQ ID NO: 14) with the putative TATA box underlined and the ATG in bold.

FIGS. 10A and 10B are graphs showing expression in pooled $T_2$ seed compared to the average expression in $T_1$ seed for the same event, with 10A showing results for constructs CEK and CEB and 10B showing results from constructs CCF and CCG.

FIG. 11 shows the sequence of the optimized hepatitis B surface antigen nucleotide sequence (SEQ ID NO: 16) used in the experiments along with the Barley Alpha Amylase Signal Sequence (BAASS) (SEQ ID NO: 17) which is in italics with the ATG start codon and stop codon sites in bold.

FIG. 14 shows the E1 sequence (SEQ ID NO: 18) used in the experiments.

FIG. 15 shows the CBHI sequence (SEQ ID NO: 19) used in the experiments.

DESCRIPTION

Figure 6:
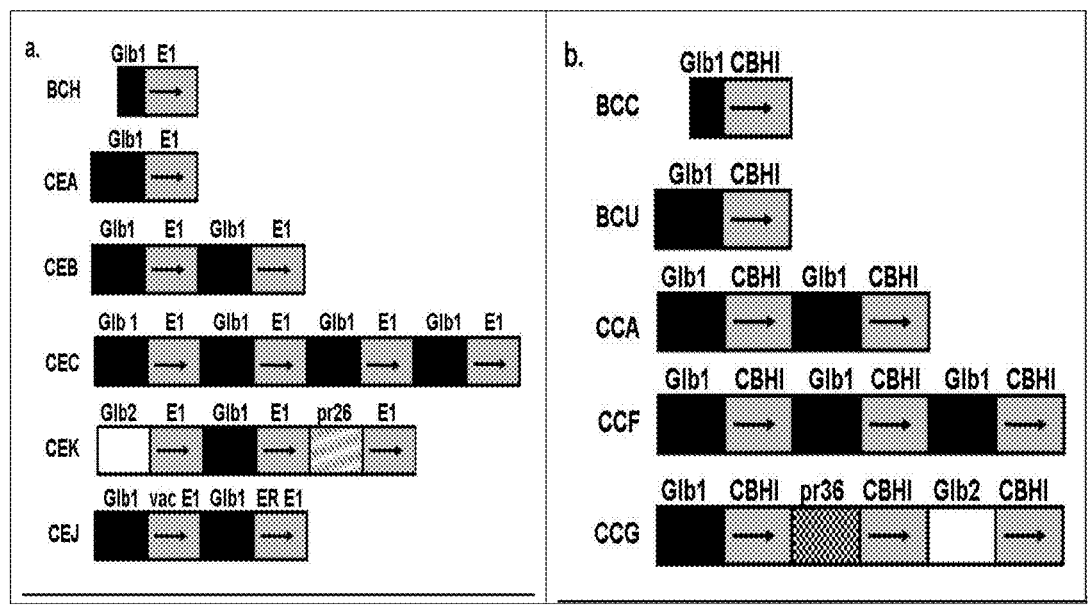
FIGS. 6A and 6B are graphic representations of constructs. Various combinations of (a) the E1 or (b) CBHI coding region under control of different promoters were prepared for expression in the maize embryo. Black, white, striped, or stippled blocks represents the globulin-1 (Glb1), the globulin-2 (Glb2), the pr26, or pr36 promoters, respectively. The gray blocks represent either the E1 or CBHI coding regions.

In order to express a nucleic acid molecule in a plant cell, a plant transcription unit (PTU) is provided which comprises at least a promoter and the nucleic acid molecule. When referring to a plant transcription unit is meant a promoter operably linked to a nucleic acid molecule and which can be introduced into a plant cell. The nucleic acid molecule (also referred to here as a "gene of interest") transcribes RNA to express a product. The promoter drives expression of the nucleic acid molecule and the product encoded by the nucleic acid molecule accumulates in the plant cell. In one embodiment the nucleic acid molecule expresses a polypeptide in the plant cell. The PTU may optionally include other PTU components, in addition to the promoter which drives the nucleic acid molecule of interest and the nucleic acid molecule of interest. These components may include any component of the vector (other than and in addition to the promoter driving the nucleic acid molecule of interest and the nucleic acid molecule of interest) useful in producing or enhancing production of the product encoded by the nucleic acid molecule. By the way of example, without limitation, such components may include an untranslated leader, a polyadenylation sequence, a signal sequence, an enhancer sequence, a selectable marker or the like. Examples are discussed further below. It will be evident to one skilled in the art many such non-promoter components may be used in a vector, depending upon the particular application.

Rather than suppressing expression, the inventors have found that use of multiple PTUs results in increased accumulation of product in the plant cells and in a plant compared to expression of a product and accumulation using one PTU. Here described in one embodiment is the use of multiple PTUs having the same promoter and same nucleic acid molecule expressing the product. Another embodiment is to a method using multiple PTUs where each PTU has a different promoter. The multiple PTUs may include at least two PTUs and in another embodiment may include two, three, four or more PTUs. In an embodiment, the other components may be the same for each PTU. This is particularly useful for reliable production of product from the nucleic acid molecule with multiple PTUs having different promoters.

The product may be any product encoded by the nucleic acid molecule. By way of example, in one embodiment the product expressed by the nucleic acid molecule may be selected from hepatitis B or aprotinin or a cellulase enzyme. The method is particularly useful when the product expressed is a cellulase enzyme, and in another embodiment may be endo-β-1,4-glucanase (E1) or exo-β-1,4-glucanase (CBH1). A still further embodiment provides that the PTU comprises a promoter comprising an embryo preferred promoter. One example provides the promoter is a globulin promoter. By way of example without limitation the promoter may be selected from SEQ ID NO: 1, SEQ ID NO: 3, SEQ ID NO: 5, SEQ ID NO: 7, SEQ ID NO: 8, SEQ ID NO: 10, SEQ ID NO: 11, SEQ ID NO: 13, SEQ ID NO: 14, SEQ ID NO: 20 or SEQ ID NO: 21.

Any plant-compatible promoter may be used in the methods disclosed. By "promoter" is meant a regulatory region of DNA capable of regulating the transcription of a sequence linked thereto. It usually comprises a TATA box capable of directing RNA polymerase II to initiate RNA synthesis at the appropriate transcription initiation site for a particular coding sequence. The promoter is the minimal sequence sufficient to direct transcription in a desired manner. The term "regulatory region" is also used to refer to the sequence capable of initiating transcription in a desired manner. A promoter can additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' region upstream from a promoter including any particular promoter region. Thus the promoter regions are generally further defined by comprising upstream regulatory elements such as those responsible for tissue and temporal expression of the coding sequence, enhancers and the like. In the same manner, the promoter elements which enable expression in the desired tissue such as the embryo can be identified, isolated, and used with other core promoters to confirm embryo-preferred expression. By core promoter is meant the sequence sometimes referred to as the TATA box (or similar sequence) which is common to promoters in all genes encoding proteins. Thus the upstream promoter can optionally be used in conjunction with its own or core promoters from other sources. The regulatory regions referred to herein may include the sequence which initiates transcription in the desired manner and may be linked with a TATA box or where an untranslated leader is used, may use an untranslated leader from another nucleic acid molecule, in addition to using the sequence natively associated with the regulatory region.

Various plant promoters are available to those skilled in the art. These can be plant gene promoters, such as, for example, the ubiquitin promoter (European patent application no. 0 342 926); the promoter for the small subunit of ribulose-1,5-bis-phosphate carboxylase (ssRUBISCO) (Coruzzi et al., 1984; Broglie et al., 1984); or promoters from the tumor-inducing plasmids from *Agrobacterium tumefaciens*, such as the nopaline synthase, octopine synthase and mannopine synthase promoters (Velten and Schell, 1985) that have plant activity; or viral promoters such as the cauliflower mosaic virus (CaMV) 19S and 35S promoters (Guilley et al., 1982; Odell et al., 1985), the figwort mosaic virus FLt promoter (Maiti et al., 1997) or the coat protein promoter of TMV (Grdzelishvili et al., 2000). Alternatively, plant promoters such as heat shock promoters for example soybean hsp 17.5-E (Gurley et al., 1986); or inducible promoters such as ethanol-inducible promoters (Caddick et al., 1998) may be used. Exemplary inducible promoters include ecdysone receptor promoters, U.S. Pat. No. 6,504,082; promoters from the ACE1 system which responds to copper (Mett et al. *PNAS* 90: 4567-4571 (1993)); In2-1 and In2-2 gene from maize which respond to benzenesulfonamide herbicide safeners (U.S. Pat. No. 5,364,780; Hershey et al., *Mol. Gen. Genetics* 227: 229-237 (1991) and Gatz et al., *Mol. Gen. Genetics* 243: 32-38 (1994)) Tet repressor from Tn10 (Gatz et al., *Mol. Gen. Genet.* 227: 229-237 (1991); or from a steroid hormone gene, the transcriptional activity of which is induced by a glucocorticosteroid hormone. Schena et al., *Proc. Natl. Acad. Sci. U.S.A.* 88: 10421 (1991); the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2): 247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156). See International Patent Application No. WO 91/19806 for a review of well-known plant promoters.

Tissue-preferred promoters can be utilized to target enhanced transcription and/or expression within a particular plant tissue. When referring to preferential expression, what is meant is expression at a higher level in the particular plant tissue than in other plant tissue. Examples of these type of promoters include seed preferred expression such as that provided by the phaseolin promoter (Bustos et al. (1989) *The Plant Cell* Vol. 1, 839-853), and the maize globulin-1 gene, Belanger, et al. (1991) *Genetics* 129:863-972. For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, an Ltp1 (See, for example, U.S. Pat. No. 7,550,579), an Ltp2 (Opsahl-Sorteberg, H-G. et al., (2004) *Gene* 341:49-58 and oleosin genes. See also WO 00/12733, where seed-preferred promoters from end1 and end2 genes are disclosed. Seed-preferred promoters also include those promoters that direct gene expression predominantly to specific tissues within the seed such as, for example, the endosperm-preferred promoter of γ-zein, the cryptic promoter from tobacco (Fobert et al. (1994) "T-DNA tagging of a seed coat-specific cryptic promoter in tobacco" *Plant J.* 4: 567-577), the P-gene promoter from corn (Chopra et al.

(1996) "Alleles of the maize P gene with distinct tissue specificities encode Myb-homologous proteins with C-terminal replacements" *Plant Cell* 7:1149-1158, Erratum in *Plant Cell* 1997, 1:109), the globulin-1 promoter from corn (Belanger and Kriz (1991) "Molecular basis for Allelic Polymorphism of the maize Globulin-1 gene" *Genetics* 129: 863-972 and GenBank accession No. L22344), promoters that direct expression to the seed coat or hull of corn kernels, for example the pericarp-specific glutamine synthetase promoter (Muhitch et al., (2002) "Isolation of a Promoter Sequence From the Glutamine Synthetase$_{1-2}$ Gene Capable of Conferring Tissue-Specific Gene Expression in Transgenic Maize" *Plant Science* 163:865-872 and GenBank accession number AF359511) and to the embryo (germ) such as that disclosed at U.S. Pat. No. 7,169,967.

In one embodiment the promoter used in the multiple PTUs may be an embryo preferred promoter. When referring to an embryo preferred promoter is meant that it expresses an operably linked sequence to a higher degree in embryo tissue that in other plant tissue. It may express during embryo development, along with expression at other stages, may express strongly during embryo development and to a much lesser degree at other times.

Globulin promoters are known to one skilled in the art. Such promoters are obtained from nucleic acid molecules which encode a globulin protein. The two most abundant proteins in maize embryos are saline-soluble, water-insoluble globulins, one being a 63,000 Da molecular weight protein encoded by the globulin-1 gene, the other a 45,000 Da molecular weight protein encoded by the globulin-2 gene. See. E.g, Kriz (1989) *Biochem Genet.* 27(3-4):238-51 and Belanger, F. C. and Kriz, A. L. (1991) "Molecular basis for allelic polymorphism of the maize globulin-1 gene" *Genetics* 129, 863-872. Belanger et al. note that the protein is readily detected in a Coomassie-stained gel of protein extracts from embryos and several alleles have been recognized. Belanger et al. (1991), at 865. One example is the promoter associated with the nucleic acid molecule encoding globulin-1. Globulin-1 is the most abundant protein in maize embryos, is a vicilin-like storage protein comprising 10-20% of the maize embryo protein and encoded by the globulin-1 gene. See, e.g., Liu et al. (1992) *MNL* Vol. 22: 108-109. Where a null allele is present no globulin 1 protein is produced. Belanger et al. (1991). One skilled in the art appreciates that nucleic acid molecules that encode the globulin-1 protein (as well as other products which may be produced by a nucleic acid molecule) are well known and readily identified using techniques available to one skilled in the art and as discussed here, including, by way of example without limitation, comparison to known sequences, preparation of a library and screening with a probe, antibody binding, using Northern, Southern or Western blots, among the many avenues available. Examples, without intending to be limiting, of globulin promoters include the 1.45 kb maize globulin-1 promoter plus untranslated leader described by Belanger and Kriz, 1991, supra and GenBank accession L22344 shown in FIG. 1 and is SEQ ID NO: 1. The 1.4 kb Belanger et al. globulin-1 promoter referred to includes the regulatory region of bases 1-1386 (SEQ ID NO: 2), the TATA box of bases 1354-1360 and the 5' untranslated region of bases 1387-1401 (shown in italics and which is SEQ ID NO: 3). The version of the promoter used in the experiments here included an extra 43 bases (SEQ ID NO: 4, shown in bold below the promoter in FIG. 1) which do not form a part of the promoter and believed to be a downstream portion on chromosome 1 of the maize gene, which may originate from a retrotransposon.

Another example of a globulin promoter is a nucleotide sequence natively associated with the nucleotide sequence coding for *Zea mays* extended globulin-1 and in an example comprises SEQ ID NO: 5 shown in FIG. 2. This promoter was first described in U.S. Pat. No. 7,169,967, and is also shown in U.S. Ser. No. 13/558,834, each incorporated herein by reference in its entirety. It includes the proximal approximately 3 kb of a maize extended globulin-1 promoter plus untranslated leader (SEQ ID NO: 5). Transgenic plants generated using this sequence show significantly increased expression over those generated using the Belanger et al. 1.4 kb maize globulin-1 promoter plus untranslated leader described above, which has previously been deployed to express transgenes in maize seeds (Hood et al., 2003; Woodard et al., 2003). The extended globulin-1 promoter plus untranslated leader sequence of patent '967 is highly embryo preferred in its expression pattern, as is the previously cloned globulin-1 promoter sequence of Belanger et al. The untranslated leader sequence (SEQ ID NO: 6) in FIG. 2 is shown in bold type and the translation start codon is capitalized. The regulatory region minus the untranslated leader is SEQ ID NO: 7.

A further example of a globulin promoter is the nucleotide sequence natively associated with the nucleotide sequence coding for globulin-2. See one example described by Wallace and Kriz, "Nucleotide sequence of a cDNA clone corresponding to the maize globulin-2 gene" *Plant Physiol.* 95, 973-975 (1991) and shown at GenBank Accession No. X53715.1. Another example, is the globulin-2 promoter shown at GenBank Accession No. AR947679 and at U.S. Pat. No. 7,112,723 (shown there as sequence 4 and FIG. 3), incorporated herein by reference in its entirety. FIG. 3 shows the entire 3 kb promoter as SEQ ID NO: 8, with the untranslated leader sequence in bold (SEQ ID NO: 9) and the translation start codon capitalized. The regulatory region minus the untranslated region is SEQ ID NO: 10.

In a still further example of an embryo preferred promoter, a promoter from a maize abscisic acid-inducible nucleic acid molecule having preferential expression in plant embryo tissues may be employed. Such a promoter is described at Streatfield et al. (2010) "Identification of maize embryo-preferred promoters suitable for high-level heterologous protein production" GM Crops 1:1-11, at GenBank EA076965 (referred to there and here as pr26) and U.S. Pat. No. 7,183,109 (shown there at FIG. 3 and as sequence 3), incorporated herein by reference in its entirety. The pr26 promoter is shown in FIG. 4 and is SEQ ID NO: 11. The predicted minimal extent of the untranslated leader is shown in FIG. 4 in bold (SEQ ID NO: 12) and the start codon capitalized. The regulatory region minus the untranslated region is SEQ ID NO: 13.

Yet another example of an embryo preferred promoter is the promoter shown at Streatfield et al. (2010), supra, at GenBank HM635908.1 (referred to there and here as pr36) and at US patent Publication 20110091976 (at there at FIG. 1 and as sequence 2) incorporated herein by reference in its entirety. The pr36 promoter is shown in FIG. 5 and is SEQ ID NO: 14. The putative TATA box is underlined, based on consensus sequences and the ATG is in bold.

Clearly, many variations in use of the promoters which may be used in the methods described are available to one skilled in the art.

The multiple PTUs are used with a nucleic acid molecule encoding the product of interest, also referred to as the gene of interest. The "gene of interest" refers to a nucleotide sequence that encodes for a desired polypeptide or protein but also may refer to nucleotide sequences that do not constitute an entire gene, and which do not necessarily encode a polypeptide or protein. For example, when used in a homologous recombination process, the promoter may be placed in a construct with a sequence that targets an area of the chromosome in the plant but may not encode a protein. The promoter can be used to drive mRNA that can be used for a silencing system, such as antisense, and in that instance, no protein is produced. Means of increasing or inhibiting a protein are well known to one skilled in the art and, by way of example, may include, transgenic expression, antisense suppression, co-suppression methods including but not limited to: RNA interference, gene activation or suppression using transcription factors and/or repressors, mutagenesis including transposon tagging, directed and site-specific mutagenesis, chromosome engineering and, homologous recombination. In the case of use with homologous recombination, no in vivo construct will be required.

The nucleic acid molecule may be a heterologous nucleic acid molecule. A heterologous polynucleotide or a heterologous nucleic acid or an exogenous DNA segment refers to a polynucleotide, nucleic acid or DNA segment that originates from a source foreign to the particular host cell, or, if from the same source, is modified from its original form in composition and/or genomic locus by human intervention. A heterologous gene in a host cell includes a gene that is endogenous to the particular host cell, but has been modified or introduced into the plant. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

In an example of a nucleic acid molecule or gene of interest, it may encode a protein that is useful for industrial or pharmaceutical purposes or the like, or to impact the plant itself, such as through expression of a protein that provides disease resistance, insect resistance, herbicide resistance, or impacts agronomic traits as well as grain quality traits. The sequences used with the promoter can be native or non-native sequences to the plant. DNA sequences native to plants as well as non-native DNA sequences can be transformed into plants and used to modulate levels of native or non-native proteins.

Plants have been used to produce a wide range of recombinant proteins of potential economic and/or medicinal importance. These include research chemicals (Hood et al., 1997; Zhong et al., 1999), processing enzymes that are used, for example, in the pharmaceutical industry (Woodard et al., 2003), industrial enzymes that are deployed in large-scale processing operations such as bleaching (Hood et al., 2003; Bailey et al., 2004), candidate vaccine antigens for animal or plant disease prevention (Mason et al., 1992; Haq et al., 1995; Carrillo et al., 1998; Streatfield et al., 2001), and therapeutic pharmaceuticals including antibodies (Daniell et al., 2001; Hood et al., 2002). The expressed proteins may either be purified from the plant tissues (Hood et al., 1997; Woodard et al., 2003) or, if as with vaccines the final application allows it, the recombinant plant material may be processed into a suitable form for use or even deployed directly (Streatfield et al., 2002; Lamphear et al., 2002). By way of example without limitation, in an embodiment the nucleic acid sequence may encode the hepatitis B surface antigen or aprotinin.

In another example the nucleic acid molecule encodes a cellulase. Expression of cellulases in plants can take many forms and any methods are useful with the multiple PTUs described. A description of various methods and cellulases is provided in US publication US20110143398, incorporated herein by reference in its entirety. Such enzymes may be used with cellulosic biomass in production of energy. By "cellulosic biomass" or feedstock is intended biomass that is comprised of plant cell walls and the components therein including, but not limited to, cellulose, hemicellulose, pectin, and lignin. Such cellulosic biomass includes, for example, crop plant residues or undesired plant material that may be left behind in the field after harvest or separated from the desired plant material or forest products or the like. A crop refers to a collection of plants grown in a particular cycle. By "desired plant material" is intended the plant product that is the primary reason for commercially growing the plant. Such desired plant material can be any plant or plant part or plant product that has commercial value. Corn is grown for human and animal consumption, as well as to produce products such as industrial oils, fertilizer and many other uses. Soybeans and wheat are used primarily in food products. There are multitudes of purposes for which these plant materials can be utilized. The desired plant material also includes protein produced by a transgenic polynucleotide. In short, the desired plant material refers to any product from the plant that is useful.

The multiple PTUs when used to encode a cellulase may be used in a process where breakdown of cellulose is desired. An example of such a process is described at US publication US20110143398. It allows for profitable use of desired plant material or what would otherwise be low value or waste material after the desired plant is harvested. What is more, one skilled in the art understands that the production of the plant material for use as plant tissue composition may in itself be production of desired plant material such as when crops such as switch grass are grown for the purpose of producing an energy source. In an embodiment of the invention, an enzyme substitute and/or an enzyme expressed as a heterologous protein in the plant can be used to degrade polysaccharides in a crop and can be produced by the very crop that will be degraded, thereby providing clear advantages in eliminating or reducing the need for an outside source of the enzyme, compacting costs with its production by combining it with production of the cellulose source. In addition, one skilled in the art can appreciate that the transgenic enzymes expressed in such plants may be used in any commercial polysaccharide-degrading process, such as in providing additives to animal feed (See, for example Rode et al., "Fibrolytic enzyme supplements for dairy cows in early lactation" *J. Dairy Sci.* 1999 October; 82(1):2121-6); industrial applications, (for example, in detergent applications, see Winetzky, U.S. Pat. No. 6,565,6131; in biofinishing of denims, see Vollmond, WO 97/25468); treatment of genes, or, in a preferred embodiment, in the production of ethanol.

The cellulases which may be produced in an embodiment may be useful for the conversion of plant cell wall polysaccharides to fermentable sugars that can then be used in the production of ethanol or other desired molecules via fermentation methods known in the art. The use of the term "fermentable sugars" includes, but is not limited to, monosaccharides and disaccharides and also encompasses sugar derivatives such as, for example, sugar alcohols, sugar acids, amino sugars, and the like. The fermentable sugars of the invention encompass any sugar or sugar derivative that is capable of being fermented using microorganisms. An example of production of endocellulases and exocellulases in plants is described at US Patent Publication No. 20060026715, incorporated herein by reference in its entirety. In an embodiment, the plant cell-produced heterologous protein can serve as the source of exogenous cellulose degrading enzyme. It can be purified if desired, or the plant cells or tissue comprising the heterologous enzyme added to the mixture. In one embodiment, the plant tissue composition transformed with one or more cellulose degrading enzymes can be the source of enhancement of the production of fermentable sugars by providing plant tissue composition for such enhancement, and also provide one or more exogenous cellulose degrading enzymes.

The enzymes used in saccharification processes and which may be used with the methods here described currently encompass enzymes that can be employed to degrade plant cell wall polysaccharides into fermentable sugars. Such enzymes are known in the art and include, but are not limited to, enzymes that can catalyze the degradation of cellulose, hemicellulose, and/or pectin. In particular, the methods of the invention are drawn to cellulose-degrading enzymes. By "cellulase" or "cellulose-degrading enzyme" is intended any enzyme that can be utilized to promote the degradation of cellulose into fermentable sugars including, but not limited to, cellulases and glucosidases. By way of example, without limitation, the enzymes classified in Enzyme Classification as 3.2.1.x are included within the scope of the invention. An example of the many enzymes which may be employed in the invention is presented in Table 1, a list of enzymes in the category by the Nomenclature Committee of the International Union of Biochemistry and Molecular Biology (NC-IUBMB).

TABLE 1

Polysaccharide degrading enzymes

EC 3.2.1.1 α-amylase
EC 3.2.1.2 β-amylase
EC 3.2.1.3 glucan 1,4-α-glucosidase
EC 3.2.1.4 cellulase
EC 3.2.1.6 endo-1,3(4)-β-glucanase
EC 3.2.1.7 inulinase
EC 3.2.1.8 endo-1,4-β-xylanase
EC 3.2.1.10 oligo-1,6-glucosidase
EC 3.2.1.11 dextranase
EC 3.2.1.14 chitinase
EC 3.2.1.15 polygalacturonase
EC 3.2.1.17 lysozyme
EC 3.2.1.18 exo-α-sialidase
EC 3.2.1.20 α-glucosidase
EC 3.2.1.21 β-glucosidase
EC 3.2.1.22 α-galactosidase
EC 3.2.1.23 β-galactosidase
EC 3.2.1.24 α-mannosidase
EC 3.2.1.25 β-mannosidase
EC 3.2.1.26 β-fructofuranosidase
EC 3.2.1.28 αα-trehalase
EC 3.2.1.31 β-glucuronidase
EC 3.2.1.32 xylan endo-1,3-β-xylosidase
EC 3.2.1.33 amylo-1,6-glucosidase
EC 3.2.1.35 hyaluronoglucosaminidase
EC 3.2.1.36 hyaluronoglucuronidase
EC 3.2.1.37 xylan 1,4-β-xylosidase
EC 3.2.1.38 β-D-fucosidase
EC 3.2.1.39 glucan endo-1,3-β-D-glucosidase
EC 3.2.1.40 β-L-rhamnosidase
EC 3.2.1.41 pullulanase
EC 3.2.1.42 GDP-glucosidase
EC 3.2.1.43 β-L-rhamnosidase
EC 3.2.1.44 fucoidanase
EC 3.2.1.45 glucosylceramidase
EC 3.2.1.46 galactosylceramidase
EC 3.2.1.47 galactosylgalactosylglucosylceramidase
EC 3.2.1.48 sucrose β-glucosidase
EC 3.2.1.49 α-N-acetylgalactosaminidase
EC 3.2.1.50 α-N-acetylglucosaminidase
EC 3.2.1.51 α-L-fucosidase
EC 3.2.1.52 β-L-N-acetylhexosaminidase TABLE 1-continued Polysaccharide degrading enzymes EC 3.2.1.53 β-N-acetylgalactosaminidase
EC 3.2.1.54 cyclomaltodextrinase
EC 3.2.1.55 α-N-arabinofuranosidase
EC 3.2.1.56 glucuronosyl-disulfoglucosamine glucuronidase
EC 3.2.1.57 isopullulanase
EC 3.2.1.58 glucan 1,3-β-glucosidase
EC 3.2.1.59 glucan endo-1,3-α-glucosidase
EC 3.2.1.60 glucan 1,4-α-maltotetraohydrolase
EC 3.2.1.61 mycodextranase
EC 3.2.1.62 glycosylceramidase
EC 3.2.1.63 1,2-α-L-fucosidase
EC 3.2.1.64 2,6-β-fructan 6-levanbiohydrolase
EC 3.2.1.65 levanase
EC 3.2.1.66 quercitrinase
EC 3.2.1.67 galacturan 1,4-α-galacturonidase
EC 3.2.1.68 isoamylase
EC 3.2.1.70 glucan 1,6-α-glucosidase
EC 3.2.1.71 glucan endo-1,2-β-glucosidase
EC 3.2.1.72 xylan 1,3-β-xylosidase
EC 3.2.1.73 licheninase
EC 3.2.1.74 glucan 1,4-β-glucosidase
EC 3.2.1.75 glucan endo-1,6-β-glucosidase
EC 3.2.1.76 L-iduronidase
EC 3.2.1.77 mannan 1,2-(1,3)-α-mannosidase
EC 3.2.1.78 mannan endo-1,4-β-mannosidase
EC 3.2.1.80 fructan β-fructosidase
EC 3.2.1.81 agarase
EC 3.2.1.82 exo-poly-α-galacturonosidase
EC 3.2.1.83 κ-carrageenase
EC 3.2.1.84 glucan 1,3-β-glucosidase
EC 3.2.1.85 6-phospho-β-galactosidase
EC 3.2.1.86 6-phospho-β-glucosidase
EC 3.2.1.87 capsular-polysaccharide endo-1,3-α-galactosidase
EC 3.2.1.88 β-L-arabinosidase
EC 3.2.1.89 arabinogalactan endo-1,4-β-galactosidase
EC 3.2.1.91 cellulose 1,4-β-cellobiosidase
EC 3.2.1.92 peptidoglycan β-N-acetylmuramidase
EC 3.2.1.93 αα-phosphotrehalase
EC 3.2.1.94 glucan 1,6-α-isomaltosidase
EC 3.2.1.95 dextran 1,6-α-isomaltotriosidase
EC 3.2.1.96 mannosyl-glycoprotein endo-β-N-acetylglucosaminidase
EC 3.2.1.97 glycopeptide α-N-acetylgalactosaminidase
EC 3.2.1.98 glucan 1,4-α-maltohexaosidase
EC 3.2.1.99 arabinan endo-1,5-α-L-arabinosidase
EC 3.2.1.100 mannan 1,4-mannobiosidase
EC 3.2.1.101 mannan endo-1,6-α-mannosidase
EC 3.2.1.102 blood-group-substance endo-1,4-β-galactosidase
EC 3.2.1.103 keratan-sulfate endo-1,4-β-galactosidase
EC 3.2.1.104 sterl-β-glucosidase
EC 3.2.1.105 strictosidine β-glucosidase
EC 3.2.1.106 mannosyl-oligosaccharide glucosidase
EC 3.2.1.107 protein-glucosylgalactosylhydroxylysine glucosidase
EC 3.2.1.108 lactase
EC 3.2.1.109 endogalactosaminidase
EC 3.2.1.110 mucinaminylserine mucinaminidase
EC 3.2.1.111 1,3-α-L-fucosidase
EC 3.2.1.112 2-deoxyglucosidase
EC 3.2.1.113 mannosyl-oligosaccharide 1,2-α-mannosidase
EC 3.2.1.114 mannosyl-oligosaccharide 1,3-1,6-α-mannosidase
EC 3.2.1.115 branched-dextran exo-1,2-α-glucosidase
EC 3.2.1.116 glucan 1,4-α-maltotriohydrolase
EC 3.2.1.117 amygdalin β-glucosidase
EC 3.2.1.118 prunasin β-glucosidase
EC 3.2.1.119 vicianin β-glucosidase
EC 3.2.1.120 oligoxyloglucan β-glycosidase
EC 3.2.1.121 polymannuronate hydrolase
EC 3.2.1.122 maltose-6'-phosphate glucosidase
EC 3.2.1.123 endoglycosylceramidase
EC 3.2.1.124 3-deoxy-2-octulosonidase
EC 3.2.1.125 raucaffricine β-glucosidase
EC 3.2.1.126 coniferin β-glucosidase
EC 3.2.1.127 1,6-α-L-fucosidase
EC 3.2.1.128 glycyrrhizinate β-glucuronidase
EC 3.2.1.129 endo-α-sialidase
EC 3.2.1.130 glycoprotein endo-α-1,2-mannosidase
EC 3.2.1.131 xylan α-1,2-glucuronosidase
EC 3.2.1.132 chitosanase
EC 3.2.1.133 glucan 1,4-α-maltohydrolase TABLE 1-continued Polysaccharide degrading enzymes EC 3.2.1.134 difructose-anhydride synthase
EC 3.2.1.135 neopullulanase
EC 3.2.1.136 glucuronoarabinoxylan endo-1,4-β-xylanase
EC 3.2.1.137 mannan exo-1,2-1,6-β-mannosidase
EC 3.2.1.139 α-glucuronidase
EC 3.2.1.140 lacto-N-biosidase
EC 3.2.1.141 4-α-D-((1 → 4)-α-D-glucano)trehalose trehalohydrolase
EC 3.2.1.142 limit dextrinase
EC 3.2.1.143 poly(ADP-ribose) glycohydrolase
EC 3.2.1.144 3-deoxyoctulosonase
EC 3.2.1.145 galactan 1,3-β-galactosidase
EC 3.2.1.146 β-galactofuranosidase
EC 3.2.1.147 thioglucosidase
EC 3.2.1.149 β-primeverosidase
EC 3.2.1.150 oligoxyloglucan reducing-end-specific cellobiohydrolase
EC 3.2.1.151 xyloglucan-specific endo-β-1,4-glucanase
EC 3.2.1.152 mannosylglycoprotein endo-β-mannosidase
EC 3.2.1.153 fructan β-(2,1)-fructosidase
EC 3.2.1.154 fructan β-(2,6)-fructosidase
EC 3.2.1.156 oligosaccharide reducing-end xylanase For the degradation of cellulose, two types of exoglucanase have been described that differ in their approach to the cellulose chain. One type attacks the non-reducing end and the other attacks the reducing end. Cellulase enzymes which cleave the cellulose chain internally are referred to as endo-β-1,4-glucanases (E.C. 3.2.1.4) and serve to provide new reducing and non-reducing chain termini on which exo-β-1,4-glucanases (cellobiohydrolase, CBH; E.C. 3.2.1.91) can operate (Tomme et al. (1995) *Microbial Physiology* 37:1-81). The product of the exoglucanase reaction is typically cellobiose, so a third activity, β-D-glucosidase (E.C. 3.2.1.21), is required to cleave cellobiose to glucose. The exoglucanase can also yield longer glucose chains (up to 6 glucose units) that will require a β-D-glucosidase activity to reduce their size. Relative to the other enzyme activities needed for degradation of cellulose into fermentable sugars, only a minor amount of the β-D-glucosidase activity is required. In brief, current processes to produce fermentable sugars involve the addition to a cellulose-containing composition an endocellulase (endo-β-1,4-glucanases) and an exocellulase (exo-β-1,4-glucanases) which cleaves the cellulose chain internally. In order to produce the end product of glucose, a third enzyme is involved, a glucosidase (β-D-glucosidases), which acts on the cellobiose to produce glucose. One skilled understands that other proteins can increase the rate as, for example, expansins, which unfold the crystalline cellulose to make it more available so the enzymes can degrade it more efficiently. Cosgrove (1999) *Annu Rev Plant Physiol Plant Mol Biol* 50:391-417.

If desired, the gene of interest can be optimized for plant translation by optimizing the codons used for plants and the sequence around the translational start site for plants. Sequences resulting in potential mRNA instability can also be avoided.

Clearly, one skilled in the art appreciates there can be variations in the promoter or nucleic acid sequence tolerated and still produce the increased expression described. Identity to a sequence described can be a polynucleotide sequence having at least 65% sequence identity, more preferably at least 70% sequence identity, more preferably at least 75% sequence identity, more preferably at least 80% identity, and more preferably at least 85% 86%, 87%, 88%, 89%, 90%, 91%, 92%, 93%, 94%, 95%, 96%, 97%, 98%, 99% sequence identity with a sequence exemplified or described herein. Hybridization and hybridization conditions as provided herein can also be used to define polynucleotide sequences of the invention.

The nucleotide sequences of the promoter or nucleic acid molecule can be used to isolate corresponding sequences from other organisms, particularly other plants, or to synthesize synthetic sequences. In this manner, methods such as PCR, hybridization, synthetic gene construction and the like can be used to identify or generate such sequences based on their sequence homology to the sequences set forth herein. Sequences identified, isolated or constructed based on their sequence identity to the whole of or any portion of the original sequence may be used in the present invention. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed (Sambrook et al., 1989; Innis et al., 1990; Innis et al., 1995; Innis et al., 1999). Known methods of PCR include, but are not limited to, methods using paired primers, nested primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the DNA sequences of the invention. Methods for preparation of probes for hybridization and for construction of cDNA and genomic libraries are generally known in the art and are disclosed (Sambrook et al., 1989).

For example, the sequence, or one or more portions thereof, may be used as a probe capable of specifically hybridizing to corresponding sequences. To achieve specific hybridization under a variety of conditions, such probes include sequences that are unique among the sequences to be screened and are preferably at least about 10 nucleotides in length, and most preferably at least about 20 nucleotides in length. Such sequences may alternatively be used to amplify corresponding sequences from a chosen plant by PCR. This technique may be used to isolate sequences from a desired plant or as a diagnostic assay to determine the presence of sequences in a plant. Hybridization techniques include hybridization screening of DNA libraries plated as either plaques or colonies (Sambrook et al., 1989).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1.0 M NaCl, 1% SDS at 37° C., and a wash in 0.1×SSC at 60 to 65° C.

Specificity is also the function of post-hybridization washes, the critical factors being the ionic strength and temperature of the final wash solution. For DNA-DNA hybrids, the $T_m$ can be approximated from the equation $T_m=81.5°$ C.$+16.6$ (logM)$+0.41$(% GC)$-0.61$(% form.)$-500/L$, where M is the molarity of monovalent cations, % GC is the percentage of guanosine and cytosine nucleotides in the DNA, % form. is the percentage of formamide in the hybridization solution, and L is the length of the hybrid in base pairs (Meinkoth and Wahl, 1984). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Ausubel et al. (1993) and Sambrook et al. (1989).

Thus, isolated sequences that have promoter activity and which hybridize under stringent conditions to the promoter sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to accurately reflect the similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Optimal alignment of sequences for comparison can use any means to analyze sequence identity (homology) known in the art, e.g., by the progressive alignment method of termed "PILEUP" (Morrison, Mol. Biol. Evol. 14:428-441 (1997), as an example of the use of PILEUP); by the local homology algorithm of Smith & Waterman (Adv. Appl. Math. 2: 482 (1981)); by the homology alignment algorithm of Needleman & Wunsch (J. Mol. Biol. 48:443 (1970)); by the search for similarity method of Pearson (Proc. Natl. Acad. Sci. USA 85: 2444 (1988)); by computerized implementations of these algorithms (e.g., GAP, BEST FIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins, Gene 73: 237-244 (1988); Corpet, Nucleic Acids Res. 16:10881-10890 (1988); Huang, Computer Applications in the Biosciences 8:155-165 (1992); and Pearson, Methods in Mol. Biol. 24:307-331 (1994); Pfam (Sonnhammer, Nucleic Acids Res. 26:322-325 (1998); TreeAlign (Hein, Methods Mol. Biol. 25:349-364 (1994); MEG-ALIGN, and SAM sequence alignment computer programs; or, by manual visual inspection.

Another example of algorithm that is suitable for determining sequence similarity is the BLAST algorithm, which is described in Altschul et al, J. Mol. Biol. 215: 403-410 (1990). The BLAST programs (Basic Local Alignment Search Tool) of Altschul, S. F., et al., (1993) J. Mol. Biol. 215:403-410) searches under default parameters for identity to sequences contained in the BLAST "GENEMBL" database. A sequence can be analyzed for identity to all publicly available DNA sequences contained in the GENEMBL database using the BLASTN algorithm under the default parameters.

Software for performing BLAST analyses is publicly available through the National Center for Biotechnology Information, www.ncbi.nlm.nih.gov/; see also Zhang, Genome Res. 7:649-656 (1997) for the "PowerBLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al, J. Mol. Biol. 215: 403-410 (1990)). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a wordlength (W) of 11, the BLOSUM62 scoring matrix (see Henikoff, Proc. Natl. Acad. Sci. USA 89:10915-10919 (1992)) alignments (B) of 50, expectation (E) of 10, M=5, N=−4, and a comparison of both strands. The term BLAST refers to the BLAST algorithm that performs a statistical analysis of the similarity between two sequences; see, e.g., Karlin, Proc. Natl. Acad. Sci. USA 90:5873-5787 (1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In an embodiment, GAP (Global Alignment Program) can be used. GAP uses the algorithm of Needleman and Wunsch J. Mol. Biol. 48:443-453 (1970) to find the alignment of two complete sequences that maximizes the number of matches and minimizes the number of gaps. Default gap creation penalty values and gap extension penalty values in the commonly used Version 10 of the Wisconsin Package® (Accelrys, Inc., San Diego, Calif.) for protein sequences are 8 and 2, respectively. For nucleotide sequences the default gap creation penalty is 50 while the default gap extension penalty is 3. Percent Similarity is the percent of the symbols that are similar. Symbols that are across from gaps are ignored. A similarity is scored when the scoring matrix value for a pair of symbols is greater than or equal to 0.50, the similarity threshold. A general purpose scoring system is the BLOSUM62 matrix (Henikoff and Henikoff, Proteins, 17: 49-61 (1993)), which is currently the default choice for BLAST programs. BLOSUM62 uses a combination of three matrices to cover all contingencies. Altschul, J. Mol. Biol. 36: 290-300 (1993), herein incorporated by reference in its entirety and is the scoring matrix used in Version 10 of the Wisconsin Package® (Accelrys, Inc., San Diego, Calif.) (see Henikoff & Henikoff (1989) Proc. Natl. Acad. Sci. USA 89:10915).

As used herein, "sequence identity" or "identity" in the context of two nucleic acid sequences makes reference to the residues in the two sequences that are the same when aligned for maximum correspondence over a specified comparison window.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

Identity to the sequence of the present invention would mean a polynucleotide sequence having at least 65% sequence identity, more preferably at least 70% sequence identity, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity.

"Functional variants" of the sequence disclosed may be used. Functional variants include, for example, sequences having one or more nucleotide substitutions, deletions or insertions and wherein the variant retains promoter activity, particularly the ability to drive expression preferentially to the embryo of a plant, or encodes the product. Functional variants can be created by any of a number of methods available to one skilled in the art, such as by site-directed mutagenesis, induced mutation, identified as allelic variants, cleaving through use of restriction enzymes, or the like. Activity can likewise be measured by any variety of techniques, including measurement of reporter activity as is described at U.S. Pat. No. 6,844,484, Northern blot analysis or similar techniques.

Further, a "functional fragment" may be used, that is a regulatory fragment formed by one or more deletions from a larger regulatory element, or a fragment of a nucleic acid sequence that encodes a desired product. For example, the 5' portion of a promoter up to the TATA box near the transcription start site can be deleted without abolishing promoter activity, as described by Opsahl-Sorteberg, H-G. et al., 2004. Such fragments should retain promoter activity, particularly the ability to drive expression of operably linked nucleotide sequences. Activity can be measured by Northern blot analysis, reporter activity measurements when using transcriptional fusions, and the like. See for example, Sambrook et al. (1989). Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology. See particularly, Mullis et al. (1987) and Erlich, ed. (1989).

For example, a routine way to remove a part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at the 5' overhangs, blunt ends or nicks in the DNA template. However, the exonuclease III is unable to remove nucleotides at 3' 4-base overhangs. Timed digest of a clone with this enzyme produces unidirectional nested deletions.

Once the gene is engineered to contain desired features, such as the desired subcellular localization sequences, it may then be placed into an expression vector by standard methods. The selection of an appropriate expression vector will depend upon the method of introducing the expression vector into host cells. A typical expression vector contains prokaryotic DNA elements coding for a bacterial origin of replication and an antibiotic resistance gene to provide for the growth and selection of the expression vector in the bacterial host; a cloning site for insertion of an exogenous DNA sequence; eukaryotic DNA elements that control initiation of transcription of the exogenous gene (such as the promoter of the invention or another promoter); and DNA elements that control the processing of transcripts, such as transcription termination/polyadenylation sequences. It also can contain such sequences as are needed for the eventual integration of the vector into the plant chromosome.

One skilled in the art will appreciate that various other components may be included in a vector used with the multiple PTUs and will vary depending on the specific application. In general, the methods available for construction of recombinant genes, optionally comprising various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., 1989).

In one embodiment, the expression vector may also contain a gene encoding a selectable or scoreable marker that is operably or functionally linked to a promoter that controls transcription initiation, which can be the promoter of the invention or another promoter. By "operably linked" it is understood that the gene of interest is oriented in connection to the gene such that the promoter initiates transcription of the gene in order to allow its expression of the resulting protein in plants. For a general description of plant expression vectors and reporter genes, see Gruber et al. (1993). For example, the selective gene may be a glufosinate-resistance encoding DNA and in another example it can be phosphinothricin acetyl transferase (pat) or a maize optimized pat gene under the control of the CaMV 35S promoter. Such pat genes confer resistance to the herbicide bialaphos (Gordon-Kamm et al., 1990).

The multiple PTUs driving the gene of interest may be used in conjunction with other promoters used to drive other nucleotide sequences than the gene of interest where desired. In one embodiment, a plant selection marker and the gene of interest can be both functionally linked to the same promoter. In another embodiment, a plant selection marker and the gene of interest can be functionally linked to different promoters. These other promoter elements can be those that are constitutive or sufficient to render promoter-dependent gene expression controllable as being cell-type specific, tissue-specific or time or developmental stage specific, or being inducible by external signals or agents. Such elements may be located in the 5' or 3' regions of the gene. Although the additional promoter may be the endogenous promoter of a structural gene of interest, the promoter can also be a foreign regulatory sequence. Promoter elements employed to control expression of product proteins and the selection gene can be any plant-compatible promoters.

The expression vector can optionally also contain a signal sequence located between the promoter and the gene of interest. A signal sequence is a nucleotide sequence, translated to give an amino acid sequence, which is used by a cell to direct the protein or polypeptide of interest to be placed in a particular place within or outside the eukaryotic cell. One example of a plant signal sequence is the barley α-amylase secretion signal (Rogers, 1985). Many signal sequences are known in the art. See, for example Becker et al. (1992), Fontes et al. (1991), Matsuoka and Nakamura (1991), Gould et al. (1989), Creissen et al. (1992), Kalderon et al. (1984) and Stiefel et al. (1990).

Leader sequences can be included to enhance translation. Instead of, or in addition to the untranslated leader sequence of the promoter, other leader sequences may be substituted or added. Translation leaders are known in the art and include: picornavirus leaders, for example, EMCV leader (Encephalomyocarditis 5' noncoding region) (Elroy-Stein et al. (1989); potyvirus leaders, for example, TEV leader (Tobacco Etch Virus) (Gallie et al. (1995)); human immunoglobulin heavy-chain binding protein (BiP) (Macejak et al. (1991)); untranslated leader from the coat protein mRNA of alfalfa mosaic virus (AMV RNA 4) (Jobling et al. (1987)); tobacco mosaic virus leader (TMV) (Gallie. (1989)); and maize chlorotic mottle virus leader (MCMV) (Lommel et al. (1991)). See also, Della-Cioppa et al. (1987). Other methods known to enhance translation can also be utilized, for example, introns, and the like. Obviously, many variations on the promoters, selectable markers, signal sequences, leader sequences, termination sequences, introns, enhancers and other components of the construct are available to one skilled in the art.

It is anticipated the invention can be used with monocotyledonous or dicotyledonous plants. Examples of monocotyledonous plants are plants which belong to the genus of avena (oat), triticum (wheat), secale (rye), hordeum (barley), oryza (rice), panicum, pennisetum, setaria, sorghum (millet), zea (maize). Dicotyledonous useful plants are, inter alia, leguminous plants, such as legumes and especially alfalfa, soybean, rape, tomato, sugar beet, and potato.

The PTUs of the invention may be introduced into any plant or plant part. The term plant or plant material or plant part is used broadly herein to include any plant at any stage of development, or to part of a plant, including a plant cutting, a plant cell, a plant cell culture, a plant organ, a plant seed, and a plantlet. Examples of such plant parts are plant cells, embryos, protoplasts, meristematic cells, callus, pollen, leaves, anthers, roots, root tips, silk, flowers, kernels, ears, cobs, husks or stalks. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered a plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like. Still further, the present invention provides plants regenerated from the tissue cultures of the invention.

Methods for introducing expression vectors into plant tissue available to one skilled in the art are varied and will depend on the plant selected. Procedures for transforming a wide variety of plant species are well known and described throughout the literature. See, for example, Mild and McHugh (2004); Klein et al. (1992); and Weising et al. (1988). For example, the DNA construct may be introduced into the genomic DNA of the plant cell using techniques such as microprojectile-mediated delivery (Klein et al. 1992), electroporation (Fromm et al., 1985), polyethylene glycol (PEG) precipitation (Mathur and Koncz, 1998), direct gene transfer (WO 85/01856 and EP-A-275 069), in vitro protoplast transformation (U.S. Pat. No. 4,684,611) and microinjection of plant cell protoplasts or embryogenic callus (Crossway, 1985). Co-cultivation of plant tissue with *Agrobacterium tumefaciens* is another option, where the DNA constructs are placed into a binary vector system (Ishida et al., 1996). The virulence functions of the *Agrobacterium tumefaciens* host will direct the insertion of the construct into the plant cell DNA when the cell is infected by the bacteria. See, for example, Fraley et al. (1983).

Standard methods for transformation of canola are described by Moloney et al. (1989). Corn transformation is described by Fromm et al. (1990) and Gordon-Kamm et al. (1990). *Agrobacterium* is primarily used in dicots, but certain monocots such as maize can be transformed by *Agrobacterium*. See, for example, U.S. Pat. No. 5,550,318. Rice transformation is described by Hiei et al. (1994) and Lee et al. (1991). Wheat can be transformed by techniques similar to those used for transforming corn or rice. Sorghum transformation is described by Casas et al. (1993) and barley transformation is described by Wan and Lemaux (1994). Soybean transformation is described in a number of publications, including U.S. Pat. No. 5,015,580.

In one method, the *Agrobacterium* transformation methods of Ishida et al. (1996) and also described in U.S. Pat. No. 5,591,616, are generally followed, with modifications that the inventors have found improve the number of transformants obtained. The Ishida method uses the A188 variety of maize that produces Type I callus in culture. In one preferred embodiment the Hi II maize line is used which initiates Type II embryogenic callus in culture (Armstrong et al., 1991).

While Ishida recommends selection on phosphinothricin when using the bar or pat gene for selection, another preferred embodiment provides use of bialaphos instead. In general, as set forth in the U.S. Pat. No. 5,591,616 patent, and as outlined in more detail below, dedifferentiation is obtained by culturing an explant of the plant on a dedifferentiation-inducing medium for not less than seven days, and the tissue during or after dedifferentiation is contacted with *Agrobacterium* having the gene of interest. The cultured tissue can be callus, an adventitious embryo-like tissue or suspension cells, for example. In this preferred embodiment, the suspension of *Agrobacterium* has a cell population of $10^6$ to $10^{11}$ cells/ml and are contacted for three to ten minutes with the tissue, or continuously cultured with *Agrobacterium* for not less than seven days. The *Agrobacterium* can contain plasmid pTOK162, with the gene of interest between border sequences of the T region of the plasmid, or the gene of interest may be present in another plasmid-containing *Agrobacterium*. The virulence region may originate from the virulence region of a Ti plasmid or Ri plasmid. The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA101, selecting for spectinomycin resistance. The plasmid is isolated to assure that the EHA101 contains the plasmid. EHA101 contains a disarmed pTi that carries resistance to kanamycin. See, Hood et al. (1986).

Further, the Ishida protocol as described provides for growing fresh culture of the *Agrobacterium* on plates, scraping the bacteria from the plates, and resuspending in the co-culture medium as stated in the U.S. Pat. No. 5,591,616 patent for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose per liter, all at a pH of 5.8. In a further preferred method, the bacteria are grown overnight in a 1 ml culture and then a fresh 10 ml culture is re-inoculated the next day when transformation is to occur. The bacteria grow into log phase, and are harvested at a density of no more than $OD_{600}=0.5$, preferably between 0.2 and 0.5. The bacteria are then centrifuged to remove the media and resuspended in the co-culture medium. Since Hi II is used, medium preferred for Hi II is used. This medium is described in considerable detail by Armstrong and Green (1985). The resuspension medium is the same as that described above. All further Hi II media are as described in Armstrong and Green (1985). The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

In accordance with the present invention, a transgenic plant is produced that contains an introduced multiple PTU. It can be combined with any one of the components set forth above.

In a further embodiment, plant breeding can be used to introduce the nucleotide sequences into other plants once transformation has occurred. This can be accomplished by any means known in the art for breeding plants such as, for example, cross pollination of the transgenic plants that are described above with other plants, and selection for plants from subsequent generations which express the amino acid sequence. The plant breeding methods used herein are well known to one skilled in the art. For a discussion of plant breeding techniques, see Poehlman and Sleper (1995). Many crop plants useful in this method are bred through techniques that take advantage of the plant's method of pollination. A plant is self-pollinating if pollen from one flower is transferred to the same or another flower of the same plant. A plant is cross-pollinating if the pollen comes from a flower on a different plant. For example, in *Brassica*, the plant is normally self-sterile and can only be cross-pollinated unless, through discovery of a mutant or through genetic intervention, self-compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (*Zea mays* L.) can be bred by both self-pollination and cross-pollination techniques. Maize has male flowers, located on the tassel, and female flowers, located on the ear, on the same plant. It can self or cross-pollinate.

Pollination can be by any means, including but not limited to hand, wind or insect pollination, or mechanical contact between the male fertile and male sterile plant. For production of hybrid seeds on a commercial scale in most plant species pollination by wind or by insects is preferred.

Stricter control of the pollination process can be achieved by using a variety of methods to make one plant pool male sterile, and the other the male fertile pollen donor. This can be accomplished by hand detas sling, cytoplasmic male sterility, or control of male sterility through a variety of methods well known to the skilled breeder. Examples of more sophisticated male sterility systems include those described by Brar et al., U.S. Pat. Nos. 4,654,465 and 4,727,219 and Albertsen et al., U.S. Pat. Nos. 5,859,341 and 6,013,859.

Backcrossing methods may be used to introduce the gene into the plants. This technique has been used for decades to introduce traits into a plant. An example of a description of this and other plant breeding methodologies that are well known can be found in references such as Neal (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

A variety of assays for the presence of and determine the expression level of the product encoded by the nucleic acid molecule are well known to a person skilled in the art. Methods to detect presence of E1 and CBH1 in extracts prepared from callus and seeds of plants having the heterologous protein, for example, are known. See, Coughlan et al. ((1988) *J. Biol. Chem.* 263:16631-16636) and Freer ((1993) *J. Biol. Chem.* 268:9337-9342). In addition, Western analysis and ELISAs can be used to assess protein integrity and expression levels. Individual $T_1$ seeds are screened by the assay of choice for expression of the target protein. Plants having homozygous condition of the transgenic construct expressing the protein, that is more than one copy of the gene, are expected to have increased expression levels of the enzyme. Expression levels of two to three to four fold or more are expected. It is expected that certain germplasm may have higher levels of expression of the enzyme and may also be selected. The individual plants expressing the highest levels of active enzyme are chosen for field studies, which include back-crosses (See "Plant Breeding Methodology" edit. Neal Jensen, John Wile & Sons, Inc. 1988), selection for increased expression and increased seed amounts. As is evident to one skilled in the art, it is possible to use the processes described to produce a biomass of transformed plants, select higher or highest expressing plant(s), and from selected plant(s) may produce a further biomass of plants expressing the desired protein at higher levels and thus provide a convenient source of the protein.

A Western analysis is a variation of the Southern analysis technique. With a Southern analysis, DNA is cut with restriction endonucleases and fractionated on an agarose gel to separate the DNA by molecular weight and then transferring to nylon membranes. It is then hybridized with the probe fragment which was radioactively labeled with $^{32}P$ and washed in an SDS solution. In the Western analysis, instead of isolating DNA, the protein of interest is extracted and placed on an acrylamide gel. The protein is then blotted onto a membrane and contacted with a labeling substance. See e.g., Hood et al., "Commercial Production of Avidin from Transgenic Maize; Characterization of Transformants, Production, Processing, Extraction and Purification" *Molecular Breeding* 3:291-306 (1997).

The ELISA or enzyme linked immunoassay has been known since 1971. In general, antigens solubilised in a buffer are coated on a plastic surface. When serum is added, antibodies can attach to the antigen on the solid phase. The presence or absence of these antibodies can be demonstrated when conjugated to an enzyme. Adding the appropriate substrate will detect the amount of bound conjugate which can be quantified. A common ELISA assay is one which uses biotinylated anti-(protein) polyclonal antibodies and an alkaline phosphatase conjugate. For example, an ELISA used for quantitative determination of laccase levels can be an antibody sandwich assay, which utilizes polyclonal rabbit antibodies obtained commercially. The antibody is conjugated to alkaline phosphatases for detection. In another example, an ELISA assay to detect trypsin or trypsinogen uses biotinylated anti-trypsin or anti-trypsinogen polyclonal antibodies and a streptavidin-alkaline phosphatase conjugate.

An initial test of enzymatic function in one embodiment is performed with lines of processed corn seed. For saccharification of cellulose, plant tissue from these lines are mixed in the appropriate ratio to produce a high specific activity for degradation of crystalline cellulose. According to Baker et al. ((1995) "Synergism between purified bacterial and fungal cellulases", in *Enzymatic Degradation of Insoluble Carbohydrates*. ACS Series 618, American Chemical Society, Washington, D.C., pp. 113-141.), in an embodiment, maximum synergism for saccharification of cellulose is with a composite that is about 80% of the *Trichoderma reesei* CBHI (exo-β-1,4-glucanase) and about 20% of the *Acidothermus cellulolyticus* endo-β-1,4-glucanase. The addition of about 0.1% of the *Candida wickerhamii* β-D-glucosidase facilitates the degradation of short glucose oligomers (dp=2-6) to yield glucose. In transgenic enzyme production, later, cross pollination of the selected lines can be used to produce lines that express all three of the cellulase-degrading enzymes or these different enzymes can be engineered into one construct which in turn is transformed into the plant.

The product produced may be used in any convenient manner, whether the protein is extracted, and extract prepared as described below, or tissue or plant parts or plants comprising the product utilized. When referring to a plant tissue composition is meant any plant part, plant tissue (which can be optionally ground, sieved, pulverized, chopped, sliced, minced, ground, crushed, mashed or soaked or the like as long as the desired property is retained) or extract. Further, it is not meant to imply the entire plant must be used or that plant tissue or cells must be present in the composition in the final extract where an extract is provided as long as plant cells are used to produce the extract. For example, plant seed, leaves, roots, stem or other plant parts and tissue of plant parts and extracts of same can be employed in an embodiment of the invention. Seed tissue can include the whole seed or its parts, including pericarp (kernel or hull), embryo (called the germ in processing language), or endosperm. In an embodiment, the plant tissue is embryo plant tissue or extract. The plant seed tissue may be in another embodiment a grain seed or part thereof. In yet another embodiment, the plant tissue is a corn seed tissue or part thereof, such as, for example, an embryo that is also referred to as the germ. When referring to tissue is meant an aggregate of cells that can constitute structure(s) or component(s) of the plant, or which can be a portion of such structure or component, or which are from more than one such structure or organ. Seed tissue can be whole seed, portions of the seed, and ground or pulverized or otherwise processed in a manner that is convenient. The tissue composition in one embodiment can be a suspension of plant cells. As has been noted, whole plant may be used where convenient for the process, though one may desire to instead use other plant parts for other profitable uses.

The tissue composition can also be provided as an extract. While it may be convenient to provide tissue in the form of plant parts, whole seed or seed components, for example, one may also prepare flour or the like, there may be instances in which use of an extract is desired. Any of the many available means to prepare such an extract can be employed. When referring to an extract is meant the general process of placing tissue/cells in a liquid, preferably a buffer (the tissue may be optionally ground or otherwise pre-treated), and removing the supernatant. In one embodiment, the tissue may be in the liquid, without the need to purify a single protein. The supernatant may be further passed through a desalting column to separate high molecular weight from low molecular weight compounds, and the high molecular weight fraction used. However, in a commercial situation, the presence of glucose could be highly desirable. Thus one can prepare an extract in those situations where it is convenient to do so, by simple placing tissue in a liquid. A person skilled in the art could test any such extract for use in the invention by determining if it provides the increase in fermentable sugars and/or synergist result found here. For example, one may test the extract by determining if it increases production of fermentable sugars from cellulose when added with a combination of endocellulase, exocellulase and β-D glucosidase (such as, for example, the commercially available Spezyme® composition) and determining if release of fermentable sugars is at least 25% higher compared to the same process where the extract is not added. Further, one could test to determine if fermentable sugars are released when the extract is combined with cellulose, with reduced amounts of cellulase, or with no additional β-D glucosidase added. In another embodiment, one could test to determine if glucose is produced when the extract is combined with cellulose and no additional cellulase or β-D glucosidase is added.

The following is presented by way of illustration and is not intended to be limiting.

EXAMPLES

Example 1

To obtain high expression of cellulase in the germ, a promoter derived from the globulin-1 storage protein (Belanger, 1989, Kriz, 1989) has been used (Hood, 2007). Recently, several additional strong embryo-preferred promoters including those of the globulin-2 gene and two genes of unknown function (pr36 and pr26) were identified with the hope that these would be useful to confer high levels of recombinant protein expression in maize (Streatfield, 2010). The globulin-2 gene is that shown at GenBank accession number AR947679 (SEQ ID NO: 8). To assess the use of these promoters to increase cellulase expression in transgenic maize, a series of constructs expressing either E1 (from *Acidothermus cellulolyticus*) or CBHI (from *Trichoderma reesei*) under control of various combinations of these promoters were prepared. This combination of E1 and CBHI was chosen because they exhibit synergistic activity on lignocellulosic substrates, high temperature optima, and compatible pH optima (Mohagherghi 1986, Nieves 1995, Shoemaker 1983, Baker 1998, Hood 2007).

Results

As shown below, use of transcription units driven by repeats of the same promoter and also where driven by different multiple promoters can increase expression. This is useful, as demonstrated, with an endocellulase, that is an endo-β-1,4-glucanase (E1, E.C. 3.2.1.4), and with an exocellulase, that is an exo-β-1,4-glucanase (cellobiohydrolase, CBH; E.C. 3.2.1.91).

The 1.4 kb globulin-1 promoter is the globulin-1 promoter described by Belanger and Kriz (1991) (here, SEQ ID NO: 1) and in the experiments below this specific promoter used included 43 extra base pairs (SEQ ID NO: 4) which are not a part of the promoter. The 3 kb extended globulin-1 is the extended globulin-1 promoter (SEQ ID NO: 5), incorporated herein by reference in its entirety. The globulin-2 promoter is shown at SEQ ID NO: 8 and the specific sequence used in the experiments described below has a minor variation in that the G nucleotide at position 279 is deleted, and the A nucleotide at position 728 is replaced by a C (this variation is SEQ ID NO: 20). The pr26 promoter used is SEQ ID NO: 11 and the specific sequence used in the experiments below has a minor variation in that the T directly preceding the ATG translation start site was deleted and an extra CACC sequence was inserted at this location. The pr36 promoter used is SEQ ID NO: 14 and the specific sequence used in the experiment below has a minor variation in that there is an extra GGGCAACC directly preceding the ATG translation start site (this variation is SEQ ID NO: 21). The extra regions are inconsequential variations on the promoters.

Constructs were made with either the E1 or CBHI cellulase enzyme under the control of the embryo-preferred promoters as shown in FIGS. 6a and 6b. One series included multiple copies of a transcription unit driven by the 3 kb maize globulin-1 promoter. While adding additional copies of the same transcription unit may increase expression, a concern with this approach is that it may be prone to lowered expression due to recombination or gene silencing. Thus, constructs with three separate transcription units driven by three different promoters were also prepared for comparison. For E1 the globulin-1, globulin-2, and pr26 promoters were used. The pr26 promoter is found at GenBank accession No. EA076965. For CBHI the globulin-1, globulin-2, and pr36 promoters were used. In previous work it was found that E1 was expressed at the highest level when targeted to the vacuole but was also strongly expressed in the endoplasmic reticulum (Hood, 2007). Thus a construct with one copy of E1 targeted to the vacuole and one targeted to the ER was prepared. Each of the constructs was used to transform maize and multiple events were obtained based on resistance to bialaphos. Multiple plants from independent transformation events were regenerated and a summary of the seed obtained available for biochemical analysis is shown in Table 2.

TABLE 2

Number of transformation events and plants analyzed for each construct

| Construct | Independent transformation events | Total number of plants |
|---|---|---|
| CEA | 6 | 45 |
| CEB | 10 | 72 |
| CEC | 8 | 44 |
| CEJ | 8 | 51 |
| CEK | 11 | 60 |

TABLE 2-continued

Number of transformation events and
plants analyzed for each construct

| Construct | Independent transformation events | Total number of plants |
|---|---|---|
| CEL | 9 | 70 |
| BCU | 9 | 61 |
| CCA | 9 | 48 |
| CCF | 13 | 56 |
| CCG | 14 | 67 |

Cellulase expression was assessed using a biochemical assay with 4-methyl umbelliferyl cellobioside (MUC) as the substrate. Because of the limited availability of purified enzymes, it was not possible to obtain absolute amounts of the enzymes in routine assays, therefore a relative value was calculated. For $T_1$ seed extracts the florescence units (FU) per μg total soluble protein (TSP) assayed was determined. To take into account any variation between assays a positive control using the microbial produced *T. reesei* was used to normalized the fluorescence units run on different days.

The 3 kb globulin-1 promoter was previously found to support a two-fold greater expression of the GUS reporter gene compared to the 1.4 kb globulin1 promoter (Streatfield 2010). In this study, the 3 kb globulin-1 promoter was used to make constructs with one copy of E1 or CBHI. An exact comparison with the previous work using the 1.4 kb promoter was not possible as the genetic backgrounds are different and there was only a limited amount of T1 generation seed available for the 1.4 kb globulin-1 promoter construct. Nevertheless, the levels of E1 and CBHI between the two sets of promoters were compared but they did not show a statistically significant difference (not shown).

Figure 7A:
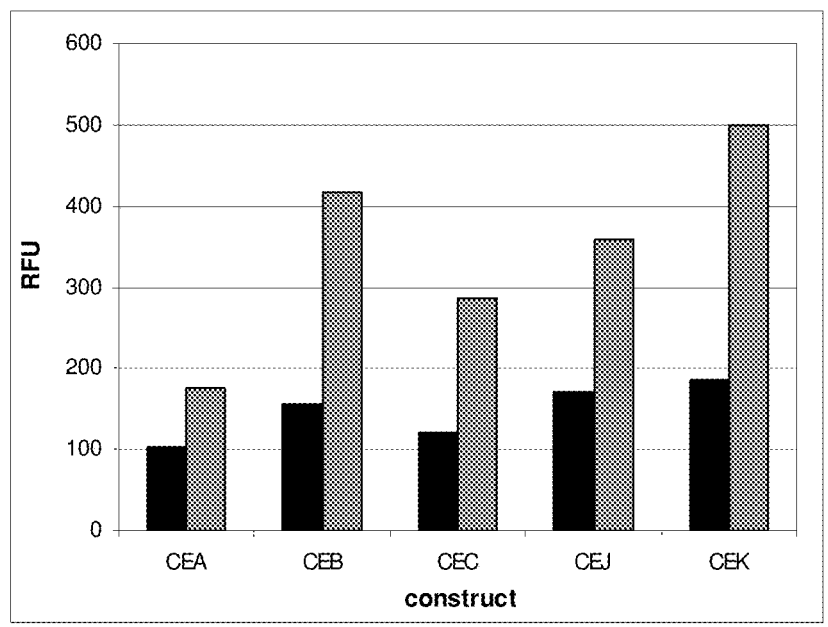
FIGS. 7A and B are a graphs showing cellulase expression in $T_1$ positive seed. The mean RFU (relative fluorescence units) for each construct is shown, either for all seed (black) or the highest ten seed (gray).
Figure 7B:
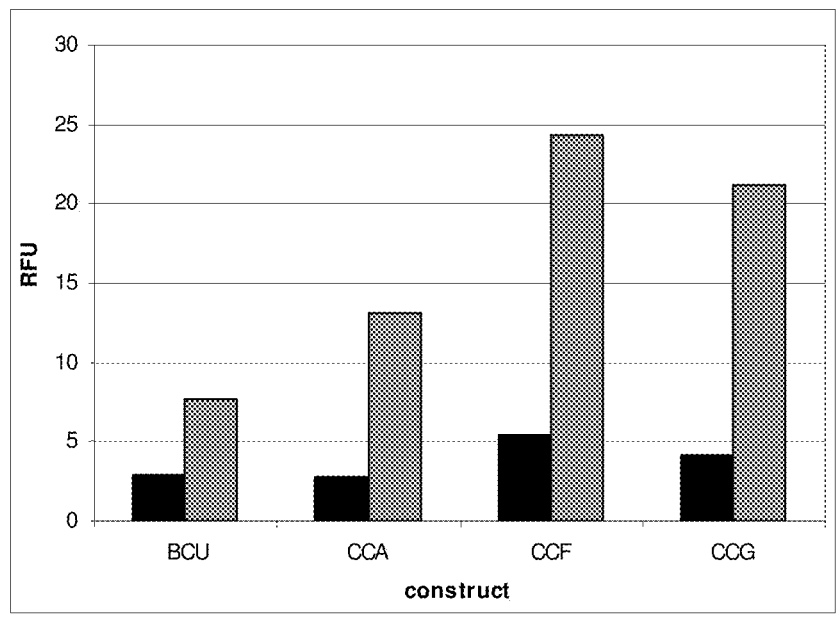

Plants transformed with one copy of E1 (CEA) or CBHI (BCU) under control of the 3 kb globulin-1 promoter were compared with plants with two copies of E1 (CEB) or CBHI (CCA) under control of the same promoter (FIG. 7). It is well established that there can be significant variation in protein accumulation between independent transformation events and even between plants from the same transformation event. There is also substantial precedent that a backcross program selecting the best expressing plants to carry forward at each generation results in a substantial increase in overall expression over time (Hood 2011). Thus, in addition to the overall mean accumulation, a comparison of a selection of the highest expressing plants or seeds may actually be a better indication of the best potential expression for a given construct. The ten highest expressing seeds for each construct were compared as well as the overall mean of all positive seeds. The mean level of E1 increased with the addition of a second copy of the plant transcription unit (PTU) by 50% and the mean value in the ten highest seeds showed a 2.4-fold increase in levels between constructs with one and two PTUs (FIG. 7A; CEA vs. CEB). No difference in the mean levels of all positive CBHI seed upon addition of a second copy was observed but a 1.8-fold increase was observed when comparing the mean of the ten seed with the highest enzyme activity (FIG. 7B; BCU vs. CCA).

To determine if additional copies of the promoter-cellulase transcription unit resulted in still higher expression, constructs with three or four copies were tested with the E1 and CBHI genes. For CBHI the average enzymatic activity in the three-copy construct (CCF) was 2-fold higher than that seen with two copies. However, for E1 the expression levels in the four-copy construct (CEC) are actually less than for the two-copy construct and only 1.2-fold higher than for the one copy construct (FIG. 7).

Rather than using the same promoter to confer expression in multiple PTUs, constructs with three copies of the E1 or CBHI cellulase genes under the control of three different promoters were tested (CEK and CCG). Each of these promoters has been shown to support expression of the GUS reporter gene at levels similar to or greater than the 1.4 kb globulin-1 promoter (Streatfield, 2010). When the three different promoters were used for CBHI (CCG), average expression levels were increased 1.8 fold relative to those observed with one PTU using the 3 kb globulin-1 promoter (BCU). The E1 construct with three different promoters (CEK) also showed 1.8 fold higher levels of expression compared to that of a construct with one PTU driven by the 3 kb globulin-1 promoter (CEA). When the ten highest seeds in the CBHI and EI groups are compared, both enzymes show a three-fold increase over the construct with one copy using the 3 kb globulin-1 promoter (BCU and CEA)(FIG. 7).

The E1 enzyme is targeted to the vacuole for all of the above constructs. Based on previous work (Hood, 2007), E1 targeted to the endoplasmic reticulum (ER) also resulted in high levels of activity. Therefore, a construct with one copy of E1 targeted to the vacuole and one copy of E1 targeted to the ER was evaluated to see if this could result in higher expression (construct CEJ). Expression for this construct was similar to that for the construct with two copies of E1 both targeted to the vacuole (FIG. 7A; CEB vs. CEJ). Finally a construct with two copies of E1 under control of the pr36 promoter as another example of multiple transcription units was examined. This construct also supported accumulation of E1 similar to the construct with two copies of the 3 kb globulin-1 promoter.

To further assess the differences in expression levels for the different constructs, statistical analysis was performed (FIG. 7). For both E1 and CBHI the mean expression levels for all positive seed in different constructs were not found to be statistically different. However, a clear trend towards increasing the mean activity was seen upon addition of multiple copies of the transcription units. When the seed demonstrating the ten highest levels of activity were compared for E1, statistically significant increases in accumulation were achieved with constructs containing multiple copies of the enzyme coding region (p<0.0001; FIG. 7). The groups of constructs as determined by the Tukey-Kramer test for E1 showed that CEK, CEB, and CEL had similar levels of activity and that it was higher than the other three constructs, although CEL and CEB could not be distinguished from CEJ. When seed demonstrating the ten highest levels of activity were compared for CBHI, statistically significant (p<0.0001) increases in accumulation were found, with BCU<CCA<CCF and CCG.

To establish the absolute amount of enzymatic activity in seed extracts, 4-methylumbelliferyl-β-D-cellobioside (MUC) assays were performed using known amounts of purified E1 and CBHI as standards. Due to limited availability of purified E1 and CBHI enzymes however, this was impractical for high-throughput assays. Instead, a commercial preparation of *Trichoderma reesei* was used to generate a standard curve for all tests with seed extracts. This was compared to the standard using the purified E1 and CBHI that could then be used to calculate activity. Total soluble protein (TSP) was also measured from $T_1$ seed from plants transformed with E1 and CBHI and used to further normalize inconsistencies in extraction between different samples. Constructs containing three PTUs under control of three different promoters (CEK and CCG) were then compared to pooled seed from maize lines harboring the constructs with E1 and CBHI under control of the 1.4 kb globulin1 promoter after multiple generations of optimization (Hood, 2011). The absolute amounts of cellulase in extracts was then determined by comparing the fluorescence units resulting from the assay of representative seed extracts to that of purified standards and was expressed as % TSP. The % TSP for E1 was calculated at 18.8% for the construct with three different promoters (CEK) and 7.1% for the 1.4 kb globulin-1-E1 extract (BCH). For CBHI the % TSP was 4.1% for the construct with three different promoters (CCG) and 3.2% for the 1.4 kb globulin1-CBH1 extract (BCC). However, it should be noted that the BCH and BCC samples are from pooled heterozygous seed and the expression levels in positive seed are likely to be two-fold higher.

Figure 8A:
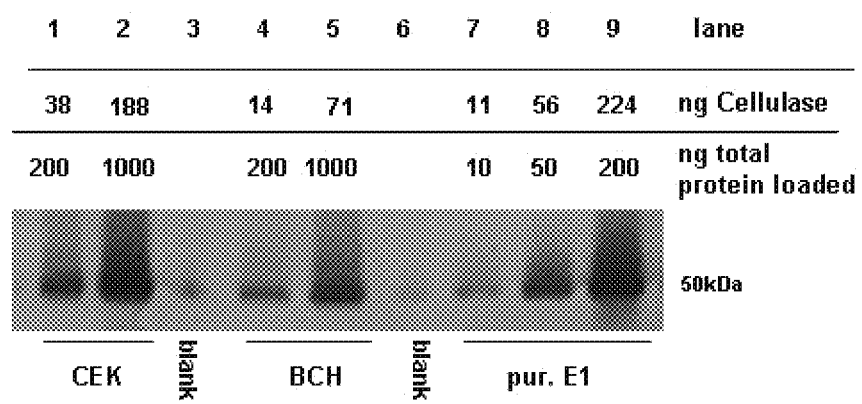
FIGS. 8A and B shows two gels of Western blots, FIG. 8A showing E1 quantitation and FIG. 8B showing CBH1 quantitation.
Figure 8B:
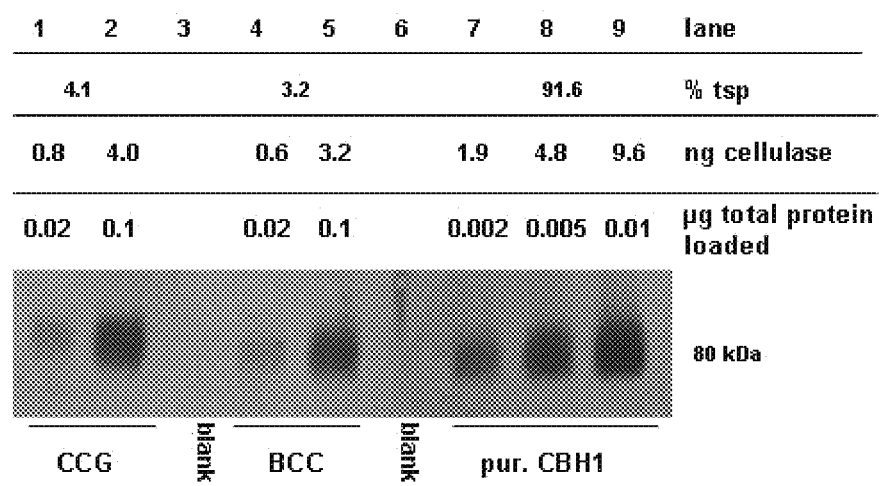

To confirm the amount of cellulase as determined by MUC assay, extracts were also assayed by Western blots. The amount of total protein loaded on the gel was determined by the bicinchonic acid (BCA) protein assay and the amount of E1 or CBHI was calculated by using purified standards with the MUC assay. Increasing amounts of the purified enzymes resulted in a reasonably linear increase in signal (FIGS. 8A and 8B, lanes 7, 8, and 9). A good correlation is observed between the relative band intensities of cellulase on the blots and the amount of cellulase as determined by the MUC assay. These results confirm high levels of E1 and CBHI accumulation using these new constructs in transgenic maize and that most, if not all, of the enzyme is active. They also show that the transgenic protein levels in T1 seed using these new constructs are similar to that achieved after generations of optimization with the BCC and BCH constructs.

Figure 9A:
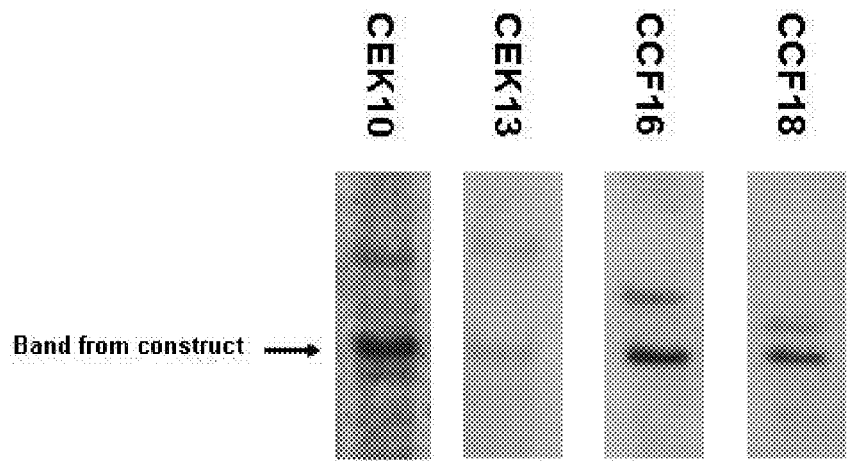
FIG. 9A shows a gel of Southern blot analysis.
Figure 9B:
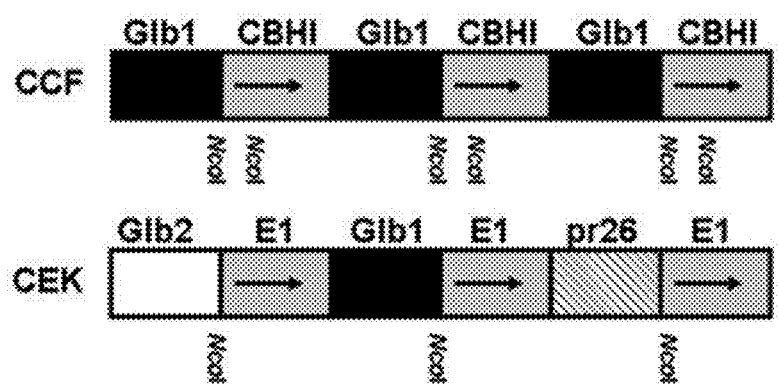
FIG. 9B shows DNA blot analysis of constructs.
Figure 12:
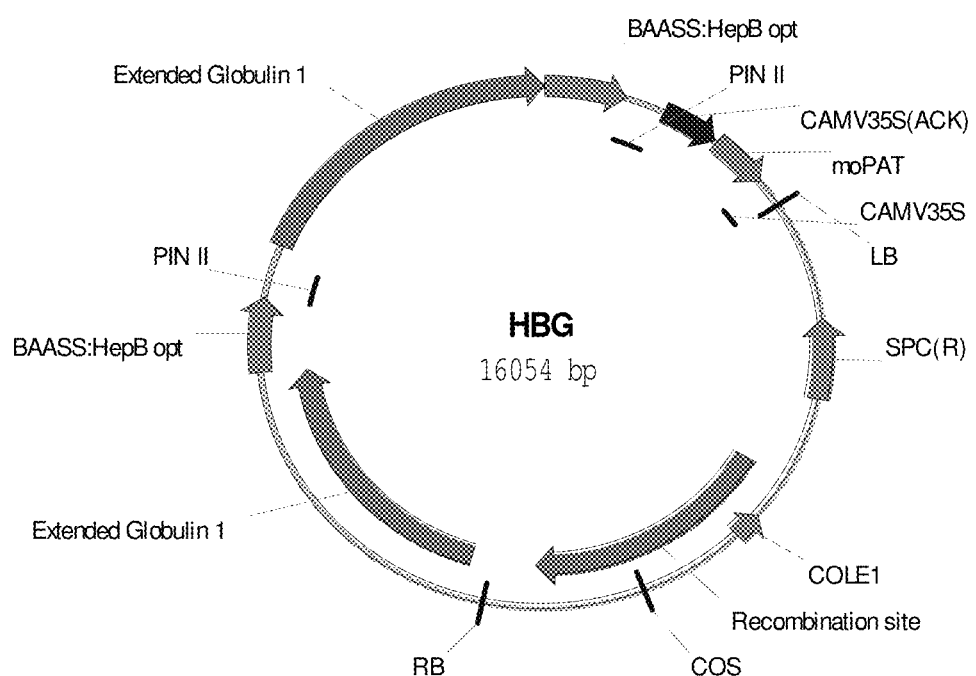
FIG. 12 is a plasmid map of the vector used to express hepatitis B surface antigen.
Figure 13:
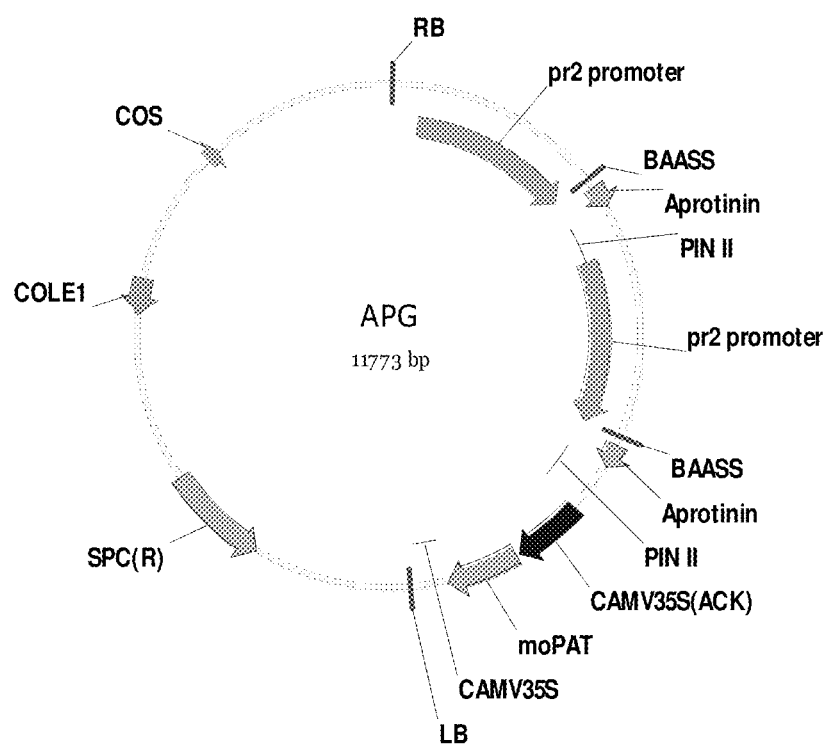
FIG. 13 is a plasmid map of the vector used to express aprotinin.

As transformation may result in integration into one or more locations, it is important to confirm that increases in expression are not simply due to multiple integrations in the chromosomes. Multiple integrations complicate traditional plant breeding approaches and make it difficult to sustain the high levels that can be seen in the $T_1$ seed. To obtain an estimate of copy number and integration patterns, Southern blot (Souther, 1975) analysis was carried out on genomic DNA preparations from selected lines. Blots from representative independent transformation events from the two best expressing constructs with three copies of CBHI under the control of the globulin1 promoter (CCF) and three copies of E1 under the control of different promoters (CEK) are shown in FIG. 9A. For both constructs, the lower band of 4.4 kb-5 kb is an internal fragment expected to be present within the construct. The presence of one additional higher molecular weight band resulting from hybridization to the last PTU (FIG. 9B) is consistent with a single insertion for at least some of the highest-expressing events.

The most promising plants from the T1 analysis were chosen to confirm that expression is maintained in the $T_2$ generation and to begin the process of optimization in germplasm. Seed from two plants for E1 and two plants for CBHI were planted in the greenhouse and back-crossed to an elite line (16038). Twenty-five $T_2$ seed from the resulting plants were ground into a powder and were assayed as described above. In this case only half of the pooled seed are expected to contain the transgene and therefore it is expected that the level of activity should be half of that obtained when comparing to the parent $T_1$ seed. The results shown in FIG. 10 indicate that the $T_2$ seed for constructs CEK, CEB, CCF, and CCG have maintained activity at least as high as the average activity in T1 seed for that construct and nearly as high as the average activity observed in $T_1$ seed from the corresponding event only. This provides evidence that the levels of activity seen in $T_1$ seed can be maintained or even increased as has been done previously for later generations (Hood, 2011).

Experimental Procedures

Construct Preparation

A 3 kb fragment of the promoter region of the maize globulin-1 gene (Streatfield, 2010) was fused to the coding region for the *T. reesei* CBH I gene by standard molecular biology techniques (construct BCU). To prepare a construct with one copy of the *Acidothermus cellulyticus* E1 coding region downstream of 3 kb globulin-1 promoter (construct CEA), an NcoI-NheI fragment containing the E1 coding region was isolated from the previously described construct with E1 downstream of the 1.4 kb globulin-1 promoter (BCH) (Hood, 2007) and ligated to an NcoI/NheI fragment from BCU containing the vector and promoter sequence. The E1 (here SEQ ID NO: 18, see FIG. 14) and CBHI sequence (here SEQ ID NO: 19, see FIG. 15) used is that described at US Patent Application No. 20060026715, incorporated herein by reference in its entirety (the application showing E1 as sequence 1 and CBHI as sequence 4). CBHI sequence used is that described at GenBank accession No. L22656 and maize optimized The gene was maize optimized for the first 40 amino acids using a PCR based mutagenesis approach—this includes the 24 amino acid BAASS sequence. Codons D346 and D386 were also maize codon optimized to remove the potentially destabilizing sequences at those positions.

Based on previous studies (Hood, 2007) of variation in expression depending on subcellular localization, CBH1 constructs include the barley alpha amylase signal sequence (Rogers, 1985 #462) for cell wall localization and E1 constructs contain a vacuole targeting sequence (Holwerda, 1992 #935):

```
                                              (SEQ ID NO: 15)
Atggcccacgcccgcgtcctcctcctggcgctcgccgtcctggccacg gccgccgtcgccgtcgcctcctcctcctccttcgccgactccaacccg atccggccggtcaccgaccgcgcgcgtccacc
```

All constructs were built using the shuttle vectors pGEM (Promega) or pCR2.1 TOPO® (Invitrogen) and transferred into the plant transformation vector pSB1 (Komari, 1996).

To prepare a construct with two copies of E1 under control of the 3 kb globulin-1 promoter the entire expression cassette was amplified by PCR using the single copy construct (CEA) as a template with the addition of NheI restriction sites on both ends. This second copy was inserted into the NheI restriction site of the single copy construct to prepare construct CEB. To add a third and fourth copy (CEC), the expression cassette was amplified by PCR and with the addition of Nan or XbaI restriction sites on the ends. This expression cassette was inserted into restriction sites engineered into the two or three copy intermediate PCR primers. PCR products were sequenced and mutations were corrected by restriction fragment exchange with the wild type sequence by standard cloning techniques.

Preparation of expression cassettes for the second and third copies of CBHI (constructs CCA and CCF) was also accomplished by PCR amplification. To facilitate cloning of large DNA fragments the cassettes were amplified in two pieces roughly corresponding to the promoter and coding region. A SacII site in the extended globulin promoter and SacII sites in the pGEM vector multiple cloning site were used to reconstruct the full expression cassette in the pGEM shuttle vector before addition to the plant transformation construct in the pSB1 vector. For the second and third copies, AgeI and NheI restriction sites were engineered into the outer ends of the cassette respectively.

As a first step in preparation of constructs with cellulase enzymes under control of different promoters, intermediates were prepared in which the GUS coding region of earlier constructs (Streatfield, 2010) was replaced with CBHI or E1 coding sequence. For the globulin-2 and pr26 promoters, the promoter sequence was amplified by PCR. In some cases the sequence around the translation start site was engineered to correspond more closely to the optimal Kozak sequence. PCR products were sequenced and mutations were corrected by restriction fragment exchange with the wild type sequence by standard cloning techniques. The promoter was then inserted into the 3 kb globulin-1-CBHI plant transformation construct as an AgeI-NcoI fragment. This cloning was accomplished in multiple steps to accommodate an NcoI site in the CBHI coding region and an AgeI site in the globulin-2 promoter. The CBHI coding region was subsequently replaced with an NcoI-PacI fragment containing the E1 coding region to prepare the corresponding E1 construct.

For the pr36 promoter, the use of an NcoI site at the junction of the promoter and coding region was precluded by the presence of NcoI sites in both the promoter and the CBHI coding region. Thus the promoter and CBHI and E1 coding regions were amplified by PCR separately to engineer an XmaI site at the junction between the promoter and coding regions. The full expression cassettes were combined as two XmaI/SacII fragments in the pGEM vector.

For preparation of the construct with E1 under control of three different promoters (CEK) each new expression cassette was isolated as an AscI-MluI restriction fragment and ligated into the AscI restriction site of the preceding intermediate starting with the pr26-E1 expression cassette in pSB1. For preparation of the construct with CBHI under control of three different promoters (CCG), an expression cassette with CBHI under control of the pr36 promoter was added to the globulin-1-CBH1 construct as a PmeI-NotI fragment, and an expression cassette with CBH1 under control of the globulin-2 promoter was added to the resulting intermediate as an AscI fragment.

For preparation of a construct with E1 targeted to the vacuole and ER (CEJ), a KDEL sequence was added to the carboxy terminal end of the E1 coding region by PCR. The expression cassette was added to a construct with one copy targeted to the vacuole (CEA) as an AscI-MluI fragment.

Maize Transformation

Maize transformation was carried out as previously described using a method modified from Ishida, et al (Ishida, 1996). In brief, the constructs were transferred into the LBA4404 *Agrobacterium* strain containing the vector pSB1 (Komari, 1996) by a triparental mating procedure. The cointegrate DNA was then electroporated into *Agrobacterium tumefaciens* strain EHA101 (Hood, 1986). Maize embryos at roughly 2-4 mm were mixed with *A. tumefaciens* EHA101 with the appropriate vector for transformation. Plants were grown to maturity in the greenhouse and pollinated with HiII to produce $T_1$ seed.

MUC Assays

Six T1 seed were individually pulverized in 50 mM sodium acetate buffer pH 5.0 and total protein was determined by Bradford (Sigma or Bio-Rad) or BCA (Pierce) assay. Approximately 0.5-1.0 µg total soluble protein (TSP) was mixed with the substrate 4 methylumbelliferyl-beta-D-cellobioside substrate (#M6018, Sigma, St. Louis, Mo.) and incubated for 30 minutes for E1 or 2 hours for CBHI.

Fluorescence was read at 360 and 460 nm. Samples were compared to a cellulase mixture from *T. reesei* as a standard (#C8546 Sigma, St. Louis, Mo.).

Typically, to evaluate a maize line overexpressing a protein of interest, the protein can be compared to a purified protein standard. In the case of the E1 and CBHI cellulase enzymes, however, accurate quantitation of large numbers of samples is complicated by a limited availability of purified enzymes for comparison in high-throughput assays. Therefore, for screening the large numbers of plants necessary to identify high-expressing lines, a relative measure of the cellulase activity of extracts based on the raw fluorescence units per microgram total soluble protein normalized to the *Trichoderma reesei* positive control was used. The average for all positive seed or for the highest-expressing ten seed was then calculated.

Statistical Analysis

E1

An analysis of variance was carried out using the mixed procedure in SAS® v9.1 fitting a conditional hierarchical linear model. Each expression construct was considered a fixed effect. Events nested within constructs, and plants nested within events were considered random effects. Since the variances of the responses tended to increase as the construct means increased, constructs were placed into two groupings such that constructs within groups had approximately equal standard deviations and constructs between groups had unequal standard deviations. Specifically, constructs CEA (s.d.=36.501), and CEC (s.d.=47.183) were placed into one group and constructs CEB (s.d.=83.478), CEJ (s.d.=61.106) and CEK (s.d.=114.594) were placed into another. Significant differences were found among the construct means (p=0.0066). Post-hoc pairwise comparisons of construct means within these groups were carried out using the Tukey-Kramer method, allowing for equal standard deviations. Post-hoc pairwise comparisons of construct means between these groups were done using the Tukey-Kramer method, allowing for unequal standard deviations. The experiment-wise error rate was controlled at 0.05.

CBHI

The analysis of variance was carried out using the mixed procedure in SAS® v9.1 fitting a conditional hierarchical linear model. Each expression construct was considered a fixed effect. Events nested within constructs, and plants nested within events were considered random effects. There were no significant differences among the construct means (p=0.1251). Post-hoc pairwise comparisons of construct means are not appropriate.

Western Blot

Extracts were prepared from single seeds in 50 mM sodium acetate pH 5.0 buffer and assayed for total protein using the BCA assay and for cellulase activity using the MUC substrate. Varying amounts of protein were run on Bis-Tris 4-12% NUPAGE® gels (INVITROGEN®, Carlsbad, Calif). Protein was transferred to a PVDF membrane using the iBlot (INVITROGEN®, Carlsbad, Calif). E1 and CBHI were purified as previously described (Hood, 2011). Antibodies raised in rabbits against bacterially expressed E1 and CBHI were used (Hood, 2011). Protein was detected with BCIP®/NBT reagent (Sigma, St. Louis, Mo.).

DNA Blot Hybridization of Transgenic Lines

Genomic DNA was isolated from young leaf tissue using the Plant DNAEASY® Maxi kit (QIAGEN®, Valencia, Calif). Ten µg genomic DNA was digested with AgeI, NcoI, or NheI and run on a 1% agarose gel. DNA was transferred to Invitrogen Bright Star membrane by a standard capillary method in 0.4 M NaOH, 1 M NaCl alkaline transfer buffer.

An approximately 1 kb fragment of E1 or CBHI was amplified by PCR and labeled as probe using the Bright Star psoralen-biotin kit (INVITROGEN®) as per the manufacturer's directions. The blots were hybridized using the probe at ca. 0.1 nM in 100 mM sodium phosphate pH 7.0, 6.7x SSC, 1% SDS, 0.065% bovine serum albumin, 0.065% polyvinylpyrolidone, 0.065% Ficoll, and 0.1 mg/mL salmon sperm DNA. The blots were washed twice for 20 minutes in 2x SSC, 0.4%SDS, twice for 20 minutes in 1x SSC, 0.25% SDS, and twice for 15 minutes in 0.5x SSC, 0.25% SDS. Signal was developed with the Bright Star BioDetect kit (INVITROGEN®) as per manufacturer's directions.

Discussion

A number of studies have attempted to express enzymes required for cell wall deconstruction in plants to enhance the use of agricultural wastes for biofuel production. Expression of E1 up to 26% total soluble protein (TSP) has been reported in the model species *Arabidopsis*, but levels have generally been lower in economically important crop plants (Austin-Phillips, 1999; Dai, 2000; Ziegler, 2000). For example, E1 has been expressed in transgenic maize at levels of 1-2% TSP (Biswas, 2006; Mei, 2009; Ransom, 2007) and at 4.9% TSP in rice (Oraby, 2007). When expression of enzymes including β-glucosidase, endoglucanase, exoglucanase, and xyloglucanse was targeted to the tobacco chloroplast, levels of up to 12% TSP were reported (Gray, 2009; Gray, 2011; Petersen, 2011). Expression of two xylanase enzymes under control of two different promoters, constitutive and grain-specific, has been achieved in maize, although expression resulted in unhealthy plants (Brunecky, 2011; Gray, 2011). E1 expression under control of a constitutive promoter in transgenic maize and tobacco permitted less pretreatment to achieve digestion comparable to the non-transgenic plants (Brunecky, 2011). Despite these advances, further improvements in levels and tissue-specific control of expression are required for economical biofuel production, especially for CBHI.

Future advances may require transformation of multiple transcription units, either for high-level expression of the same gene or expression of multiple genes. The use of different promoters for each transcription unit may alleviate gene silencing, reduce the chances of recombination, or prevent competition between two promoters for the same transcription factors. A set of recently characterized maize embryo-preferred promoters were shown to increase expression of the GUS gene over the well-established 1.4 kb version of the globulin1 promoter (Streatfield, 2010). However, the level of expression of GUS is relatively low and targeted to the cytoplasm. In this study, the functionality of these promoters was tested with CBHI and E1, two highly accumulated, secreted proteins in plants.

CBHI or E1 accumulation was increased by additional copies of the PTU containing the enzyme coding region. For both E1 and CBHI the addition of a second PTU with the extended globulin promoter resulted in an increase in transgenic protein accumulation when the ten highest seeds were analyzed. The addition of a third copy increased expression even more with CBHI, but for E1 cellulase expression decreased with a four-copy construct. There are a number of possible explanations for this but the most likely is gene silencing for the E1 construct, but not CBHI. For CBHI, a construct with three different promoters showed similar high expression to the construct with three PTUs under control of the same promoter. A construct with E1 under control of three different promoters showed elevated expression relative to all other constructs. This indicates that the relatively low amount of E1 in plants using the construct with four copies under control of the same promoter is not due to the inherent properties of the protein but possibly some form of gene silencing or recombination and that the use of different promoters may alleviate this obstacle. In general, the use of constructs with multiple PTUs increased expression by 2 to 3-fold for E1 and CBHI relative to constructs with only one PTU under control of the 3 kb globulin1 promoter when the highest ten seed are considered.

To confirm these results, Western blot analysis was performed as an alternative method of comparing the level of expression of the new constructs with earlier lines. The level of E1 and CBHI in crude extracts as determined by Western blots agreed with that obtained using the enzymatic assay. Expectations are that selection and backcrossing of these new constructs into elite germplasm, preparation of homozygous lines, and eventually homozygous hybrids will further increase expression significantly as has been shown for other proteins including cellulase (Hood, 2011). Although it is not uncommon to observe some decrease in expression in the first generation of crossing into elite germplasm, $T_2$ seed maintained enzyme activity levels as high or higher than the average expression levels in $T_1$ seed for the corresponding construct.

These results show increasing levels of expression can be achieved with multiple copies of a plant transcription unit for cellulase enzymes. They also confirm the ability of several embryo-specific promoters previously tested with a reporter gene to support expression of proteins of economic value. Future overexpression strategies may require the expression of multiple genes simultaneously (reviewed in Douglas, 2009; Halpin, 2005). A number of studies have used gene stacking, in particular for expression of genes involved in vitamin synthesis (Aluru, 2008; Naqvi, 2009; Naqvi, 2010). Others have attempted to increase expression of foreign proteins using multiple copies of the same gene under control of different promoters (Hennegan, 2005). However, many of these reports have used some form of co-transformation or traditional plant breeding. The availability of a variety of promoters for transgene expression that can be used within the same vector as described here provides more effective approaches.

These transgenic lines show great potential for use as a low cost source of cellulase that can reduce the need for expensive enzymes produced by fungal fermentation (Howard, 2007; Howard, 2011). The current data show expression at approximately 2.1 g E1 per kg seed and 0.62 g CBHI per kg seed in constructs with multiple PTUs under control of different promoters. Routine milling and de-germing of corn grain can increase the concentration in the germ ~7-fold. It has been estimated that expression levels of 4% dry weight in the germ may be necessary to impact economical production of biofuels (Howard, 2011). Based on the data above, cellulase expression is now in this targeted range.

Example 2

The foregoing experiment was repeated in which two PTUs were constructed with the same promoter driving a heterologous nucleic acid molecule in a plant. In this instance, the heterologous nucleic acid molecules were hepatitis B antigen and aprotinin.

The Hepatitis B surface antigen (HBsAg) sequence, identical to the surface antigen protein sequence available in GenBank accession 562754.1 (adr subtype, small form i.e. S open reading frame without pre-S1 or pre-S2 sequences), was engineered to be codon optimized for expression in maize in all of the above constructs (See FIG. 11) and the barley alpha amylase signal sequence included in the vector. Rogers, J. C. (1985) "Two barley alpha-amylase gene families are regulated differently in aleurone cells" *J. Biol. Chem.* 260: 3731-3738. See FIG. 11 where the optimized hepatits B surface antigen nucleotide sequence used is shown (SEQ ID NO: 16), with the BAASS sequence in italics (SEQ ID NO: 17) and the ATG start codon and stop codon in bold. The promoter used was driven by the extended globulin-1 promoter (SEQ ID NO: 5). The plasmid map of the vector used is shown in FIG. 12. The aprotinin coding sequence is that disclosed at disclosed at U.S. Pat. No. 5,824,870, incorporated herein by reference in its entirety. The plasmid map of the vector used is shown in FIG. 13.

Maize plant cells were transformed as described in Experiment 1 above and production of the heterologous protein molecule determined. See, e.g. Hayden et al, "Production of highly concentrated, heat-stable hepatitis B surface antigen in maize" *Plant Biotechnology Journal* 2012 October; 10(8):979-84 and Zhong G., Peterson D., Delaney D., Bailey M., Witcher D., Register Iii J., Bond D., Li C., Marshall L., Kulisek E. (1999) Commercial production of aprotinin in transgenic maize seeds. *Molecular Breeding* 5:345-356. Results are summarized in the table below.

TABLE 5

| Protein | Production |
|---|---|
| Aprotinin 1-copy | 125 ug/g |
| Aprotinin 2 copy | 200 ug/g |
| Hep B 1-copy | 0.17% tsp |
| Hep B 2 copy | 0.27% tsp |

REFERENCES

Altschul, S. F., Gish, W., Miller, W., Myers, E. W. and Lipman, D. J. (1990) Basic local alignment search tool. J. Mol. Biol. 215, 403-410.

Altschul, S. F., Madden, T. L., Schaffer, A. A., Zhang, J., Zhang, Z., Miller, W. and Lipman, D. J. (1997) Nucleic Acids Res. 25, 3389-3402.

Aluru M, Xu Y, Guo R, Wang Z, Li S, White W, Wang K and Rodermel S (2008) Generation of transgenic maize with enhanced provitamin A content. J Exp Bot 59:3551-3562.

An, G., Mitra, A., Choi, H. K., Costa, M. A., An, K., Thornburg, R. W. and Ryan, C. A. (1989) Functional analysis of the 3' control region of the potato wound-inducible proteinase inhibitor II gene. Plant Cell 1, 115-122.

Anderson, E. (1944) Sources of effective germplasm in hybrid maize. Annals of the Missouri Botanical Garden 31, 355-361.

Armstrong, C. I. and Green, C. E. (1985) Establishment and maintenance of friable, embryogenic maize callus and involvement of L-proline. Planta 154, 207-214.

Armstrong, C., Green, C. and Phillips, R. (1991) Development and availability of germplasm with high type II culture response. Maize Genet. Coop. News Lett. 65, 92-93.

Austin-Phillips S, Ziegelhoffer T and Will J (1999) Expression of bacterial cellulase genes in transgenic alfalfa (*Medicago sativa* L.), potato (*Solanum tuberosum* L.) and tobacco (*Nicotiana tabacum* L.). Molecular Breeding 5:309-318.

Ausubel F. M., Brent, R., Kingston, R. E., Moore, D. D., Seidman, J. G., Smith, J. A. and Struhl, K. (Eds.) (1993) Current Protocols in Molecular Biology, John Wiley & Sons, New York.

Baker J O, Ehrman C I, Adney W S, Thomas S R and Himmel M E (1998) Hydrolysis of cellulose using ternary mixtures of purified celluloses. Appl Biochem Biotechnol 70-72:395-403.

Bailey, M. R., Woodard, S. L., Callaway, E., Beifuss, K., Magallanes-Lundback, M., Lane, J. R., Horn, M. E., Mallubhotla, H., Delaney, D. D., Ward, M., Van Gastel, F., Howard, J. A. and Hood, E. E. (2004) Improved recovery of active recombinant laccase from maize seed. Appl. Microbiol. Biotechnol. 63, 390-397.

Becker, T. W., Templeman, T. S., Viret, J. F. and Bogorad, L. (1992) The cab-m7 gene: a light-inducible, mesophyll-specific gene of maize. Plant Mol. Biol. 20, 49-60.

Belanger F C and Kriz A L (1989) Molecular Characterization of the Major Maize Embryo Globulin Encoded by the Glb1 Gene. Plant Physiol 91:636-643.

Belanger, F. C. and Kriz, A. L. (1991) Molecular basis for allelic polymorphism of the maize globulin-1 gene. Genetics 129, 863-872.

Biswas G C G, Ransom C and Sticklen M (2006) Expression of biologically active *Acidothermus cellulolyticus* endoglucanase in transgenic maize plants. Plant Science 171:617-623.

Boothe J, Nykiforuk C, Shen Y, Zaplachinski S, Szarka S, Kuhlman P, Murray E, Morck D and Moloney M M (2010) Seed based expression systems for plant molecular farming. Plant Biotechnology Journal 8:588-606.

Bradford, M. M. (1976) A rapid and sensitive method for the quantitation of microgram quantities of protein utilizing the principle of protein-dye binding. Anal. Biochem. 72, 248-254.

Brinch-Pedersen, H., Hatzack, F., Sorensen, L. D. and Holm, P. B. (2003) Concerted action of endogenous and heterologous phytase on phytic acid degradation in seed of transgenic wheat (*Triticum aestivum* L.). Transgenic Res. 12, 649-659.

Broglie, R., Coruzzi, G., Fraley, R. T., Rogers, S. G., Horsch, R. B., Niedermeyer, J. G., Fink, C. L. and Chua, N. H. (1984) Light-regulated expression of a pea ribulose-1,5-bisphosphate carboxylase small subunit gene in transformed plant cells. Science 224, 838-843.

Brunecky R, Selig M J, Vinzant T B, Himmel M E, Lee D, Blaylock M J and Decker S R (2011) In planta expression of *A. cellulolyticus* Cel5A endocellulase reduces cell wall recalcitrance in tobacco and maize. Biotechnology for biofuels 4:1.

Bustos, M. M., Guiltinan, M. J., Jordano, J., Begum, D., Kalkan, F. A. and Hall, T. C. (1989) Regulation of beta-glucuronidase expression in transgenic tobacco plants by an A/T-rich, cis-acting sequence found upstream of a French bean beta-phaseolin gene. Plant Cell 1, 839-853.

Caddick M. X., Greenland, A. J., Jepson, I., Krause, K. P., Qu, N., Riddell, K. V., Salter, M. G., Schuch, W., Sonnewald, U. and Tomsett, A. B. (1998) An ethanol inducible gene switch for plants used to manipulate carbon metabolism. Nat. Biotechnol. 16, 177-180.

Carrillo, C., Wigdorovitz, A., Oliveros, J. C., Zamorano, P. I., Sadir, A. M., Gomez, N., Salinas, J., Escribano, J. M. and Borca, M. V. (1998) Protective immune response to foot-and-mouth disease virus with VP1 expressed in transgenic plants. J. Virol. 72, 1688-1690.

Casas, A. M., Kononowicz, A. K., Zehr, U. B., Tomes, D. T., Axtell, J. D., Butler, L. G., Bressan, R. A. and Hasegawa P. M. (1993) Transgenic sorghum plants via microprojectile bombardment. Proc. Natl. Acad. Sci. USA 90, 11212-11216.

Chatterjee, M., Sparvoli, S., Edmunds, C., Garosi, P., Findlay, K. and Martin, C. (1996) DAG, a gene required for chloroplast differentiation and palisade development in Antirrhinum majus. EMBO J. 15, 4194-4207.

Christensen, A. H., Sharrock, R. A. and Quail, P. H. (1992) Maize polyubiquitin genes: structure, thermal perturbation of expression and transcript splicing, and promoter activity following transfer to protoplasts by electroporation. Plant Mol. Biol. 18, 675-689.

Cornejo, M. J., Luth, D., Blankenship, K. M., Anderson, O. D. and Blechl, A. E. (1993) Activity of a maize ubiquitin promoter in transgenic rice. Plant Mol. Biol. 23, 567-581.

Corpet, F. (1988) Multiple sequence alignment with hierarchical clustering. Nucleic Acids Res. 16, 10881-10890.

Coruzzi, G., Broglie, R., Edwards, C. and Chua, N. H. (1984) Tissue-specific and light-regulated expression of a pea nuclear gene encoding the small subunit of ribulose-1, 5-bisphosphate carboxylase. EMBO J. 3, 1671-1679.

Creissen, G., Edwards, E. A., Enard, C., Wellburn, A. and Mullineaux, P. (1992) Molecular characterization of glutathione reductase cDNA from pea (*Pisum sativum* L.). Plant J. 2, 129-131.

Crossway, A. (1985) Mol. Gen. Genet. 202, 179-185.

Dai Z, Hooker B S, Anderson D B and Thomas S R (2000) Expression of *Acidothermus cellulolyticus* endoglucanase E1 in transgenic tobacco: biochemical characteristics and physiological effects. Transgenic Res 9:43-54.

Daniell, H., Streatfield, S. J. and Wycoff, K. (2001) Medical molecular farming: production of antibodies, biopharmaceuticals and edible vaccines in plants. Trends Plant Sci. 6, 219-226.

De Wilde, C., Van Houdt, H., De Buck, S., Angenon, G., De Jaeger, G. and Depicker, A. (2000) Plants as bioreactors for protein production: avoiding the problem of transgene silencing. Plant Mol. Biol. 43, 347-359.

Della-Cioppa et al. (1987) Plant Physiology 84:965-968

Douglas E and Halpin C (2009) Gene Stacking. Molecular Techniques in Crop Improvement: 613-629.

Elroy-Stein et al. (1989) PNAS USA 86:6126-6130)

Estruch, J. J., Carozzi, N. B., Desai, N., Duck, N. B., Warren, G. W. and Koziel, M. G. (1997) Transgenic plants: an emerging approach to pest control. Nat. Biotechnol. 15, 137-141.

Fan Z and Yuan L Production of multifunctional chimaeric enzymes in plants: a promising approach for degrading plant cell wall from within. Plant Biotechnology Journal 8:308-315.

Feinberg, A. P. and Vogelstein, B. (1983) A technique for radiolabeling DNA restriction endonuclease fragments to high specific activity. Anal. Biochem. 132, 6-13.

Fontes, E. B., Shank, B. B., Wrobel, R. L., Moose, S. P., OBrian, G. R., Wurtzel, E. T. and Boston, R. S. (1991) Characterization of an immunoglobulin binding protein homolog in the maize floury-2 endosperm mutant. Plant Cell 3, 483-496.

Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L. and Woo, S. C. (1983) Expression of bacterial genes in plant cells. Proc. Natl. Acad. Sci. USA, 80, 4803-4807.

Fromm, M., Taylor, L. P. and Walbot, V. (1985) Expression of genes transferred into monocot and dicot plant cells by electroporation. Proc. Natl. Acad. Sci. USA 82, 5824-5828.

Fromm, M. E., Morrish, F., Armstrong, C., Williams, R., Thomas, J. and Klein, T. M. (1990) Inheritance and expression of chimeric genes in the progeny of transgenic maize plants. Biotechnology (N Y) 8, 833-839.

Gallie. (1989) Molecular Biology of RNA, ed. Cech (Liss, N. Y

Gallie et al. (1995) Gene 165(2):233-238

Geffers, R., Cerff, R. and Hehl, R. (2000) Anaerobiosis-specific interaction of tobacco nuclear factors with cis-regulatory sequences in the maize GapC4 promoter. Plant Mol. Biol. 43, 11-21.

Gordon-Kamm, W., Dilkes, B. P., Lowe, K., Hoerster, G., Sun, X., Ross, M., Church, L., Bunde, C., Farrell, J., Hill, P., Maddock, S., Snyder, J., Sykes, L., Li, Z., Woo, Y. M., Bidney, D. and Larkins, B. A. (1990) Transformation of maize cells and regeneration of fertile transgenic plants. Plant Cell 2, 603-618.

Gould, S. J., Keller, G. A., Hosken, N., Wilkinson, J. and Subramani, S. (1989) A conserved tripeptide sorts proteins to peroxisomes. J. Cell. Biol. 108, 1657-1664.

Gray B N, Yang H, Ahner B A and Hanson M R (2011) An efficient downstream box fusion allows high-level accumulation of active bacterial beta-glucosidase in tobacco chloroplasts. Plant Molecular Biology:1-11.

Grdzelishvili, V. Z., Chapman, S. N., Dawson, W. O. and Lewandowski, D. J. (2000) Mapping of the tobacco mosaic virus movement protein and coat protein subgenomic RNA promoters in vivo. Virology 275, 177-192.

Gruber et al. (1993) Vectors for plant transformation. In: Glick, B. R. and Thompson J. E. (Eds.) Methods in Plant Molecular Biology and Biotechnology, CRC Press, pp. 89-119.

Guilley, H., Dudley, R. K., Jonard, G., Balazs, E. and Richards, K. E. (1982) Transcription of Cauliflower mosaic virus DNA: detection of promoter sequences, and characterization of transcripts. Cell 30, 763-773.

Gurley, W. B., Czarnecka, E., Nagao, R. T. and Key, J. L. (1986) Upstream sequences required for efficient expression of a soybean heat shock gene. Mol. Cell. Biol. 6, 559-565.

Halpin C (2005) Gene stacking in transgenic plants—the challenge for 21st century plant biotechnology. Plant Biotechnology Journal 3:141-155.

Haq, T. A., Mason, H. S., Clements, J. D. and Arntzen, C. J. (1995) Oral immunization with a recombinant bacterial antigen produced in transgenic plants. Science 268, 714-716.

Hennegan K, Yang D C, Nguyen D, Wu L Y, Goding J, Huang J M, Guo F L, Huang N and Watkins S (2005) Improvement of human lysozyme expression in transgenic rice grain by combining wheat (*Triticum aestivum*) puroindoline b and rice (*Oryza sativa*) Gt1 promoters and signal peptides. Transgenic Research 14:583-592.

Hiei, Y., Ohta, S., Komari, T. and Kumashiro, T. (1994) Efficient transformation of rice (*Oryza sativs* L.) mediated by *Agrobacterium* and sequence analysis of the boundaries of the T-DNA. Plant J. 6, 271-282.

Higgins, D. G. and Sharp, P. M. (1988) CLUSTAL: a package for performing multiple sequence alignment on a microcomputer. Gene 73, 237-244.

Higgins, D. G. and Sharp, P. M. (1989) Fast and sensitive multiple sequence alignments on a microcomputer. Comput. Appl. Biosci. 5, 151-153.

Holwerda B C, Padgett H S and Rogers J C (1992) Proaleurain vacuolar targeting is mediated by short contiguous peptide interactions. Plant Cell 4:307-318.

Hood E E, Helmer G L, Fraley R T and Chilton M D (1986) The hypervirulence of *Agrobacterium tumefaciens* A281 is encoded in a region of pTiBo542 outside of T-DNA. J Bacteriol 168:1291-1301.

Hood, E. E., Helmer, G. L., Fraley, R. T. and Chilton, M. D. (1986) The hypervirulence of *Agrobacterium tumefaciens* A281 is encoded in a region of pTiBo542 outside of T-DNA. J. Bacteriol. 168, 1291-1301.

Hood, E. E., Witcher, D. R., Maddock, S., Meyer, T., Baszczynski, C., Bailey, M., Flynn, P., Register, J., Marshall, L., Bond, D., Kulisek, E., Kusnadi, A., Evangelista, R., Nikolov, Z., Wooge, C., Mehigh, R. J., Hernan, R., Kappel, W. K., Ritland, D., Li, C-P. and Howard, J. A. (1997) Commercial production of avidin from transgenic maize: characterization of transformant, production, processing, extraction and purification. Mol. Breed. 3, 291-306.

Hood E E, Kusnadi A, Nikolov Z and Howard J A (1999) Molecular farming of industrial proteins from transgenic maize. Adv Exp Med Biol 464:127-147.

Hood, E. E., Woodard, S. L. and Horn, M. E. (2002) Monoclonal antibody manufacturing in transgenic plants—myths and realities. Curr. Opin. Biotechnol. 13, 630-635.

Hood, E. E., Bailey, M. R., Beifuss, K., Magallanes-Lundback, M., Horn, M. E., Callaway, E., Drees, C., Delaney, D. E., Clough, R. and Howard, J. A. (2003) Criteria for high-level expression of a fungal laccase gene in transgenic maize. Plant Biotechnol. J. 1, 129-140.

Hood E E, Love R, Lane J, Bray J, Clough R, Pappu K, Drees C, Hood K R, Yoon S, Ahmad A and Howard J A (2007) Subcellular targeting is a key condition for high-level accumulation of cellulase protein in transgenic maize seed. Plant Biotechnol J 5:709-719.

Hood E E, Devaiah S P, Fake G, Egelkrout E, Teoh K T, Requesens D V, Hayden C, Hood K R, Pappu K M, Carroll J and Howard J A (2011) Manipulating corn germplasm to increase recombinant protein accumulation. Plant Biotechnol J.

Howard J A (2005) Commercialization of biopharmaceutical and bioindustrial proteins from plants. Crop Science 45:468-472.

Howard J A and Hood E E (2007) Methods for growing nonfood products in transgenic plants. Crop Science 47:1255-1262.

Howard J A, Nikolov Z and Hood E (2011) Enzyme Production Systems for Biomass Conversion, in Plant Biomass Conversion (Hood E, Nelson P and Powell R eds) pp 227-255, Chichester: Wiley-BLackwell.

Huang, X., Miller, W., Schwartz, S. and Hardison, R. C. (1992) Parallelization of a local similarity algorithm. Comput. Appl. Biosci. 8, 155-65.

Innis, M., Gelfand, D., Sninsky, J. and White, T. (1990) PCR Protocols: A Guide to Methods and Applications. Academic Press, New York.

Innis, M., Gelfand, D. and Sninsky, J. (1995) PCR Strategies. Academic Press, New York.

Innis, M., Gelfand, D. and Sninsky, J. (1999) PCR Applications: Protocols for Functional Genomics. Academic Press, New York.

Ishida Y, Saito H, Ohta S, Hiei Y, Komari T and Kumashiro T (1996) High efficiency transformation of maize (*Zea mays* L.) mediated by *Agrobacterium tumefaciens*. Nat Biotechnol 14:745-750.

Jefferson, R. A., Kavanagh, T. A. and Bevan, M. W. (1987) GUS fusions: beta-glucuronidase as a sensitive and versatile gene fusion marker in higher plants. EMBO J. 6, 3901-7.

Jensen, N. F. (1988) Plant Breeding Methodology. Interscience.

Jobling et al. (1987) Nature 325:622-625

Kalderon, D., Roberts, B. L., Richardson, W. D. and Smith A. E. (1984) A short amino acid sequence able to specify nuclear location. Cell 39, 499-509.

Karlin, S. and Altschul, S. F. (1990) Methods for assessing the statistical significance of molecular sequence features by using general scoring schemes. Proc. Natl. Acad. Sci. USA 87, 2264-2268.

Karlin, S. and Altschul, S. F. (1993) Applications and statistics for multiple high-scoring segments in molecular sequences. Proc. Natl. Acad. Sci. USA 90, 5873-5877.

Khan S, Rajan V and Howard J (in press) Plant Molecular Pharming—Industrial Enzymes Plant Molecular Pharming—Industrial Enzymes, in Encyclopedia of Sustainability Science and Technology: Springer.

Klein, T. M., Arentzen, R., Lewis, P. A. and Fitzpatrick-McElligott, S. (1992) Transformation of microbes, plants and animals by particle bombardment. Biotechnology (N Y) 10, 286-291.

Komari T, Hiei Y, Saito Y, Murai N and Kumashiro T (1996) Vectors carrying two separate T-DNAs for co-transformation of higher plants mediated by *Agrobacterium tumefaciens* and segregation of transformants free from selection markers. Plant Journal 10:165-174.

Kriz A L (1989) Characterization of embryo globulins encoded by the maize Glb genes. Biochem Genet. 27:239-251.

Lamphear, B. J., Streatfield, S. J., Jilka, J. M., Brooks, C. A., Barker, D. K., Turner, D. D., Delaney, D. E., Garcia, M., Wiggins, W., Woodard, S. L., Hood, E. E., Tizard, I. R., Lawhorn, B. and Howard, J. A. (2002) Delivery of subunit vaccines in maize seed. J. Control. Release 85, 169-180.

Lee, N., Wang, Y., Yang, J., Ge, K., Huang, S., Tan, J. and Testa, D. (1991) Efficient transformation and regeneration of rice small cell groups. Proc. Nat. Acad. Sci. USA 88, 6389-6393.

Lessard, P. A., Kulaveerasingam, H., York, G. M., Strong, A. and Sinskey, A. J. (2002) Manipulating gene expression for the metabolic engineering of plants. Metab. Eng. 4, 67-79.

Leung, J., Fukuda, H., Wing, D., Schell, J. and Masterson, R. (1991) Functional analysis of cis-elements, auxin response and early developmental profiles of the mannopine synthase bi-directional promoter. Mol. Gen. Genet. 230, 463-474.

Lommel et al. (1991) Virology 81:382-385

Macejak et al. (1991) Nature 353:90-94

Maiti, I. B., Gowda, S., Kiernan, J., Ghosh, S. K. and Shepherd, R. J. (1997) Promoter/leader deletion analysis and plant expression vectors with the figwort mosaic virus (FMV) full length transcript (FLt) promoter containing single or double enhancer domains. Transgenic Res. 6, 143-156.

Mason, H. S., Lam, D. M. and Arntzen, C. J. (1992) Expression of hepatitis B surface antigen in transgenic plants. Proc. Natl. Acad. Sci. USA 89, 11745-11749.

Mathur, J. and Koncz, C. (1998) PEG-mediated protoplast transformation with naked DNA. Methods Mol. Biol. 82, 267-276.

Matsuoka, K. and Nakamura, K. (1991) Propeptide of a precursor to a plant vacuolar protein required for vacuolar targeting. Proc. Natl. Acad. Sci. USA 88, 834-838.

Mei C, Park S H, Sabzikar R, Callista Ransom C Q and Sticklen M (2009) Green tissue specific production of a microbial endo cellulase in maize (*Zea mays* L.) endoplasmic reticulum and mitochondria converts cellulose into fermentable sugars. Journal of Chemical Technology & Biotechnology 84:689-695.

Meinkoth, J. and Wahl, G. (1984) Hybridization of nucleic acids immobilized on solid supports. Anal. Biochem. 138, 267-284.

Miki, B. and McHugh, S. (2004) Selectable marker genes in transgenic plants: applications, alternatives and biosafety. J. Biotechnol. 107, 193-232.

Mohagheghi A, Grohmann K, Himmel M, Leighton L and Updegraff D M (1986) Isolation and Characterization of Acidothermus-Cellulolyticus Gen-Nov, Sp-Nov, a New Genus of Thermophilic, Acidophilic, Cellulolytic Bacteria. International Journal of Systematic Bacteriology 36:435-443.

Moloney, M. et al. (1989) High efficiency transformation of *Brassica napus* using *Agrobacterium* vectors. Plant Cell Reports 8, 238-242.

Myers, E. W. and Miller, W. (1988) Optimal alignments in linear space. Comput. Appl. Biosci. 4, 11-17.

Naqvi S, Zhu C, Farre G, Ramessar K, Bassie L, Breitenbach J, Perez Conesa D, Ros G, Sandmann G, Capell T and Christou P (2009) Transgenic multivitamin corn through biofortification of endosperm with three vitamins representing three distinct metabolic pathways. Proc Natl Acad Sci USA 106:7762-7767.

Naqvi S, Farre G, Zhu C, Sandmann G, Capell T and Christou P (2010) Simultaneous expression of *Arabidopsis* rho-hydroxyphenylpyruvate dioxygenase and MPBQ methyltransferase in transgenic corn kernels triples the tocopherol content. Transgenic Res 20:177-181.

Needleman, S. B. and Wunsch, C. D. (1970) A general method applicable to the search for similarities in the amino acid sequence of two proteins. J. Mol. Biol. 48, 443-453.

Nessler, C. L. (1994) Metabolic engineering of plant secondary products. Transgenic Res. 3, 109-115.

Neuhausen, S. (1989) A survey of Iowa Stiff Stalk parents derived inbreds and BSSS(HT)C5 using RFLP analysis. MNL 63, 110-111.

Nieves R A, Chou Y C, Himmel M E and Thomas S R (1995) Quantitation of Acidothermus-Cellulolyticus E1 Endoglucanase and Thermomonospora-Fusca E(3) Exoglucanase Using Enzyme-Linked-Immunosorbent-Assay (Elisa). Applied Biochemistry and Biotechnology 51-2:211-223.

Nigam P S and Singh A (2011) Production of liquid biofuels from renewable resources. Progress in Energy and Combustion Science 37:52-68.

Odell, J. T., Nagy, F. and Chua, N. H. (1985) Identification of DNA sequences required for activity of the cauliflower mosaic virus 35S promoter. Nature 313, 810-812.

Oldach, K. H., Becker, D. and Lorz, H. (2001) Heterologous expression of genes mediating enhanced fungal resistance in transgenic wheat. Mol. Plant. Microbe Interact. 14, 832-838.

Oraby H, Venkatesh B, Dale B, Ahmad R, Ransom C, Oehmke J and Sticklen M (2007) Enhanced conversion of plant biomass into glucose using transgenic rice-produced endoglucanase for cellulosic ethanol. Transgenic Research 16:739-749.

Padh H, Desai P N and Shrivastava N (2010) Production of heterologous proteins in plants: Strategies for optimal expression. Biotechnology Advances 28:427-435.

Pearson, W. R. and Lipman, D. J. (1988) Improved tools for biological sequence comparison. Proc. Natl. Acad. Sci. USA 85, 2444-2448.

Pearson, W. R. (1994) Using the FASTA program to search protein and DNA sequence databases. Methods Mol. Biol. 24, 307-331.

Petersen K and Bock R High-level expression of a suite of thermostable cell wall-degrading enzymes from the chloroplast genome. Plant Molecular Biology:1-11.

Poehlman, J. M. and Sleper, D. A. (1995) Breeding field crops, 4th Edition, Iowa State University Press.

Poirier, Y., Nawrath, C. and Somerville, C. (1995) Production of polyhydroxyalkanoates, a family of biodegradable plastics and elastomers, in bacteria and plants. Biotechnology (N Y) 13, 142-150.

Ransom C, Balan V, Biswas G, Dale B, Crockett E and Sticklen M (2007) Heterologous *Acidothermus cellulolyticus* 1,4-beta-endoglucanase E1 produced within the corn biomass converts corn stover into glucose. Applied Biochemistry and Biotechnology 137:207-219.

Rogers J C (1985) Two barley alpha-amylase gene families are regulated differently in aleurone cells. J Biol Chem 260:3731-3738.

Roussell, D. L., Boston, R. S., Goldsbrough, P. B. and Larkins, B. A. (1988) Deletion of DNA sequences flanking an Mr 19,000 zein gene reduces its transcriptional activity in heterologous plant tissues. Mol. Gen. Genet. 211, 202-209.

Russell, D. A. and Fromm, M. E. (1997) Tissue-specific expression in transgenic maize of four endosperm promoters from maize and rice. Transgenic Res. 6, 157-168.

Sambrook, J., Fritsch, E. F. and Maniatis, T. (1989) Molecular Cloning: A Laboratory Manual, 2nd Edition. Cold Spring Harbor Laboratory Press, Plainview, N. Y.

Shoemaker S, Schweickart V, Ladner M, Gelfand D, Kwok S, Myambo K and Innis M (1983) Molecular-Cloning of Exo-Cellobiohydrolase-I Derived from *Trichoderma-Reesei* Strain-L27. Bio-Technology 1:691-696.

Sims R E, Mabee W, Saddler J N and Taylor M (2010) An overview of second generation biofuel technologies. Bioresour Technol 101:1570-1580.

Smith, T. F. and Waterman, M. S. (1981) Adv. Appl. Math. 2, 482-489.

Sprague, G. F. (1946) Early testing of inbred lines of maize. J. Amer. Soc. Agron. 38, 108-117.

Stacey, J. and Issac, P. G. (1994) Isolation of DNA from plants. Methods Mol. Biol. 28, 9-15. Stiefel, V., Ruiz-Avila, L., Raz, R., Pilar Valles, M., Gomez, J., Pages, M., Martinez-Izquierdo, J. A., Ludevid, M. D., Langdale, J. A., Nelson, T., et al. (1990) Expression of a maize cell wall hydroxyproline-rich glycoprotein gene in early leaf and root vascular differentiation. Plant Cell 2, 785-793.

Streatfield, S. J., Jilka, J. M., Hood, E. E., Turner, D. D., Bailey, M. R., Mayor, J. M., Woodard, S. L., Beifuss, K., Horn, M. E., Delaney, D. E., Tizard, I. R. and Howard, J. A. (2001) Plant-based vaccines: unique advantages. Vaccine 19, 2742-2748.

Streatfield, S. J., Mayor, J. M., Barker, D. K., Brooks, C., Lamphear, B. J., Woodard, S. L., Beifuss, K. K., Vicuna, D. V., Massey, L. A. Massey, Horn, M. E., Delaney, D. D., Nikolov, Z. L., Hood, E. E., Jilka, J. M. and Howard, J. A. (2002) Development of an edible subunit vaccine in corn against enterotoxigenic strains of *Escherichia coli*. In Vitro Cell. Dev. Biol.-Plant 38, 11-17.

Streatfield, S. J., Lane, J. R., Brooks, C. A., Barker, D. K., Poage, M. L., Mayor, J. M., Lamphear, B. J., Drees, C. F., Jilka, J. M., Hood, E. E. and Howard, J. A. (2003) Corn as a production system for human and animal vaccines. Vaccine 21, 812-815.

Streatfield S J (2007) Approaches to achieve high-level heterologous protein production in plants. Plant Biotechnology Journal 5:2-15.

Streatfield S J, Bray J, Love R T, Horn M E, Lane J R, Drees C F, Egelkrout E M and Howard J A (2010) Identification of maize embryo-preferred promoters suitable for high-level heterologous protein production. GM Crops 1:1-11.

Takimoto, I., Christensen, A. H., Quail, P. H., Uchimiya, H. and Toki, S. (1994) Non-systemic expression of a stress-response maize polyubiquitin gene (Ubi-1) in transgenic rice plants. Plant Mol. Biol. 26, 1007-1012.

Velten, J. and Schell, J. (1985) Selection-expression plasmid vectors for use in genetic transformation of higher plants. Nucleic Acids Res. 13, 6981-6998.

Vilardell, J., Mundy, J., Stilling, B., Leroux, B., Pla, M., Freyssinet, G. and Pages, M. (1991) Regulation of the maize rab 17 gene promoter in transgenic heterologous systems. Plant Mol. Biol. 17, 985-993.

Wan, Y. and Lemaux, P. G. (1994) Generation of large numbers of independently transformed fertile barley plants. Plant Physiol. 104, 37-48.

Waterhouse, P. M., Wang, M. B. and Lough, T. (2001) Gene silencing as an adaptive defense against viruses. Nature 411, 834-842.

Weigel, D. and Nilsson, O. (1995) A developmental switch sufficient for flower initiation in diverse plants. Nature 377, 495-500.

Weising, K., Schell, J. and Kahl, G. (1988) Foreign genes in plants: transfer, structure, expression, and applications. Annu. Rev. Genet. 22, 421-477.

Wohlleben, W., Arnold, W., Broer, I., Hillemann, D., Strauch, E. and Puhler, A. (1988) Nucleotide sequence of the phosphinothricin N-acetyltransferase gene from *Streptomyces* virochromogenes Tu494 and its expression in *Nicotiana tabacum*. Gene 70, 25-37.

Woodard, S. L., Mayor, J. M., Bailey, M. R., Barker, D. K., Love, R. T., Lane, J. R., Delaney, D. E., McComas-Wagner, J. M., Mallubhotla, H. D., Hood, E. E., Dangott, L. J., Tichy, S. E. and Howard, J. A. (2003) Maize-derived bovine trypsin: characterization of the first large-scale, commercial protein product from transgenic plants. Biotechnol. Appl. Biochem. 38, 123-130.

Yang, N. S, and Russell, D. (1990) Maize sucrose synthase-1 promoter drives phloem cell-specific expression of GUS gene in transgenic tobacco plants. Proc. Natl. Acad. Sci. USA 87, 4144-4148.

Ye, X., Al-Babili, S., Kloti, A., Zhang, J., Lucca, P., Beyer, P. and Potrykus, I. (2000) Engineering the provitamin A (beta-carotene) biosynthetic pathway into (carotenoid-free) rice endosperm. Science 287, 303-305.

Yu, H. and Kumar, P. P. (2003) Post-transcriptional gene silencing in plants by RNA. Plant Cell Rep. 22, 167-174.

Ziegler M T, Thomas S R and Danna K J (2000) Accumulation of a thermostable endo-1,4 -D-glucanase in the apoplast of *Arabidopsis thaliana* leaves. Molecular Breeding 6:37-46.

Zhong, G-Y, Peterson, D., Delaney, D. E., Bailey, M., Witcher, D. R., Register, J. C. (III), Bond, D., Li, C-P., Marshall, L., Kulisek, E., Ritland, D., Meyer, T., Hood, E. E. and Howard, J. A. (1999) Commercial production of aprotinin in transgenic maize seeds. Mol. Breed. 5, 345-356.

What is claimed is:

1. A method of increasing expression of a nucleic acid molecule, the method comprising introducing into a plant or plant part a construct comprising three plant transcription units (PTU), each of said PTUs comprising components for enhancing expression of an operably linked nucleic acid molecule and where each PTU comprises the same maize globulin 1 seed promoter selected from the group consisting of SEQ ID NO: 1, SEQ ID NO: 2, SEQ ID NO: 5 and SEQ ID NO: 7 operably linked to a nucleic acid molecule encoding exo-β-1,4-glucanase (CBH1), assaying said plants or plant parts for expression of said CBH1 and selecting said plants or plant parts accumulating said CBH1 at levels at least 3 times higher than CBH1 produced in a plant or plant part comprising a single copy of said PTU, said single copy PTU consisting of the same components as each of said multiple PTUs.

2. The method of claim 1, wherein said promoter is selected from the group consisting of SEQ ID NO: 5, and SEQ ID NO: 7.

3. The method of claim 1 wherein said plant or plant part is a corn plant or plant part.

4. The method of claim 1, wherein said promoter is selected from the group consisting of SEQ ID NO: 1 and 5.

5. The method of claim 1, wherein said promoter is selected from the group consisting of SEQ ID NO: 2 and 7.

* * * * *